(12) United States Patent
Kubota et al.

(10) Patent No.: US 11,964,928 B2
(45) Date of Patent: Apr. 23, 2024

(54) ORGANIC COMPOUND, LIGHT-EMITTING DEVICE, LIGHT-EMITTING APPARATUS, ELECTRONIC EQUIPMENT, LIGHTING DEVICE, AND ELECTRONIC DEVICE

(71) Applicant: Semiconductor Energy Laboratory Co., Ltd., Kanagawa-ken (JP)

(72) Inventors: Tomohiro Kubota, Kanagawa (JP); Takeyoshi Watabe, Kanagawa (JP); Satoshi Seo, Kanagawa (JP); Nobuharu Ohsawa, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 633 days.

(21) Appl. No.: 17/054,859

(22) PCT Filed: May 9, 2019

(86) PCT No.: PCT/IB2019/053802
§ 371 (c)(1),
(2) Date: Nov. 12, 2020

(87) PCT Pub. No.: WO2019/220276
PCT Pub. Date: Nov. 21, 2019

(65) Prior Publication Data
US 2022/0204438 A1  Jun. 30, 2022

(30) Foreign Application Priority Data
May 17, 2018  (JP) .................................. 2018-095707

(51) Int. Cl.
*C07C 211/54* (2006.01)
*H10K 85/60* (2023.01)
*H10K 50/17* (2023.01)

(52) U.S. Cl.
CPC .......... *C07C 211/54* (2013.01); *H10K 85/631* (2023.02); *H10K 50/17* (2023.02)

(58) Field of Classification Search
None
See application file for complete search history.

(56) References Cited

U.S. PATENT DOCUMENTS 6,728,278 B2   4/2004   Kahen et al.
6,762,553 B1   7/2004   Yokogawa et al.
(Continued)

FOREIGN PATENT DOCUMENTS

CN   108821984 A   11/2018
JP   11-282181 A   10/1999
(Continued)

OTHER PUBLICATIONS

Liaptsis, G. et al., "Crosslinkable TAPC-Based Hole-Transport Materials for Solution-Processed Organic Light-Emitting Diodes with Reduced Efficiency Roll-Off," Advanced Functional Materials, 2013, vol. 23, No. 3, pp. 359-365.
(Continued)

*Primary Examiner* — Robert S Loewe
(74) *Attorney, Agent, or Firm* — Husch Blackwell LLP

(57) ABSTRACT

A novel organic compound is provided. A novel organic compound having a carrier-transport property is provided. A novel organic compound having a hole-transport property is provided. An organic compound having a low refractive index is provided. An organic compound having a low refractive index and a carrier-transport property is provided. An organic compound having a low refractive index and a hole-transport property is provided. An organic compound represented by the following general formula (G1) is provided.

(Continued)

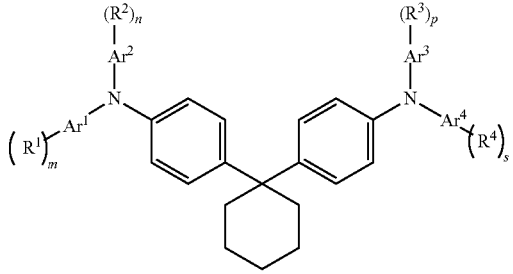

(G1)

22 Claims, 29 Drawing Sheets

(56) References Cited

U.S. PATENT DOCUMENTS

| 9,051,239 | B2 | 6/2015 | Osaka et al. |
| 9,496,505 | B2 | 11/2016 | Nowatari et al. |
| 9,577,222 | B2 | 2/2017 | Seo et al. |
| 9,741,937 | B2 | 8/2017 | Osaka et al. |
| 9,935,292 | B2 | 4/2018 | Seo et al. |
| 2009/0102373 | A1* | 4/2009 | Hayoz ............... C09B 57/00 313/504 |
| 2009/0167156 | A1 | 7/2009 | Kawamura et al. |
| 2010/0104969 | A1 | 4/2010 | Mochizuki et al. |
| 2010/0171417 | A1 | 7/2010 | Kitamura et al. |
| 2010/0301744 | A1 | 12/2010 | Osaka et al. |
| 2012/0080667 | A1 | 4/2012 | Nowatari et al. |
| 2012/0235197 | A1 | 9/2012 | Okuyama |
| 2016/0093678 | A1 | 3/2016 | Seo et al. |
| 2017/0054088 | A1 | 2/2017 | Nowatari et al. |
| 2017/0365782 | A1 | 12/2017 | Osaka et al. |
| 2020/0176692 | A1 | 6/2020 | Watabe et al. |

FOREIGN PATENT DOCUMENTS

| JP | 2008176290 A | * | 7/2008 | ............... G03G 5/05 |
| JP | 2009-091304 A | | 4/2009 | |
| JP | 2010-002695 A | | 1/2010 | |
| JP | 2010-002696 A | | 1/2010 | |
| JP | 2010-002697 A | | 1/2010 | |
| JP | 2014-032851 A | | 2/2014 | |
| TW | 200902592 | | 1/2009 | |
| WO | WO 2008/120470 A1 | | 10/2008 | |

OTHER PUBLICATIONS

International Search Report (Application No. PCT/IB2019/053802) dated Aug. 6, 2019.

Written Opinion (Application No. PCT/IB2019/053802) dated Aug. 6, 2019.

Lee, J. et al., "Synergetic Electrode Architecture for Efficient Graphene-Based Flexible Organic Light-Emitting Diodes," Nature Communications, Jun. 2, 2016, vol. 7, pp. 11791-1-11791-9.

Shin, H. et al., "Sky-Blue Phosphorescent OLEDs with 34.1% External Quantum Efficiency Using a Low Refractive Index Electron Transporting Layer," Advanced Materials, Jun. 22, 2016, vol. 28, No. 24, pp. 4920-4925.

Fuchs, C et al., "Enhanced Light Emission from Top-Emitting Organic Light-Emitting Diodes by Optimizing Surface Plasmon Polariton Losses," Physical Review. B, Dec. 11, 2015, vol. 92, pp. 245306-1-245306-10.

* cited by examiner

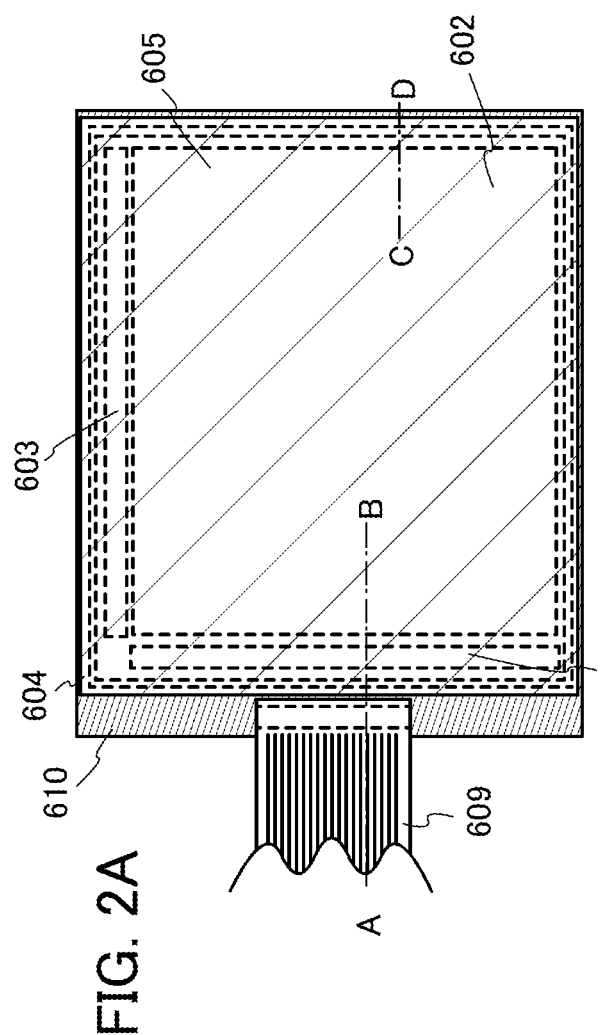
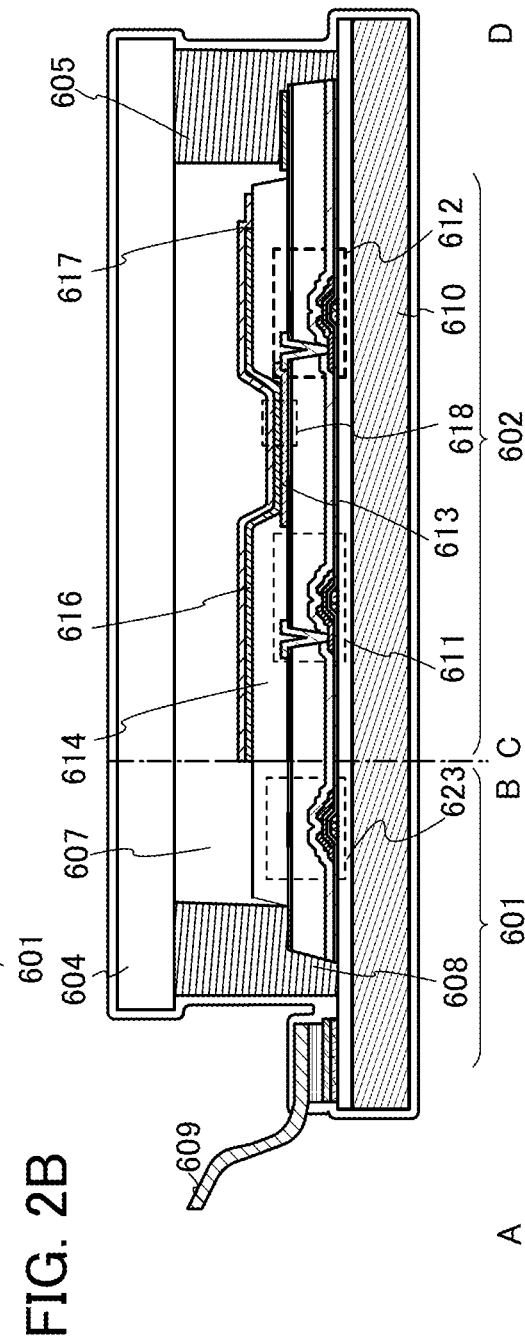
FIG. 2A
FIG. 2B

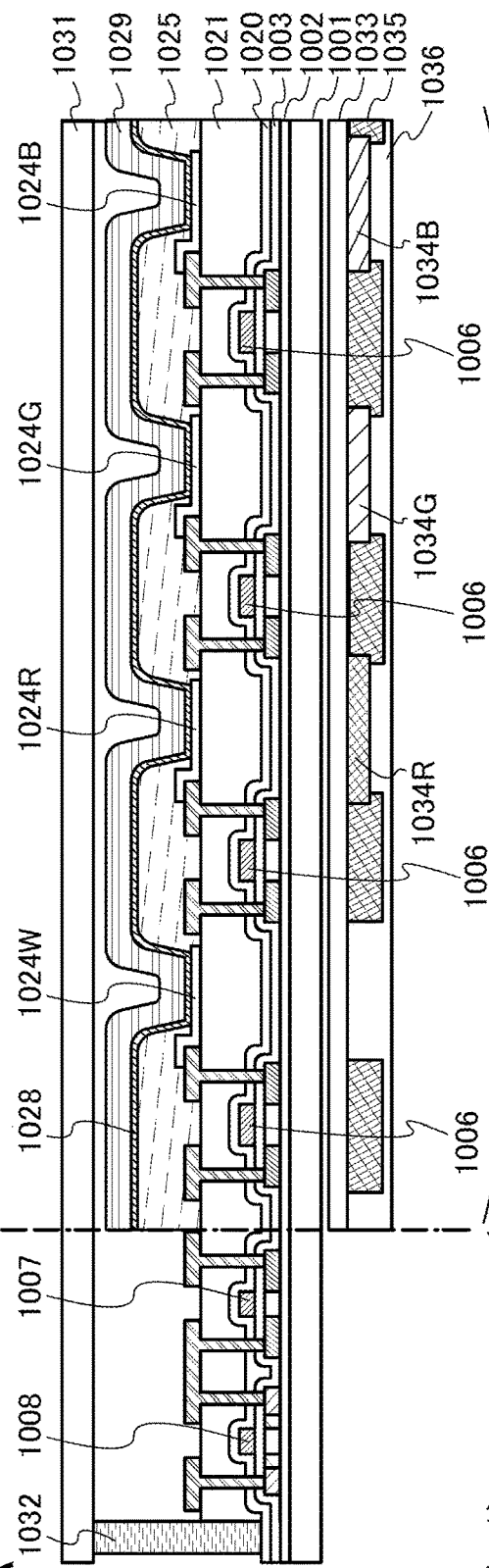
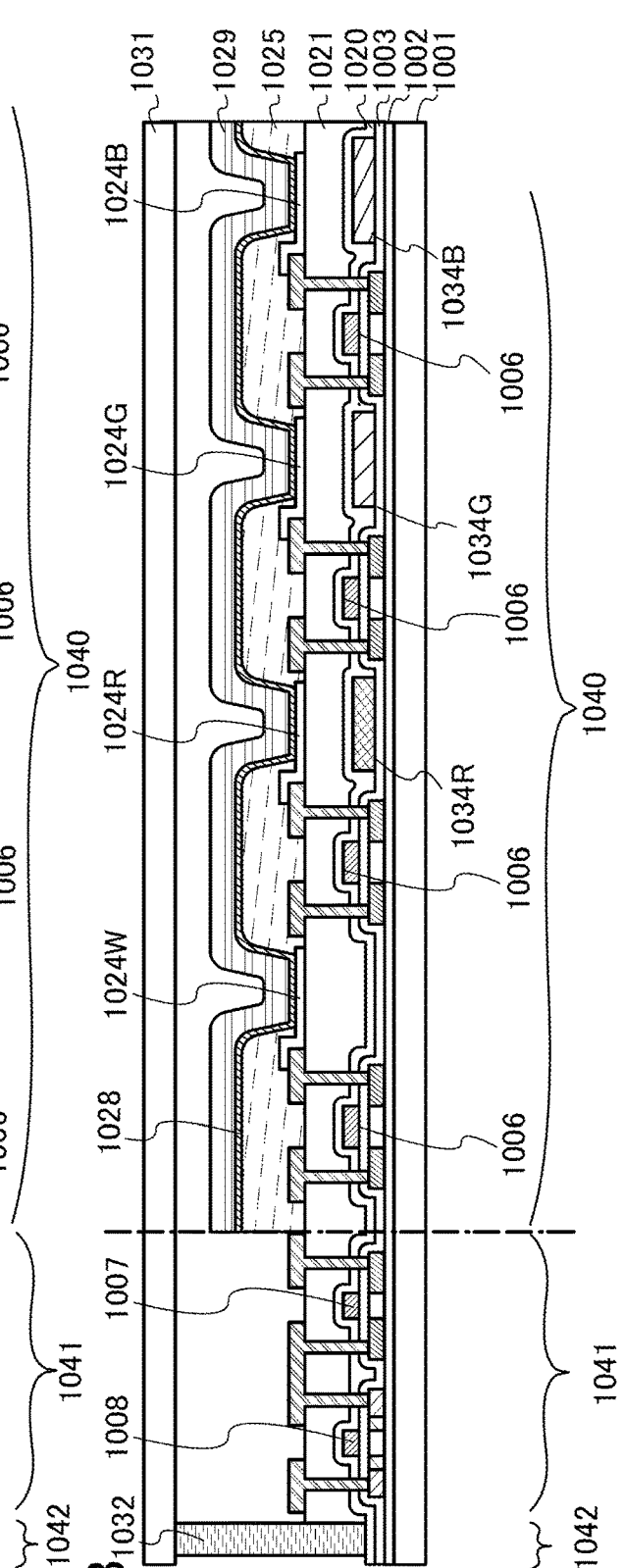
FIG. 3A
FIG. 3B

ORGANIC COMPOUND, LIGHT-EMITTING DEVICE, LIGHT-EMITTING APPARATUS, ELECTRONIC EQUIPMENT, LIGHTING DEVICE, AND ELECTRONIC DEVICE

This application is a 371 of international application PCT/IB2019/053802 filed on May 9, 2019 which is incorporated herein by reference.

TECHNICAL FIELD

One embodiment of the present invention relates to an organic compound, a light-emitting device, a display module, a lighting module, a display device, a light-emitting apparatus, an electronic equipment, a lighting device, and an electronic device. Note that one embodiment of the present invention is not limited to the above technical field. The technical field of one embodiment of the invention disclosed in this specification and the like relates to an object, a method, or a manufacturing method. One embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting apparatus, a lighting device, a power storage device, a memory device, an imaging device, a driving method thereof, and a manufacturing method thereof.

BACKGROUND ART

Light-emitting devices (organic EL devices) that use organic compounds and utilize electroluminescence (EL) have been put into practical use. In the basic structure of such light-emitting devices, an organic compound layer (EL layer) containing a light-emitting material is interposed between a pair of electrodes. Carriers are injected by application of voltage to this device, and recombination energy of the carriers is used, whereby light emission can be obtained from the light-emitting material.

Such light-emitting devices are of self-light-emitting type, and have advantages over liquid crystal, such as high visibility and no need for backlight when used for pixels of a display; accordingly, the light-emitting devices are suitable as flat panel display devices. Displays using such light-emitting devices are also highly advantageous in that they can be fabricated thin and lightweight. Moreover, an extremely fast response speed is also a feature.

Since light-emitting layers of such light-emitting devices can be successively formed two-dimensionally, planar light emission can be obtained. This feature is difficult to obtain with point light sources typified by incandescent lamps and LEDs or linear light sources typified by fluorescent lamps. Thus, light-emitting devices are also of great utility value as planar light sources, which can be applied to lighting and the like.

Displays or lighting devices including light-emitting devices can be suitably used for a variety of electronic equipment as described above, and research and development of light-emitting devices have progressed for better characteristics.

One of the problems often discussed in talking about an organic EL device is outcoupling efficiency being low. In particular, the attenuation due to reflection which is caused by a difference in refractive index between adjacent layers is a main cause of a reduction in display efficiency. In order to reduce this effect, a structure in which a layer formed of a low refractive index material is formed in an EL layer (see Non-Patent Document 1, for example) has been proposed.

Although a light-emitting device having this structure can have higher outcoupling efficiency, and thus higher external quantum efficiency than a light-emitting device having a conventional structure, it is not easy to form such a layer with a low refractive index inside an EL layer without adversely affecting other critical characteristics of the light-emitting device. This is because a low refractive index and a high carrier-transport property or reliability when the material is used for a light-emitting device have a trade-off relation. This is because the carrier-transport property and reliability of an organic compound largely depend on an unsaturated bond, and an organic compound having many unsaturated bonds tends to have a high refractive index.

REFERENCE

Patent Document

[Patent Document 1] Japanese Published Patent Application No. H11-282181
[Patent Document 2] Japanese Published Patent Application No. 2009-91304
[Patent Document 3] United States Patent Application Publication No. 2010/104969
[Non-Patent Document 1] Jaeho Lee and 12 others, "Synergetic electrode architecture for efficient graphene-based flexible organic light-emitting diodes", nature COMMUNICATIONS, Jun. 2, 2016, DOI: 10.1038/ncomms 11791.

SUMMARY OF THE INVENTION

Problems to be Solved by the Invention

An object of one embodiment of the present invention is to provide a novel organic compound. Another object of one embodiment of the present invention is to provide a novel organic compound having a carrier-transport property. Another object of one embodiment of the present invention is to provide a novel organic compound having a hole-transport property. An object of one embodiment of the present invention is to provide an organic compound with a low refractive index. Another object of one embodiment of the present invention is to provide an organic compound with a low refractive index and a carrier-transport property. Another object of one embodiment of the present invention is to provide an organic compound with a low refractive index and a hole-transport property.

An object of another embodiment of the present invention is to provide a light-emitting device with high emission efficiency. Another object of one embodiment of the present invention is to provide a light-emitting device, a light-emitting apparatus, an electronic equipment, a display device, and an electronic device each with low power consumption.

Note that the description of the effects does not preclude the existence of other effects. Note that one embodiment of the present invention does not necessarily have to have all these effects. Effects other than these will be apparent from the description of the specification, the drawings, the claims, and the like and effects other than these can be derived from the description of the specification, the drawings, the claims, and the like.

It is only necessary that at least one of the above-described objects be achieved in the present invention.

Means for Solving the Problems

One embodiment of the present invention is an organic compound represented by a general formula (G1) below.

[Chemical Formula 1]

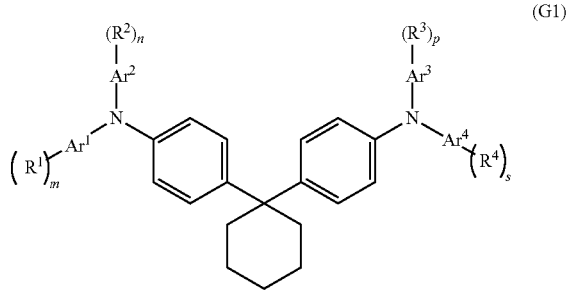

(G1)

In the above general formula (G1), $Ar^1$ to $Ar^4$ each independently represent any of a substituted or unsubstituted phenylene group, a substituted or unsubstituted biphenyldiyl group, and a substituted or unsubstituted triphenyldiyl group. Furthermore, $R^1$ to $R^4$ each independently represent a saturated hydrocarbon group having 5 to 12 carbon atoms or a substituted or unsubstituted cyclic saturated hydrocarbon group having 5 to 12 carbon atoms. Furthermore, m, n, p, and s each independently represent an integer of 0 to 3; however, any two or more of m, n, p, and s each independently represent an integer of 1 to 3.

Another embodiment of the present invention is the organic compound with the above structure in which the $Ar^1$ and $Ar^4$ are substituted or unsubstituted phenylene groups.

Another embodiment of the present invention is the organic compound with the above structure in which the $Ar^2$ and $Ar^3$ are substituted or unsubstituted biphenyldiyl groups.

Another embodiment of the present invention is the organic compound with the above structure in which the $Ar^1$ to $Ar^4$ are substituted or unsubstituted phenylene groups.

Another embodiment of the present invention is the organic compound with any of the above structures in which the m, n, p, and s are each 1.

Another embodiment of the present invention is an organic compound represented by a general formula (G2) below.

[Chemical Formula 2]

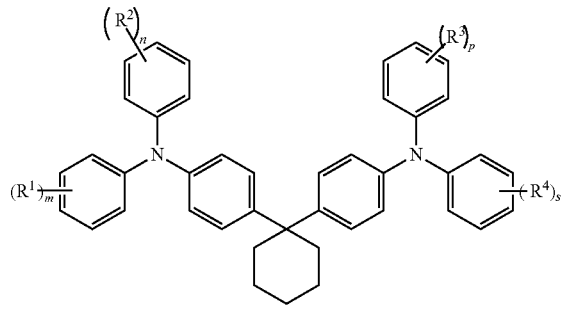

(G2)

In the above general formula (G2), at least one of $R^1$ to $R^4$ represents a saturated hydrocarbon group having 5 to 12 carbon atoms or a substituted or unsubstituted cyclic saturated hydrocarbon group having 5 to 12 carbon atoms, and the rest each independently represent hydrogen, a saturated hydrocarbon group having 5 to 12 carbon atoms, or a substituted or unsubstituted cyclic saturated hydrocarbon group having 5 to 12 carbon atoms. Furthermore, m, n, p, and s each independently represent an integer of 0 to 3; however, any two or more of m, n, p, and s each independently represent an integer of 1 to 3.

Another embodiment of the present invention is an organic compound represented by a general formula (G4 below).

[Chemical Formula 3]

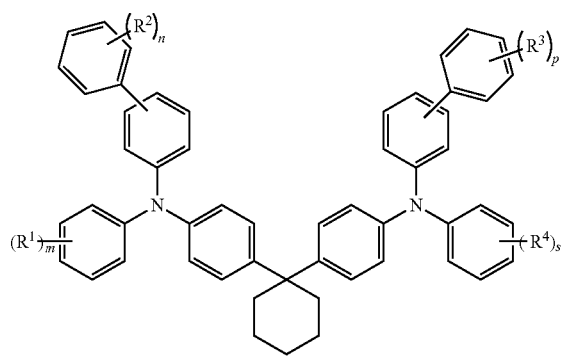

(G4)

In the above general formula (G4), at least one of $R^1$ to $R^4$ represents a saturated hydrocarbon group having 5 to 12 carbon atoms or a substituted or unsubstituted cyclic saturated hydrocarbon group having 5 to 12 carbon atoms, and the rest each independently represent hydrogen, a saturated hydrocarbon group having 5 to 12 carbon atoms, or a substituted or unsubstituted cyclic saturated hydrocarbon group having 5 to 12 carbon atoms. Furthermore, m, n, p, and s each independently represent an integer of 0 to 3; however, any two or more of m, n, p, and s each independently represent an integer of 1 to 3.

Another embodiment of the present invention is an organic compound represented by a general formula (G5) below.

[Chemical Formula 4]

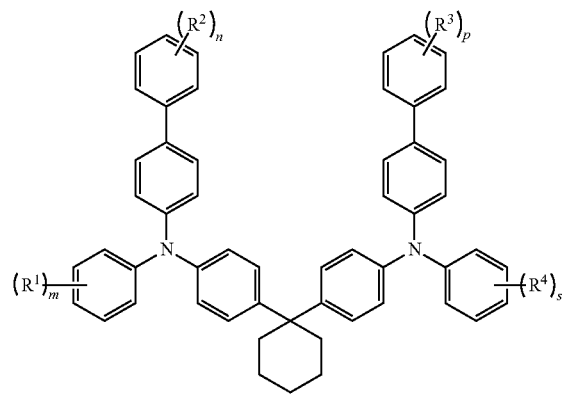

(G5)

In the above general formula (G5), at least one of $R^1$ to $R^4$ represents a saturated hydrocarbon group having 5 to 12 carbon atoms or a substituted or unsubstituted cyclic saturated hydrocarbon group having 5 to 12 carbon atoms, and the rest each independently represent hydrogen, a saturated hydrocarbon group having 5 to 12 carbon atoms, or a substituted or unsubstituted cyclic saturated hydrocarbon group having 5 to 12 carbon atoms. Furthermore, m, n, p, and s each independently represent an integer of 0 to 3; however, any two or more of m, n, p, and s each independently represent an integer of 1 to 3.

Another embodiment of the present invention is an organic compound represented by a general formula (G3) below.

[Chemical Formula 5]

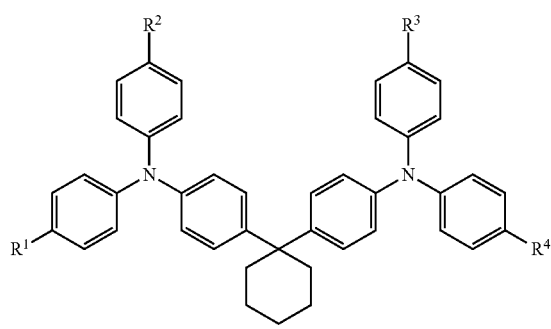

(G3)

In the above general formula (G3), $R^1$ to $R^4$ each independently represent hydrogen, a saturated hydrocarbon group having 5 to 12 carbon atoms, or a substituted or unsubstituted cyclic saturated hydrocarbon group having 5 to 12 carbon atoms.

Another embodiment of the present invention is an organic compound represented by a general formula (G6) below.

[Chemical Formula 6]

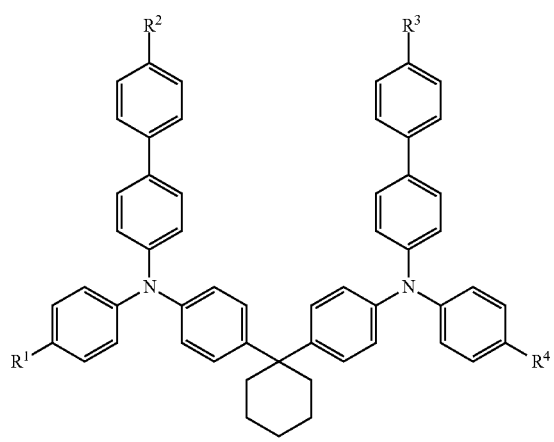

(G6)

In the above general formula (G6), $R^1$ to $R^4$ each independently represent hydrogen, a saturated hydrocarbon group having 5 to 12 carbon atoms, or a substituted or unsubstituted cyclic saturated hydrocarbon group having 5 to 12 carbon atoms.

Another embodiment of the present invention is the organic compound with any of the above structures in which the $R^1$ to $R^4$ are cyclohexyl groups.

Another embodiment of the present invention is an organic compound represented by a structural formula below.

[Chemical Formula 7]

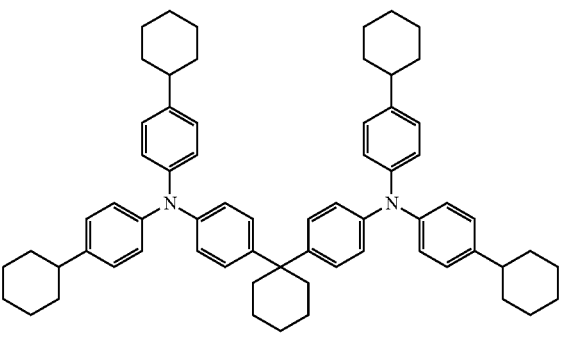

Another embodiment of the present invention is an organic compound represented by a structural formula below.

[Chemical Formula 8]

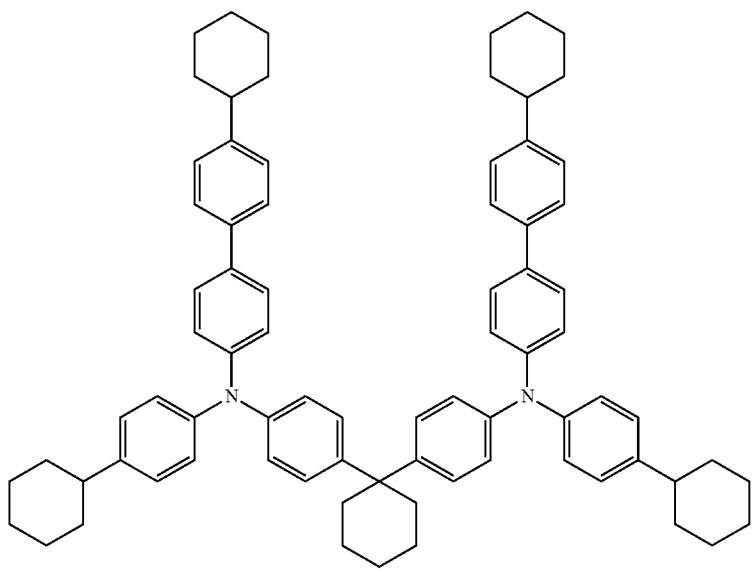

Another embodiment of the present invention is a light-emitting device including a first electrode, a second electrode, and an EL layer positioned between the first electrode and the second electrode, in which the EL layer includes any of the above-described organic compounds.

Another embodiment of the present invention is a light-emitting device including a first electrode, a second electrode, and an EL layer positioned between the first electrode and the second electrode, in which the EL layer includes at least a light-emitting layer and a hole-transport layer, and the hole-transport layer includes any of the above-described organic compounds.

Another embodiment of the present invention is a light-emitting device including a first electrode, a second electrode, and an EL layer positioned between the first electrode and the second electrode, in which the EL layer includes at least a light-emitting layer and a hole-injection layer, and the hole-injection layer includes any of the above-described organic compound accordings.

Another embodiment of the present invention is a light-emitting device including a first electrode, a second electrode, and an EL layer positioned between the first electrode and the second electrode, in which the EL layer includes a light-emitting layer, a hole-transport layer, and a hole-injection layer, and the hole-transport layer and the hole-injection layer include any of the above-described organic compounds.

Another embodiment of the present invention is a light-emitting apparatus including any of the above light-emitting device and a transistor or a substrate.

Another embodiment of the present invention is electronic equipment including the above light-emitting apparatus and a sensor, an operation button, a speaker, or a microphone.

Another embodiment of the present invention is a lighting device including the above light-emitting apparatus and a housing.

Another embodiment of the present invention is an electronic device including any of the above-described organic compounds.

Note that the light-emitting apparatus in this specification includes an image display device using a light-emitting device. The light-emitting (display) device includes, in some cases, a module in which a light-emitting device is provided with a connector such as an anisotropic conductive film or a TCP (Tape Carrier Package), a module in which a printed wiring board is provided at the end of a TCP, or a module in which an IC (integrated circuit) is directly mounted on a light-emitting device by a COG (Chip On Glass) method. Furthermore, in some cases, lighting equipment or the like includes the light-emitting apparatus.

Effect of the Invention

In one embodiment of the present invention, a novel organic compound can be provided. In another embodiment of the present invention, a novel organic compound with a carrier-transport property can be provided. In another embodiment of the present invention, a novel organic compound with a hole-transport property can be provided. In one embodiment of the present invention, an organic compound with a low refractive index can be provided. In another embodiment of the present invention, an organic compound with a low refractive index and a carrier-transport property can be provided. In another embodiment of the present invention, an organic compound with a low refractive index and a hole-transport property can be provided.

In another embodiment of the present invention, a light-emitting device having high emission efficiency can be provided. In another embodiment of the present invention, a light-emitting device, a light-emitting apparatus, an electronic equipment, a display device, and an electronic device each with low power consumption can be provided.

Note that the description of the effects does not preclude the existence of other effects. Note that one embodiment of the present invention does not necessarily have to have all these effects. Effects other than these will be apparent from the description of the specification, the drawings, the claims, and the like and effects other than these can be derived from the description of the specification, the drawings, the claims, and the like.

BRIEF DESCRIPTION OF THE DRAWINGS

FIGS. 2A and 2B are conceptual diagrams of an active matrix light-emitting apparatus.

FIGS. 3A and 3B are conceptual diagrams of active matrix light-emitting apparatuses.

FIGS. 7A-7C are diagrams illustrating electronic equipment.

MODE FOR CARRYING OUT THE INVENTION

Figure 1A:
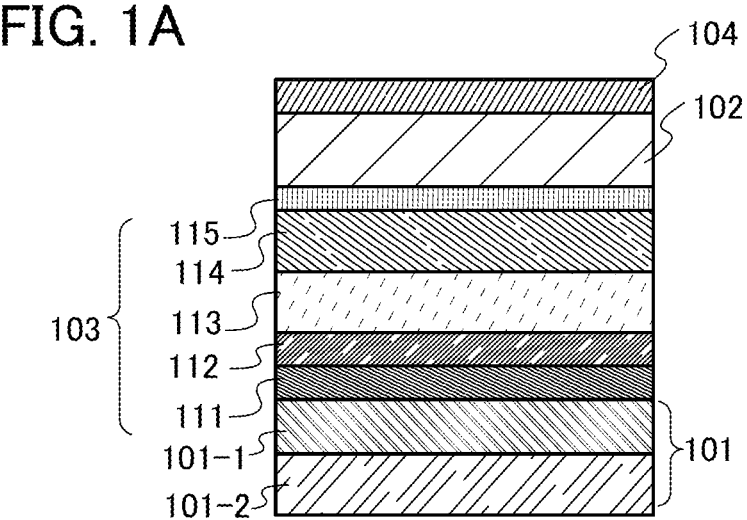
FIGS. 1A-1C are schematic diagrams of light-emitting devices.

Embodiments of the present invention will be described in detail below with reference to drawings. Note that the present invention is not limited to the following description, and it will be readily appreciated by those skilled in the art that modes and details of the present invention can be modified in various ways without departing from the spirit and scope of the present invention. Thus, the present invention should not be construed as being limited to the description in the following embodiments.

Embodiment 1

Among organic compounds that have a carrier-transport property and can be used for an organic EL device, 1,1-bis-(4-bis(4-methyl-phenyl)-amino-phenyl)-cyclohexane (abbreviation: TAPC), which is a material with a low refractive index, is known. The use of such a material with a low refractive index for an EL layer enables a light-emitting device to have high external quantum efficiency; therefore, with the use of TAPC, a light-emitting device with high external quantum efficiency is expected to be obtained. However, TAPC has a problem of being low in heat resistance and thus disadvantageous in terms of reliability.

One of the possible methods for obtaining a hole-transport material with high heat resistance and high reliability is introducing an unsaturated hydrocarbon group, particularly a cyclic unsaturated hydrocarbon group, into a molecule.

Meanwhile, in order to obtain a material with a low refractive index, a substituent with low molecular refraction is preferably introduced into the molecule. Examples of the substituent include a saturated hydrocarbon group and a cyclic saturated hydrocarbon group.

A material used as a carrier-transport material for an organic EL device preferably has a skeleton with a high carrier-transport property, and preferably has an aromatic amine skeleton, in particular.

Based on the above knowledge, the present inventors found out an organic compound that has a low refractive index and can be suitably used as a hole-transport material for an organic EL device, by combining the substituents and skeletons in the following way.

That is, the organic compound of one embodiment of the present invention is an organic compound represented by the following general formula (G1).

[Chemical Formula 9]

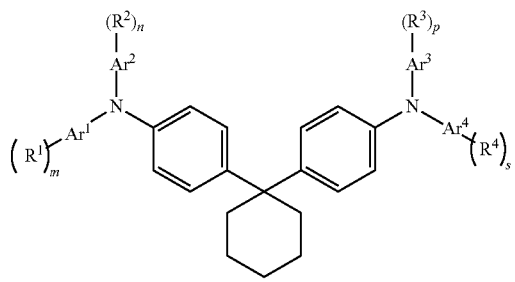

(G1)

In the above general formula (G1), $Ar^1$ to $Ar^4$ each independently represent any of a substituted or unsubstituted phenylene group, a substituted or unsubstituted biphenyldiyl group, and a substituted or unsubstituted triphenyldiyl group.

Note that $Ar^1$ and $Ar^4$ are each preferably a substituted or unsubstituted phenylene group, and more preferably an unsubstituted phenylene group in view of the synthesis cost.

Furthermore, $Ar^2$ and $Ar^3$ are each preferably a substituted or unsubstituted phenylene group, or a substituted or unsubstituted biphenyldiyl group, and more preferably a substituted or unsubstituted phenylene group to have an improved sublimation property. In view of the synthesis cost, an unsubstituted phenylene group is more preferable.

In the case where any of $Ar^1$ to $Ar^4$ is a phenylene group having a substituent, a biphenyldiyl group having a substituent, and a triphenyldiyl group having a substituent, an alkyl group having 1 to 4 carbon atoms can be given as examples of the substituent. As the alkyl group having 1 to 4 carbon atoms, for example, a methyl group, an ethyl group, a propyl group, an isopropyl group, an n-butyl group, a sec-butyl group, an isobutyl group, a tert-butyl group and the like can be given.

Note that $Ar^1$ to $Ar^4$ are each preferably an unsubstituted phenylene group as described above, and the organic compound can be represented by the following general formula (G2).

[Chemical Formula 10]

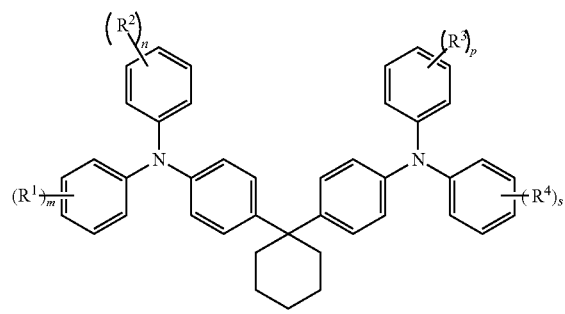

(G2)

In the above general formula (G1), it is preferable that $Ar^2$ and $Ar^3$ be each an unsubstituted biphenyldiyl group and $Ar^1$ and $Ar^4$ be each an unsubstituted phenylene group, as described above. Such an organic compound can be represented by the following general formula (G4).

[Chemical Formula 11]

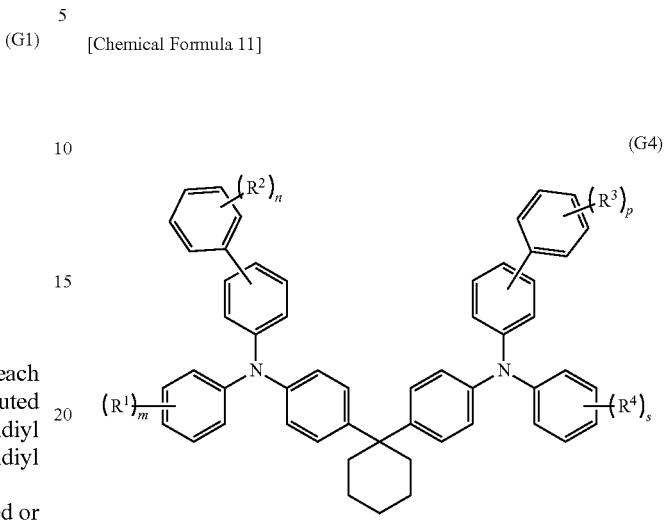

(G4)

In the above general formula (G1), it is preferable that $Ar^2$ and $Ar^3$ be each an unsubstituted biphenyldiyl group and $Ar^1$ and $Ar^4$ be each an unsubstituted phenylene group; it is more preferable that $Ar^2$ and $Ar^3$ be each an unsubstituted 4,4'-biphenyldiyl group. Such an organic compound can be represented by the following general formula (G5).

[Chemical Formula 12]

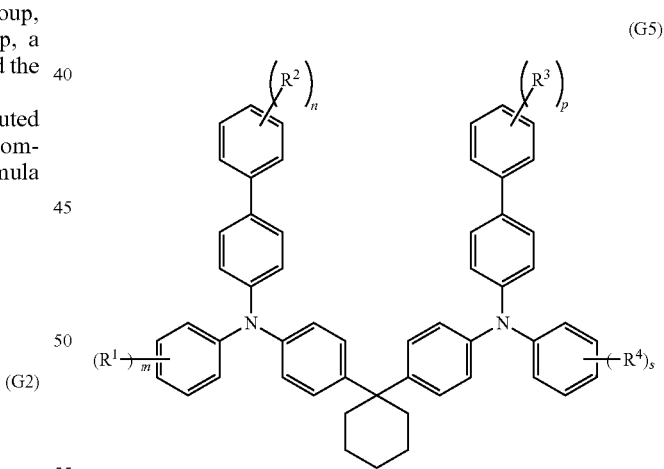

(G5)

Note that in the organic compounds represented by the above general formulae (G1), (G2), (G4), and (G5), m, n, p, and s each independently represent an integer of 0 to 3, and any two or more of m, n, p, and s each independently represent an integer of 1 to 3.

In terms of the easiness of synthesis and stability, it is preferable that m, n, p, and s be 1; such organic compounds, among the organic compounds represented by the above general formulae (G4) and (G5), can be represented by the following general formulae (G3) and (G6).

[Chemical Formula 13]

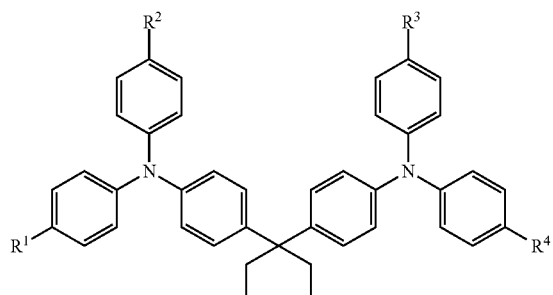

(G3)

[Chemical Formula 14]

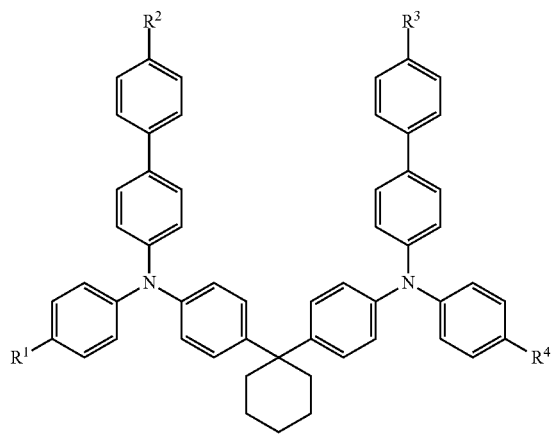

(G6)

Note that in the above general formulae (G1) to (G6), $R^1$ to $R^4$ each independently represent a saturated hydrocarbon group having 5 to 12 carbon atoms or a substituted or unsubstituted cyclic saturated hydrocarbon group having 5 to 12 carbon atoms.

Examples of a saturated hydrocarbon group having 5 to 12 carbon atoms include a pentyl group, an isopentyl group, a sec-pentyl group, a tent-pentyl group, a neopentyl group, a hexyl group, an isohexyl group, a sec-hexyl group, a tent-hexyl group, a neohexyl group, a 3-methylpentyl group, a 2-methylpentyl group, a 2-ethylbutyl group, a 1,2-dimethylbutyl group, a 2,3-dimethylbutyl group, an octyl group, an isooctyl group, a 2,6-dimethylhexyl group, a tent-octyl group, a decane group, a 2,6-dimethyloctyl group, a 3,3-dimethyloctyl group, a 2-methylnonyl group, a 3-methylnonyl group, an undecyl group, and a dodecyl group. Examples of a cyclic saturated hydrocarbon group having 5 to 12 carbon atoms include a cyclopentyl group, a cyclohexyl group, a 1-methylcyclopentyl group, a 2-methylcyclopentyl group, a cycloheptyl group, a bicyclo[2,2,1]heptyl group, cyclooctyl group, a bicyclo[2,2,2]octyl group, a cyclononyl group, a bicyclo[3,2,2]nonyl group, a bicyclo[3,3,1]nonyl group, a cyclodecyl group, a cycloundecyl group, a bicyclo[5,4,0]undecyl group, and a cyclododecyl group.

In the case where any of $R^1$ to $R^4$ is a cyclic hydrocarbon group having 5 to 12 carbon atoms with a substituent, an example of the substituent is an alkyl group having 1 to 4 carbon atoms. As the alkyl group having 1 to 4 carbon atoms, for example, a methyl group, an ethyl group, a propyl group, an isopropyl group, an n-butyl group, a sec-butyl group, an isobutyl group, a tent-butyl group and the like can be given.

Note that it is effective, in view of atomic refraction or molecular refraction, that $R^1$ to $R^4$ are substituents having a cyclic structure because when $R^1$ to $R^4$ are substituents having the same number of carbon atoms, the refractive index is further greatly decreased; more preferably, they are six or more-membered normal-ring and medium-ring substituents. However, when a macrocyclic substituent is introduced, increase in molecular weight may decrease a sublimation property, and it may cause decomposition; thus, they are preferably cyclohexyl groups.

The organic compound having the above structure is an organic compound having a low refractive index and a hole-transport property. Accordingly, a light-emitting device using the organic compound can have high external quantum efficiency.

Specific examples of the organic compound having the above-described structure are shown below.

[Chemical Formulae 15]

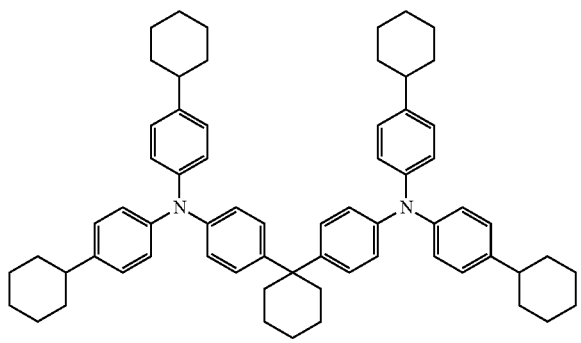

(100)

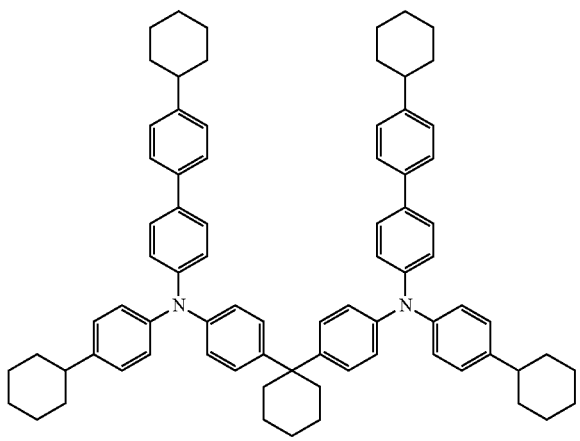

(101)

-continued
(102)
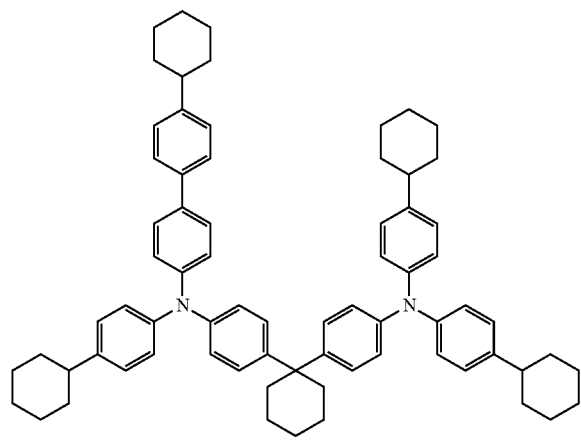
(103)
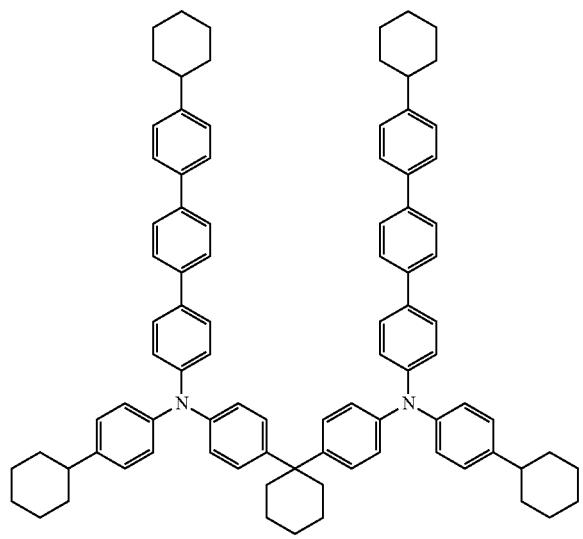
(104)
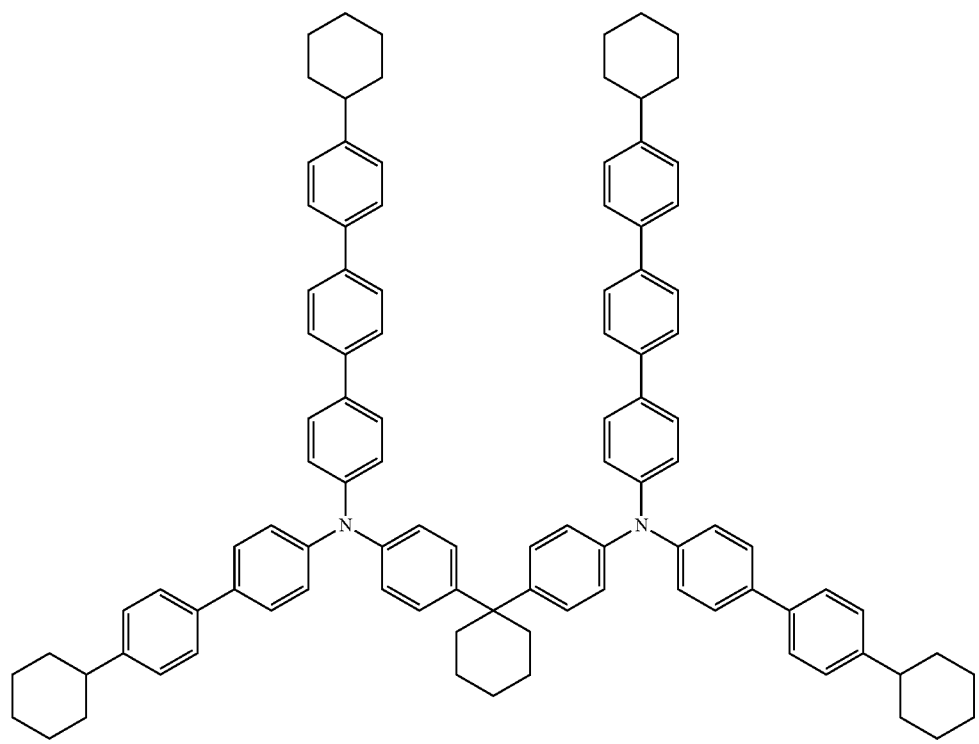

(105)
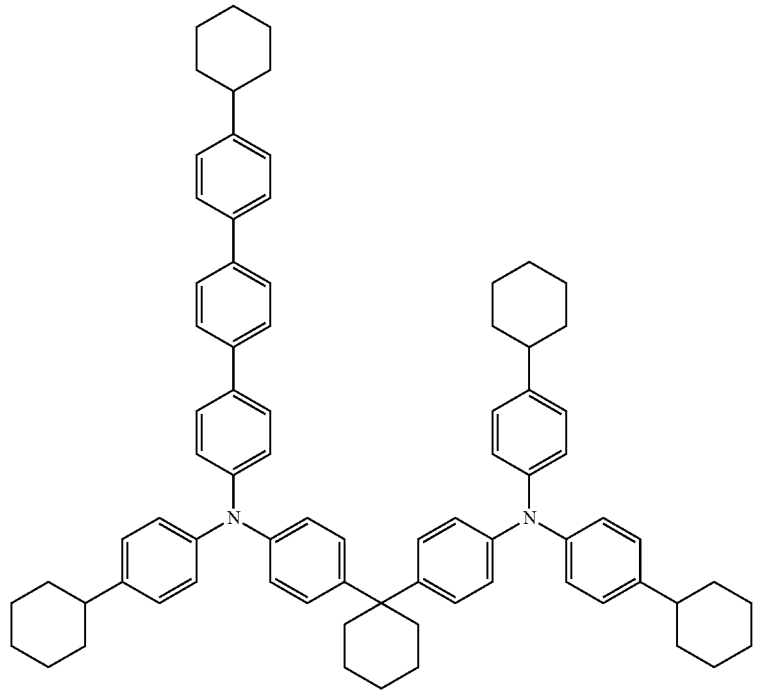
[Chemical Formulae 16]
(106) (107)
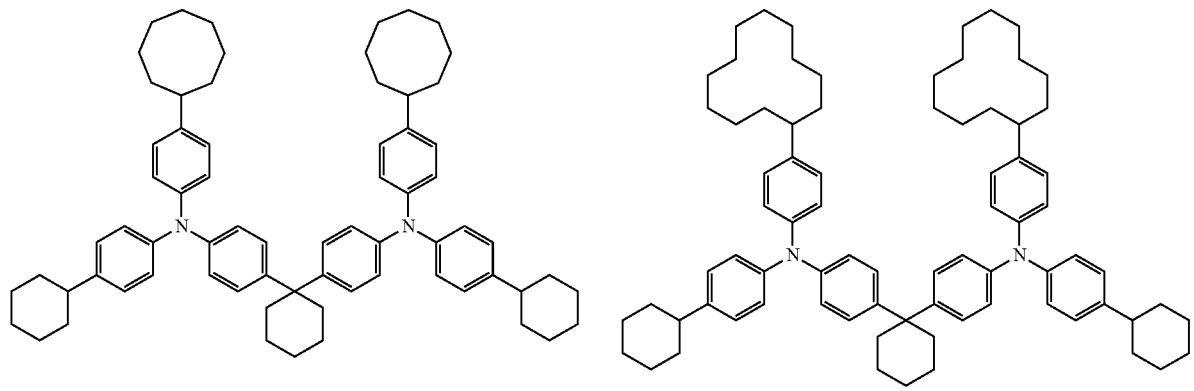
(108) (109)
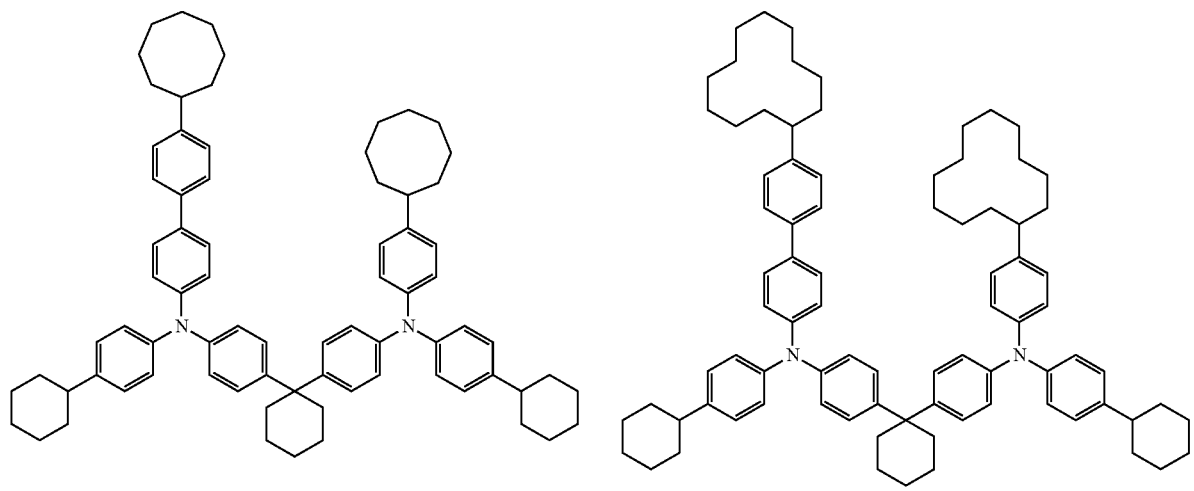

(110)
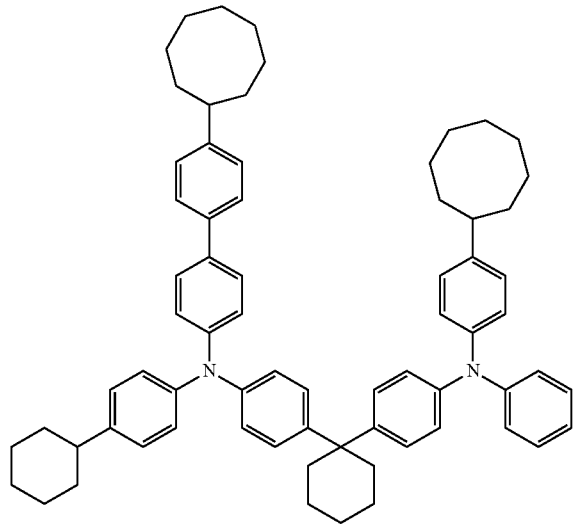
(111)
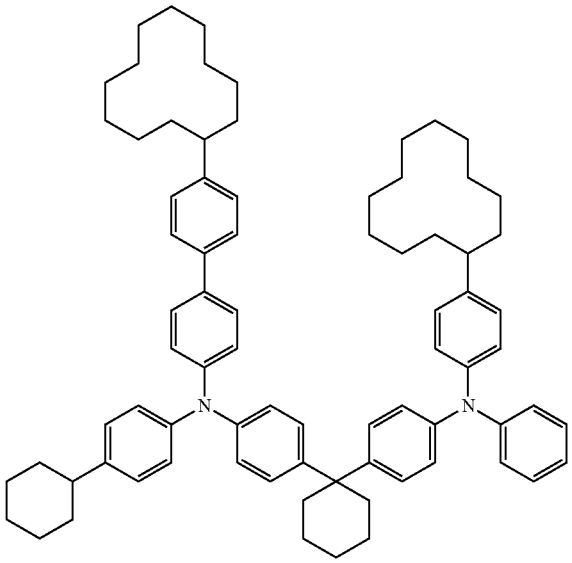
[Chemical Formulae 17]
(112)
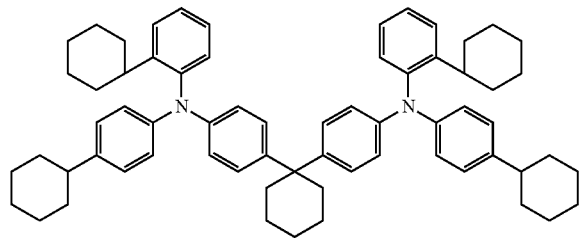
(113)
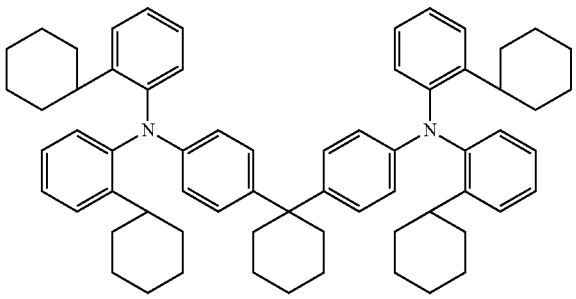
(114)
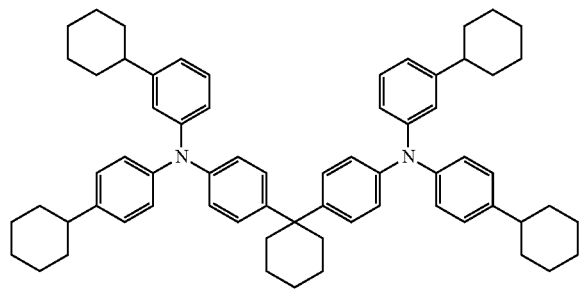
(115)
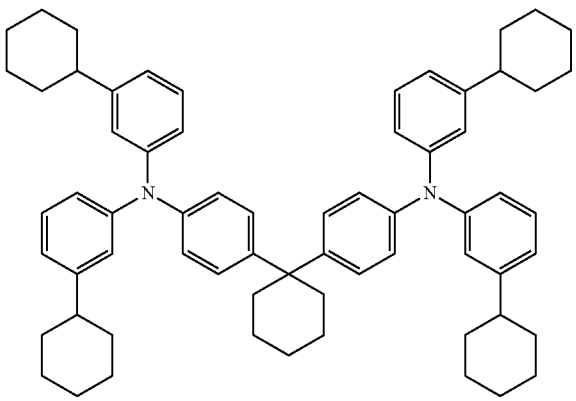

(116) 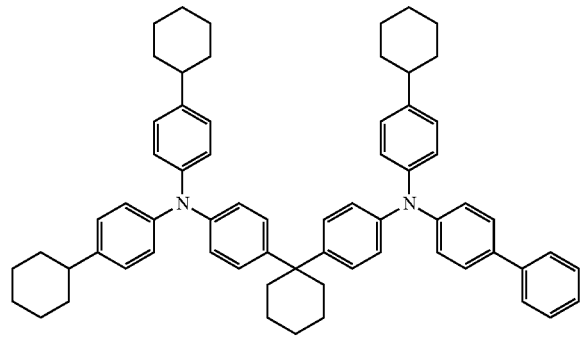
(117) 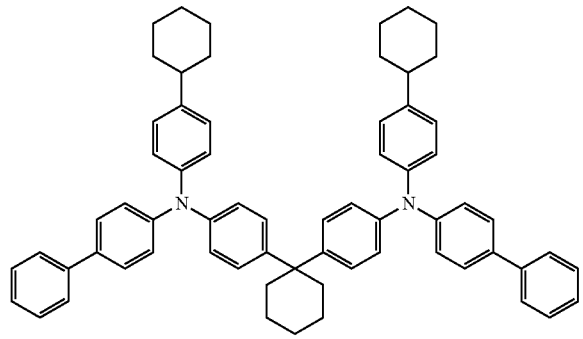
(118) 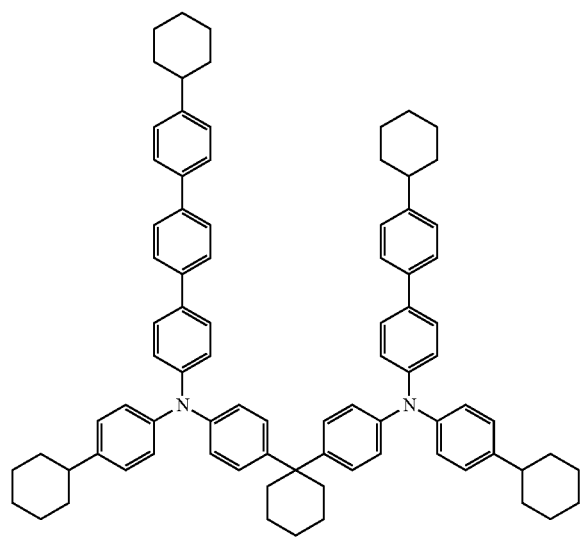
(119) 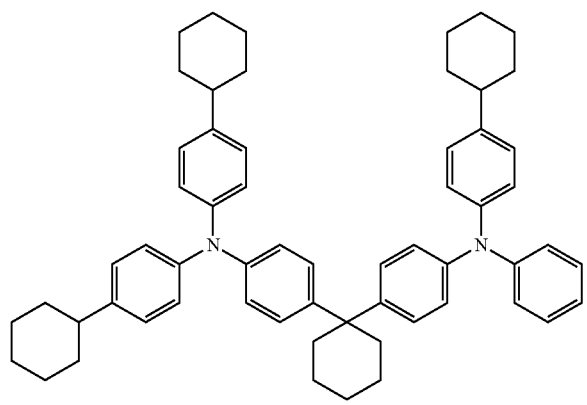
[Chemical Formulae 18]
(120) 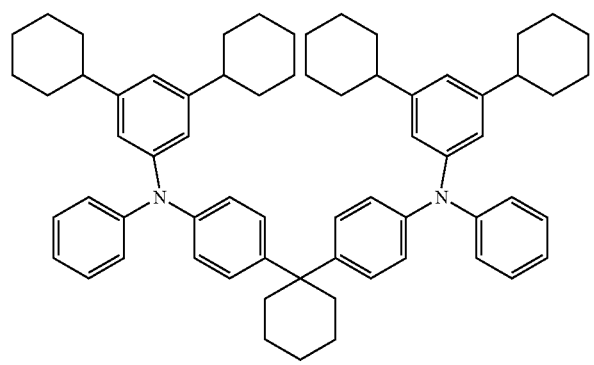
(121) 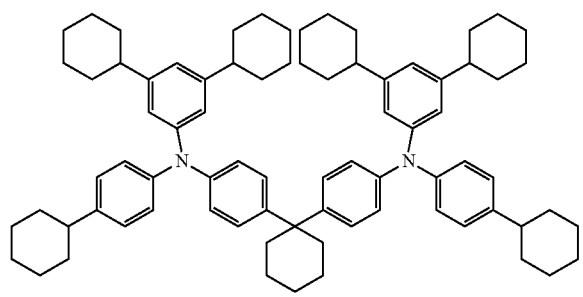

(122)
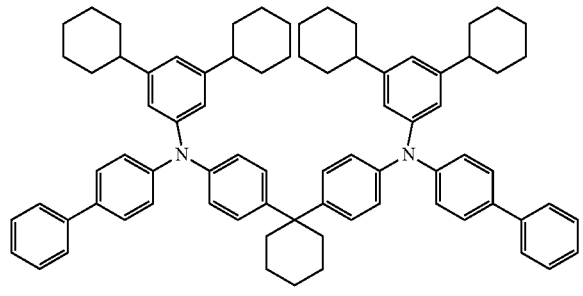
(123)
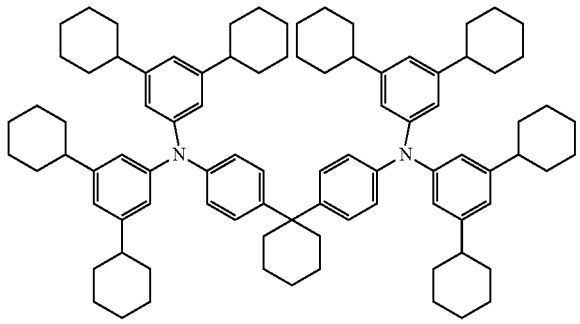
(124)
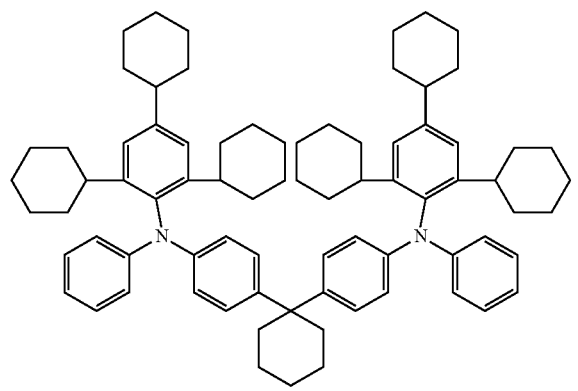
(125)
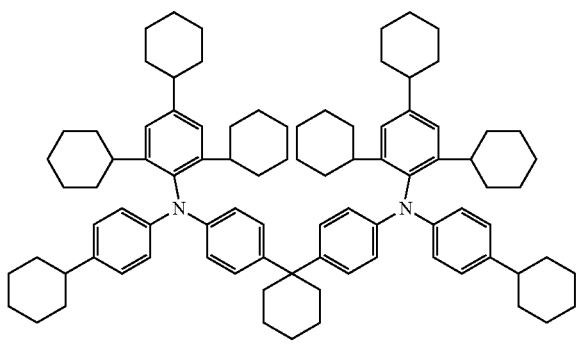
(126)
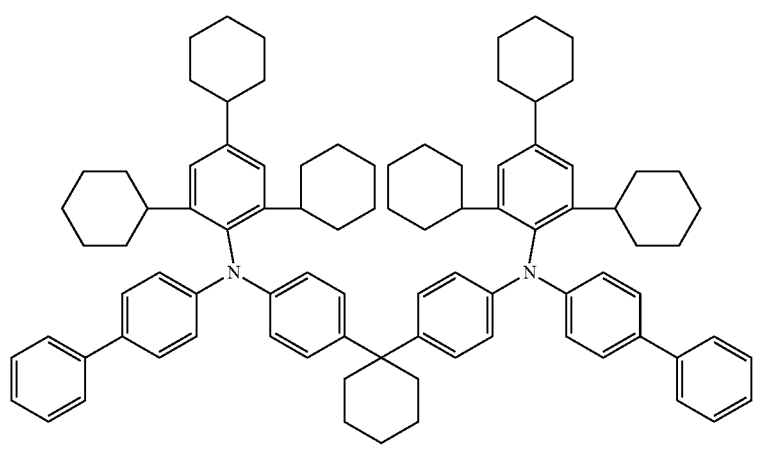

[Chemical Formulae 19]
(127)
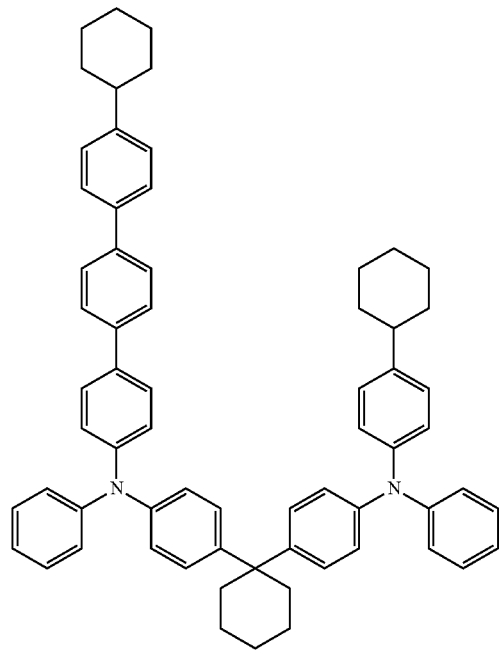
(128)
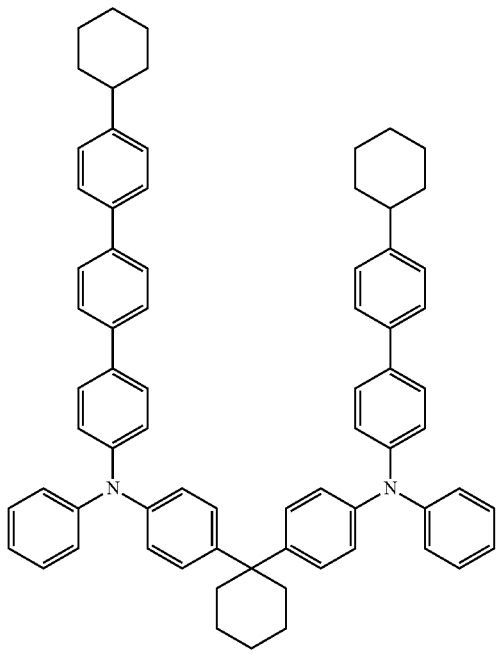
(129)
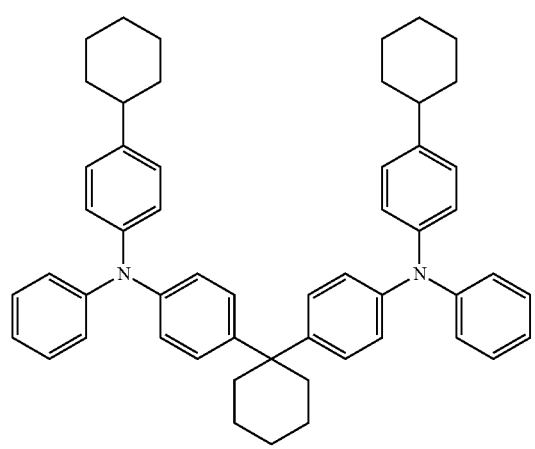
(130)
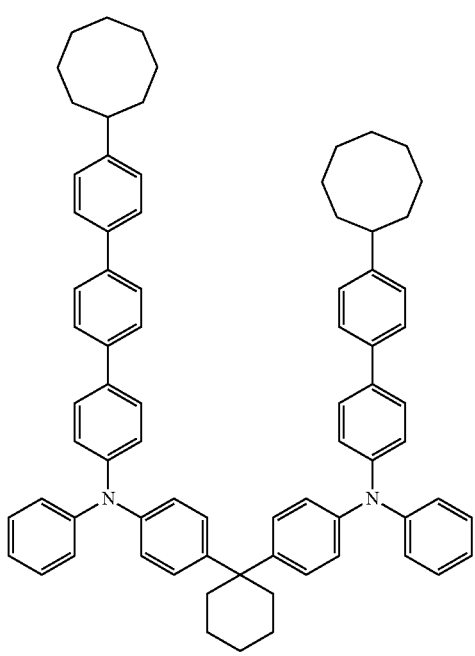

(131)
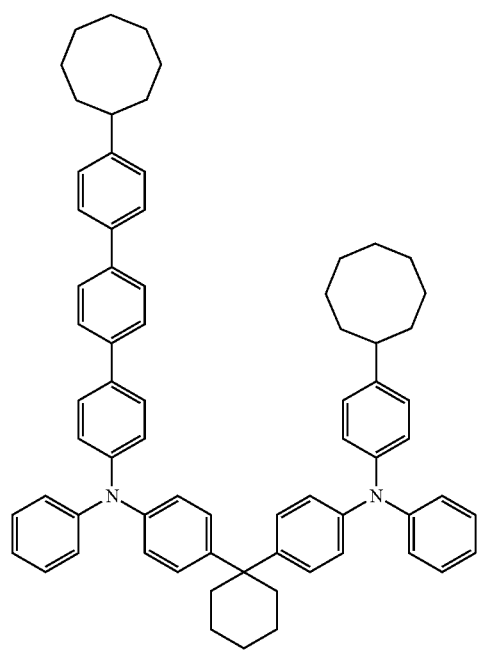
(132)
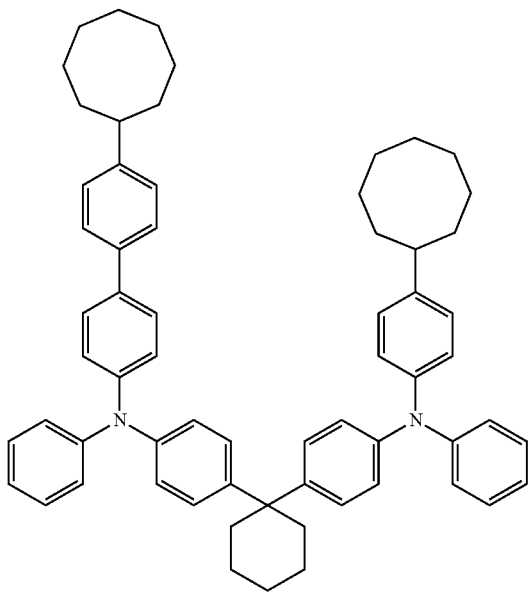
[Chemical Formulae 20]
(133)
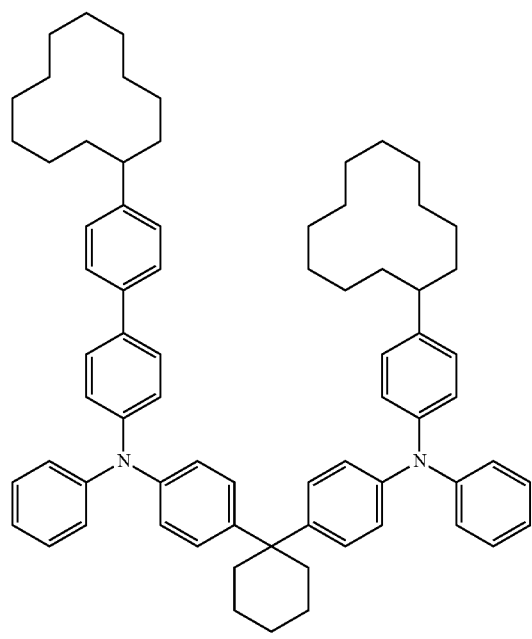
(134)
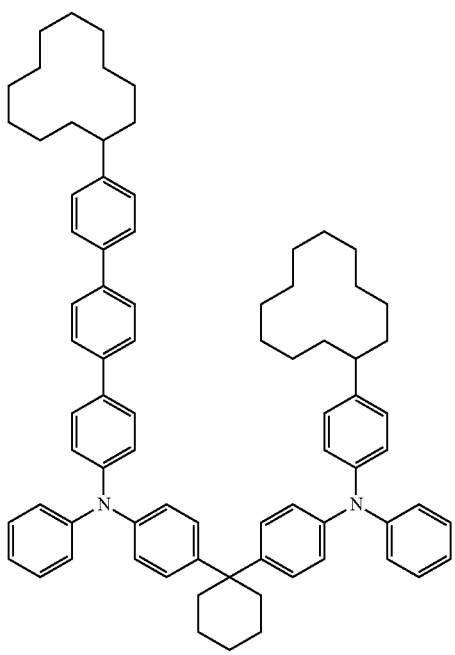

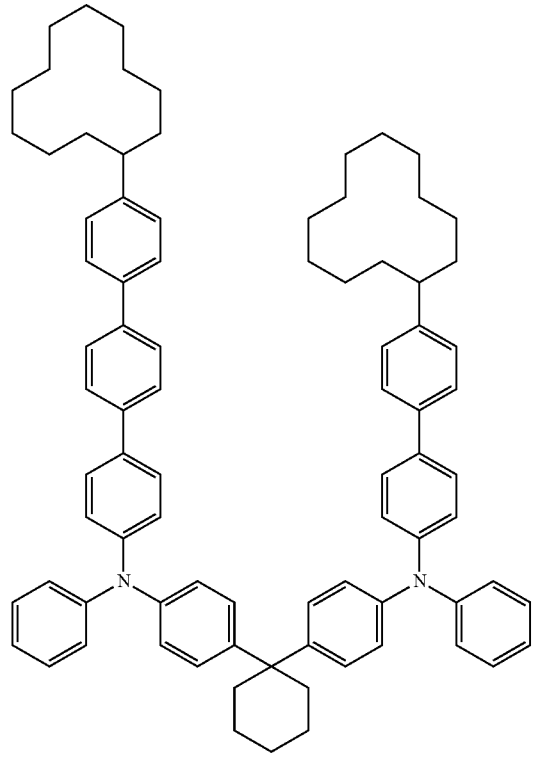
(135)
[Chemical Formulae 21]
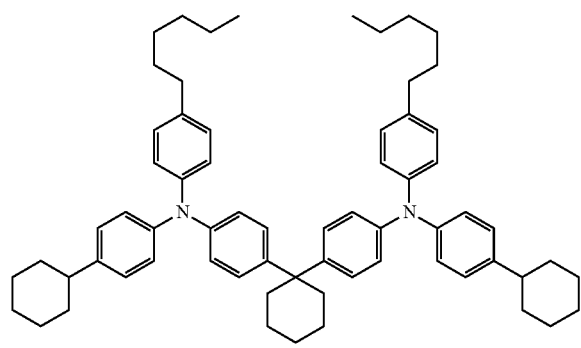
(136)
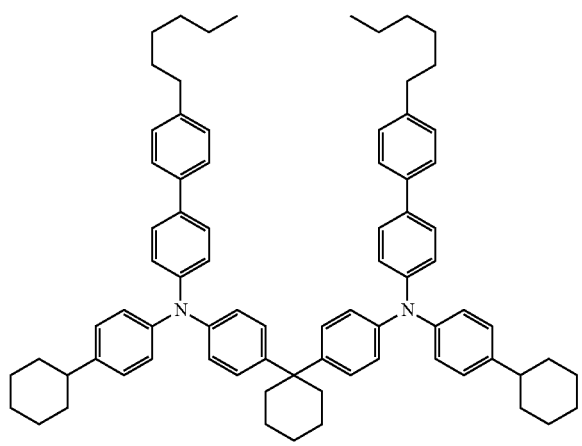
(137)

-continued
(138)
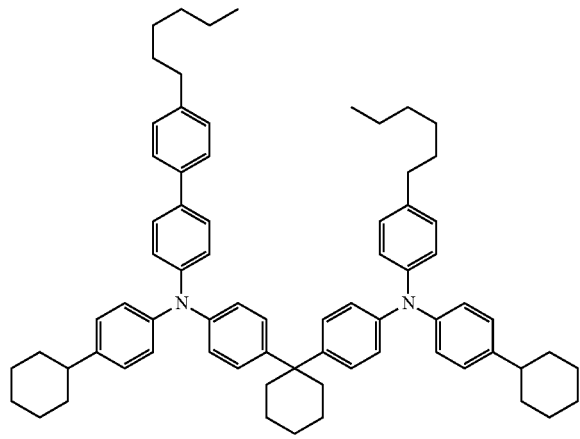
(139)
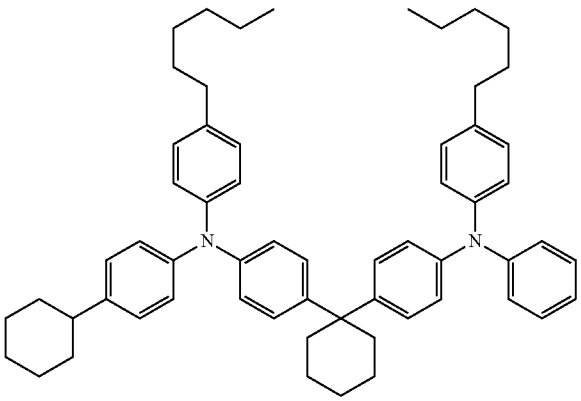
(140)
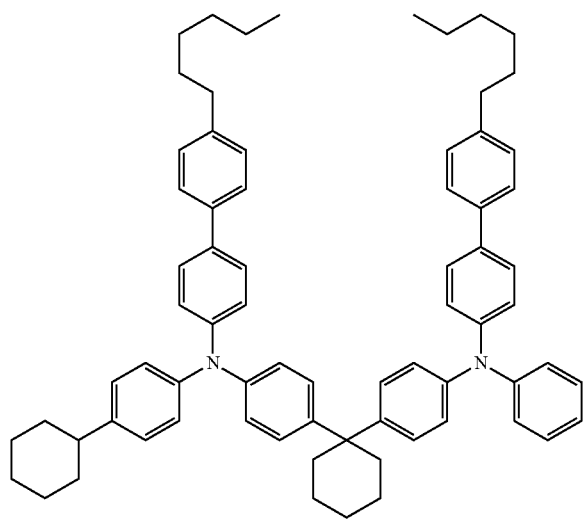
(141)
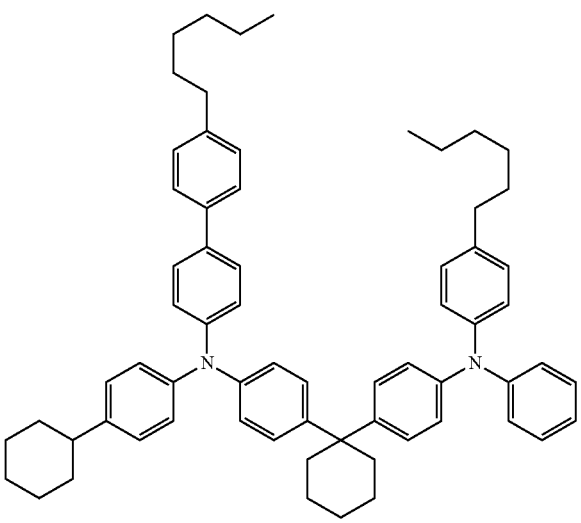
[Chemical Formulae 22]
(142)
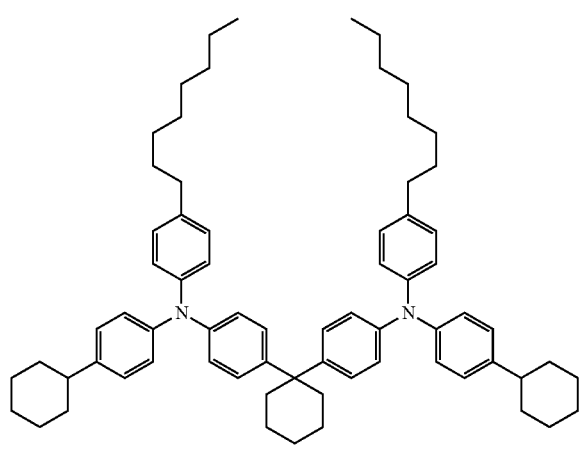
(143)
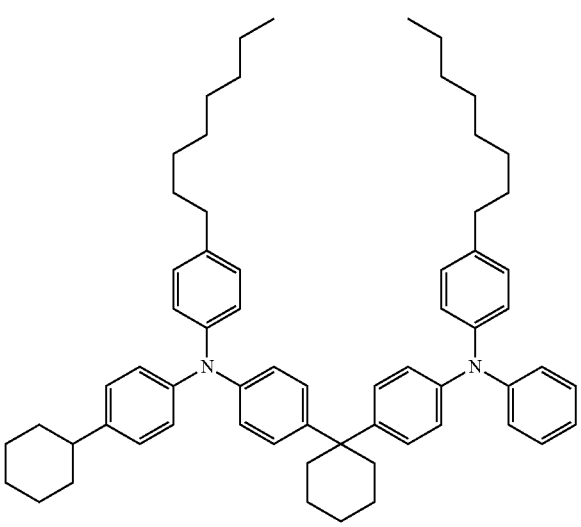

(144)
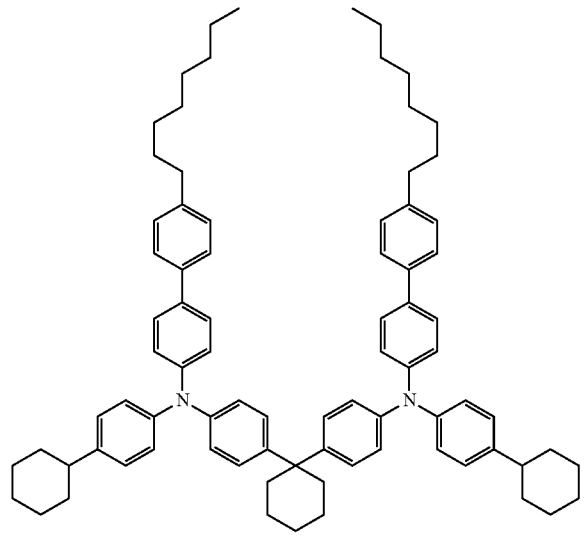
(145)
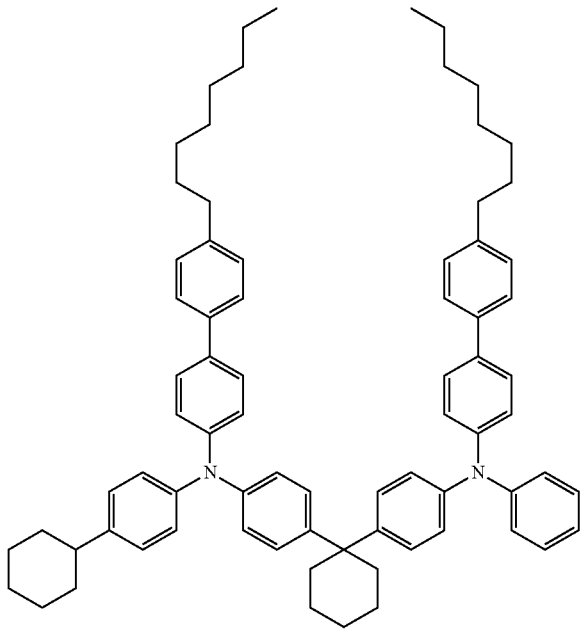
(146)
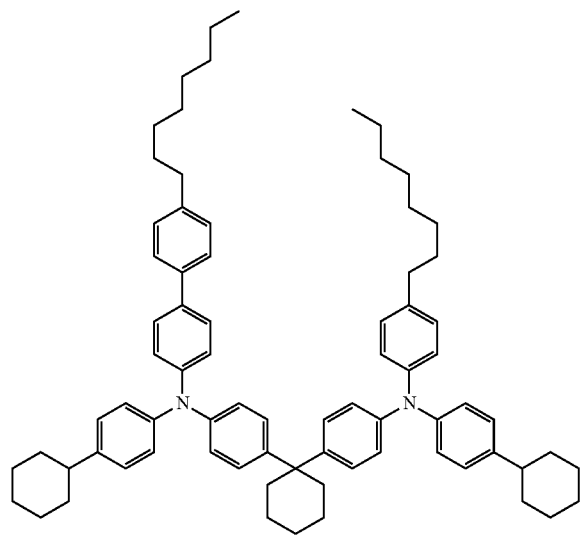
(147)
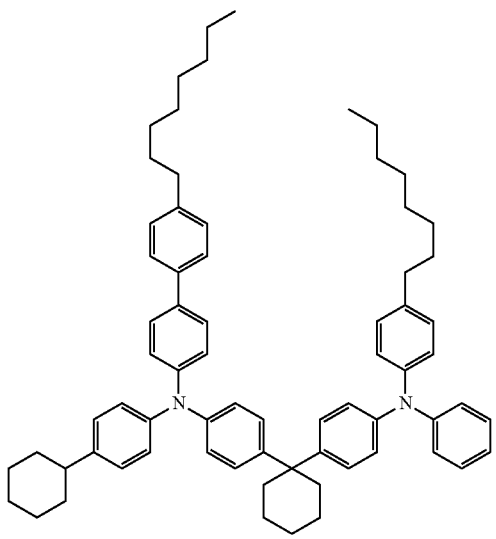

[Chemical Formulae 23]
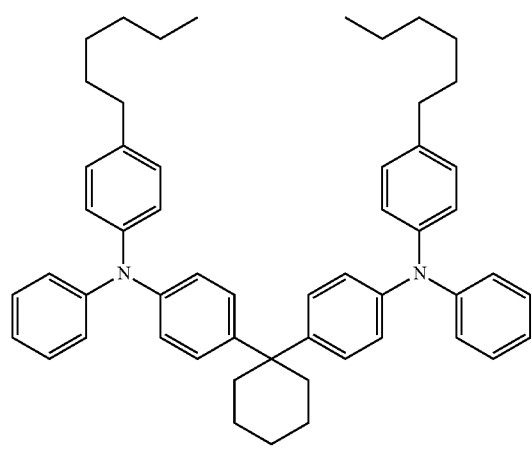
(148)
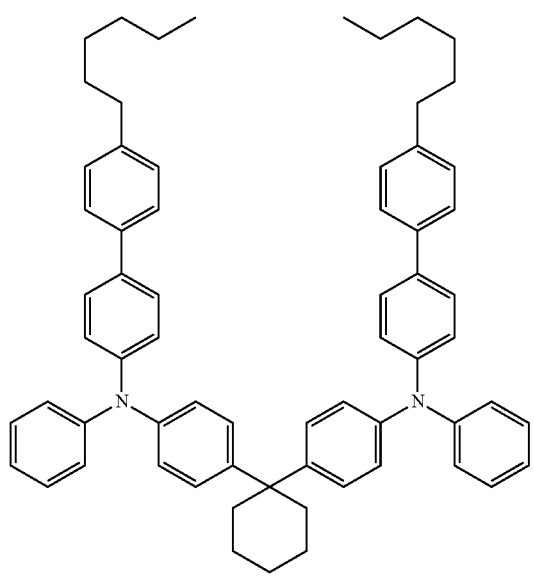
(149)
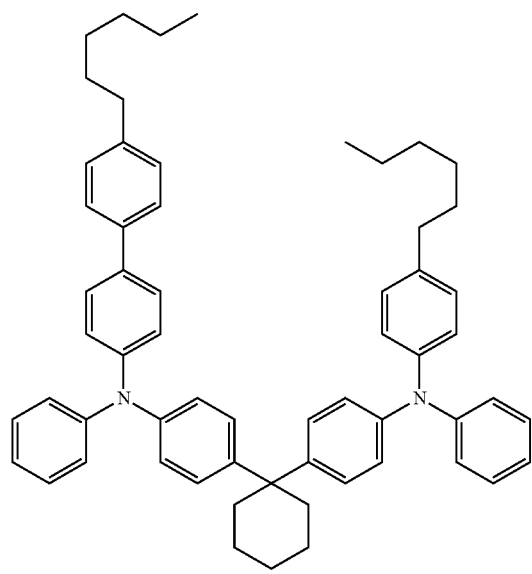
(150)
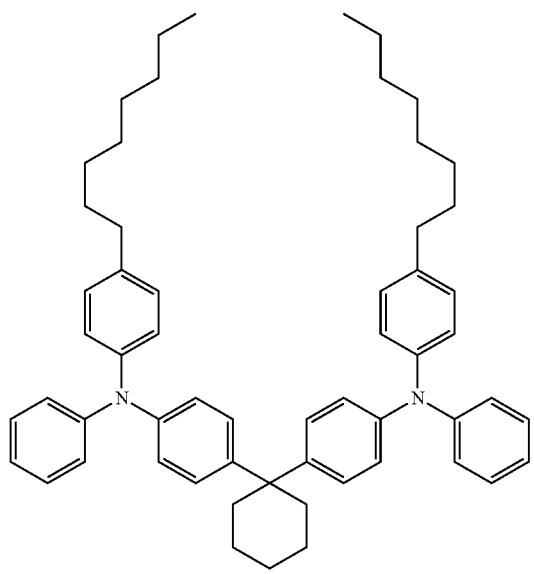
(151)

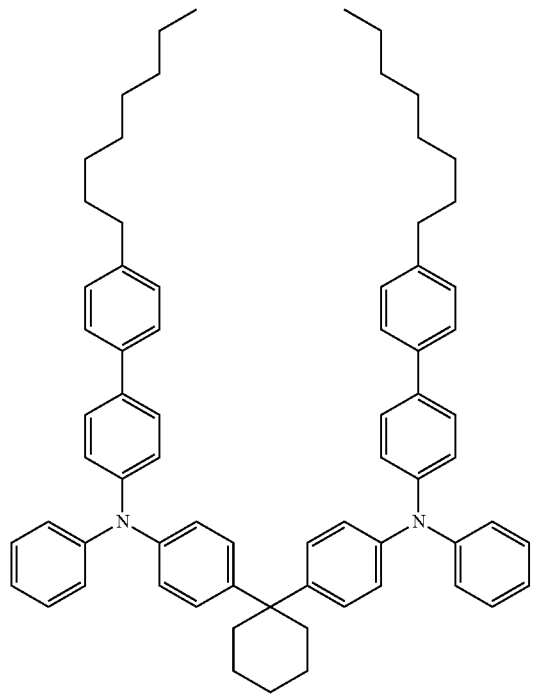

(152)

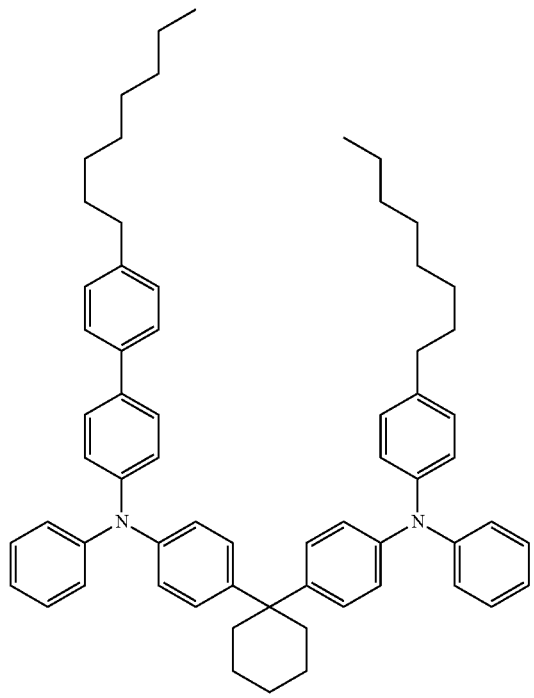

(153)

Next, an example of a method for synthesizing the organic compound of one embodiment of the present invention represented by the following general formula (G1) will be described.

[Chemical Formula 24]

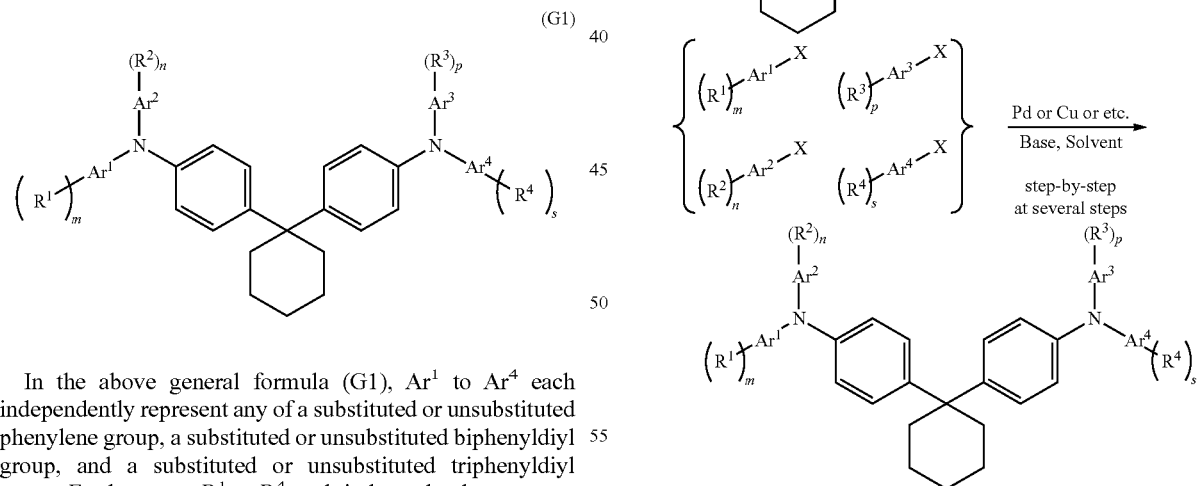

(G1)

In the above general formula (G1), $Ar^1$ to $Ar^4$ each independently represent any of a substituted or unsubstituted phenylene group, a substituted or unsubstituted biphenyldiyl group, and a substituted or unsubstituted triphenyldiyl group. Furthermore, $R^1$ to $R^4$ each independently represent a saturated hydrocarbon group having 5 to 12 carbon atoms or a substituted or unsubstituted cyclic saturated hydrocarbon group having 5 to 12 carbon atoms. In addition, m, n, p, and s each independently represent an integer of 1 to 3.

The organic compound represented by the above general formula (G1) can be synthesized by coupling 1,1-bis(4-aminophenyl)cyclohexane and an organic halide, using a metal catalyst, a metal, or a metal compound in the presence of a base, as shown in the following synthesis scheme.

In the above synthesis scheme, $Ar^1$ to $Ar^4$ each independently represent any of a substituted or unsubstituted phenylene group, a substituted or unsubstituted biphenyldiyl group, and a substituted or unsubstituted triphenyldiyl group. Furthermore, $R^1$ to $R^4$ each independently represent a saturated hydrocarbon group having 5 to 12 carbon atoms or a substituted or unsubstituted cyclic saturated hydrocarbon group having 5 to 12 carbon atoms. In addition, m, n, p, and s each independently represent an integer of 1 to 3.

In the case where the above synthesis scheme is performed as a Buchwald-Hartwig reaction, X represents halogen or a triflate group. As the halogen, iodine, bromine, or chlorine is preferred. In this reaction, a palladium catalyst including a palladium complex or a palladium compound such as bis(dibenzylideneacetone)palladium(0) or allylpalladium(II) chloride dimer and a ligand that coordinates to the palladium complex or the palladium compound, such as tri(tert-butyl)phosphine, di-tert-butyl(1-methyl-2,2-diphenylcyclopropyl)phosphine, or tricyclohexylphosphine, is used. Examples of the base include organic bases such as sodium tert-butoxide, inorganic bases such as a potassium carbonate, and the like. In the case where a solvent is used, toluene, xylene, 1,3,5-trimethylbenzenebenzene, or the like can be used.

When the above synthesis scheme is performed as the Ullmann reaction, X represents halogen. As the halogen, iodine, bromine, or chlorine is preferred. As a catalyst, copper or a copper compound is used. Note that copper(I) iodide or copper(II) acetate is preferably used. Examples of the base used include an inorganic base such as potassium carbonate. As a solvent, 1,3-dimethyl-3,4,5,6-tetrahydro-2(1H)-pyrimidinone (DMPU), N-methyl-2-pyrrolidone (NMP), toluene, xylene, 1,3,5-trimethylbenzene, or the like is used. However, the solvent is not limited to the above. In the Ullmann reaction, when the reaction temperature is 100° C. or higher, an objective substance can be obtained in a shorter time in a higher yield; therefore, it is preferable to use DMPU, NMP, or 1,3,5-trimethylbenzene each having a high boiling point. A higher reaction temperature of 150° C. or higher is further preferred, and accordingly, DMPU is further preferably used.

In the above manner, the organic compound represented by the general formula (G1) can be synthesized.

Embodiment 2

FIG. 1 illustrates a light-emitting device of one embodiment of the present invention. The light-emitting device of one embodiment of the present invention includes a first electrode 101, a second electrode 102, and an EL layer 103, and the organic compound described in Embodiment 1 is used for the EL layer.

The EL layer 103 includes a light-emitting layer 113 and may also include a hole-injection layer 111 and/or a hole-transport layer 112. The light-emitting layer 113 includes a light-emitting material, and light is emitted from the light-emitting material in the light-emitting device of one embodiment of the present invention. The light-emitting layer 113 may include a host material and other materials. The organic compound of one embodiment of the present invention described in Embodiment 1 may be included in any of the light-emitting layer 113, the hole-transport layer 112, and the hole-injection layer 111; alternatively, the organic compound may be included in all of them.

Note that FIG. 1 additionally illustrates an electron-transport layer 114 and an electron-injection layer 115; however, the structure of the light-emitting device is not limited thereto.

The organic compound exhibits a good hole-transport property and thus is effectively used for the hole-transport layer 112. Furthermore, a mixed film of the organic compound of one embodiment of the present invention and an acceptor substance can be used as the hole-injection layer 111.

In addition, the organic compound of one embodiment of the present invention can be used as a host material. Furthermore, the hole-transport material and an electron-transport material may be deposited by co-evaporation so that an exciplex is formed of the electron-transport material and the hole-transport material. The exciplex having an appropriate emission wavelength allows efficient energy transfer to the light-emitting material, achieving a light-emitting device with a high efficiency and a long lifetime.

Since the organic compound of one embodiment of the present invention has a low refractive index, the light-emitting device using the organic compound in its EL layer can have high external quantum efficiency.

Next, examples of specific structures and materials of the above-described light-emitting device will be described. As described above, the light-emitting device of one embodiment of the present invention includes, between the pair of electrodes of the first electrode 101 and the second electrode 102, the EL layer 103 including a plurality of layers; the EL layer 103 includes the organic compound disclosed in Embodiment 1 in any of the layers.

The first electrode 101 is preferably formed using any of metals, alloys, and conductive compounds with a high work function (specifically, higher than or equal to 4.0 eV), mixtures thereof, and the like. Specific examples include indium oxide-tin oxide (ITO: indium tin oxide), indium oxide-tin oxide containing silicon or silicon oxide, indium oxide-zinc oxide, and indium oxide containing tungsten oxide and zinc oxide (IWZO). Such conductive metal oxide films are usually formed by a sputtering method, but may be formed by application of a sol-gel method or the like. In an example of the formation method, indium oxide-zinc oxide is deposited by a sputtering method using a target obtained by adding 1 to 20 wt % of zinc oxide to indium oxide. Furthermore, a film of indium oxide containing tungsten oxide and zinc oxide (IWZO) can be formed by a sputtering method using a target in which tungsten oxide and zinc oxide are added to indium oxide at 0.5 to 5 wt % and 0.1 to 1 wt %, respectively. Alternatively, gold (Au), platinum (Pt), nickel (Ni), tungsten (W), chromium (Cr), molybdenum (Mo), iron (Fe), cobalt (Co), copper (Cu), palladium (Pd), nitride of a metal material (e.g., titanium nitride), or the like can be used. Graphene can also be used. Note that when a composite material described later is used for a layer that is in contact with the first electrode 101 in the EL layer 103, an electrode material can be selected regardless of its work function.

Although the EL layer 103 preferably has a stacked-layer structure, there is no particular limitation on the stacked-layer structure, and various layers such as a hole-injection layer, a hole-transport layer, an electron-transport layer, an electron-injection layer, a carrier-blocking layer, an exciton-blocking layer, and a charge-generation layer can be employed. Two kinds of stacked-layer structure of the EL layer 103 are described: the structure illustrated in FIG. 1(A), which includes the electron-transport layer 114 and the electron-injection layer 115 in addition to the hole-injection layer 111, the hole-transport layer 112, and the light-emitting layer 113; and the structure illustrated in FIG. 1(B), which includes the electron-transport layer 114, the electron-injection layer 115, and a charge-generation layer 116 in addition to the hole-injection layer 111, the hole-transport layer 112, and the light-emitting layer 113. Materials for forming each layer will be specifically described below.

The hole-injection layer 111 contains a substance having an acceptor property. Either an organic compound or an inorganic compound can be used as the substance having an acceptor property.

As the substance having an acceptor property, it is possible to use a compound having an electron-withdrawing group (a halogen group or a cyano group); for example, compounds having an electron-withdrawing group such as 7,7,8,8-tetracyano-2,3,5,6-tetrafluoroquinodimethane (abbreviation: $F_4$-TCNQ), 3,6-difluoro-2,5,7,7,8,8-hexacyano-quinodimethane, chloranil, 2,3,6,7,10,11-hexacyano-1,4,5,8,9,12-hexaazatriphenylene (abbreviation: HAT-CN), and 1,3,4,5,7,8-hexafluorotetracyano-naphthoquinodimethane (abbreviation: F6-TCNNQ) can be used. As an organic compound with an acceptor property, a compound in which electron-withdrawing groups are bonded to a condensed aromatic ring having a plurality of heteroatoms, such as HAT-CN, is particularly preferable because it is thermally stable. A [3]radialene derivative having an electron-withdrawing group (in particular, a cyano group or a halogen group such as a fluoro group) has a very high electron-accepting property and thus is preferable. Specific examples include α,α',α''-1,2,3-cyclopropanetriylidenetris[4-cyano-2,3,5,6-tetrafluorobenzeneacetonitrile], α,α',α''-1,2,3-cyclopropanetriylidenetris[2,6-dichloro-3,5-difluoro-4-(trifluoromethyl)benzeneacetonitrile], and α,α',α''-1,2,3-cyclopropanetriylidenetris[2,3,4,5,6-pentafluorobenzeneacetonitrile]. As the substance having an acceptor property, molybdenum oxide, vanadium oxide, ruthenium oxide, tungsten oxide, manganese oxide, or the like can be used, other than the above-described organic compounds. Alternatively, the hole-injection layer 111 can be formed using a phthalocyanine-based complex compound such as phthalocyanine (abbreviation: $H_2Pc$) and copper phthalocyanine (CuPC), an aromatic amine compound such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS). The substance having an acceptor property can extract electrons from an adjacent hole-transport layer (or hole-transport material) by the application of an electric field.

Alternatively, a composite material in which a substance having a hole-transport property contains an acceptor substance can be used for the hole-injection layer 111. By using a composite material in which a substance having a hole-transport property contains an acceptor substance, a material used to form an electrode can be selected regardless of its work function. In other words, besides a material having a high work function, a material having a low work function can also be used for the first electrode 101. Examples of the acceptor substance include an organic compound having an acceptor property, such as 7,7,8,8-tetracyano-2,3,5,6-tetrafluoroquinodimethane (abbreviation: F4-TCNQ), chloranil, or 1,3,4,5,7,8-hexafluorotetracyano-naphthoquinodimethane (abbreviation: F6-TCNNQ), and a transition metal oxide. In addition, oxides of metals belonging to Group 4 to Group 8 of the periodic table can be used. As the oxide of a metal belonging to Group 4 to Group 8 in the periodic table, vanadium oxide, niobium oxide, tantalum oxide, chromium oxide, molybdenum oxide, tungsten oxide, manganese oxide, rhenium oxide, or the like is preferably used because their electron-accepting property is high. Among these oxides, molybdenum oxide is particularly preferable because it is stable in the air, has a low hygroscopic property, and is easy to handle.

As the substance with a hole-transport property used for the composite material, any of a variety of organic compounds such as aromatic amine compounds, carbazole derivatives, aromatic hydrocarbons, and high molecular compounds (e.g., oligomers, dendrimers, or polymers) can be used. Note that the substance with a hole-transport property used for the composite material preferably has a hole mobility of $10^{-6}$ cm$^2$/Vs or higher. Organic compounds which can be used as the substance with a hole-transport property in the composite material are specifically given below.

Examples of the aromatic amine compounds that can be used for the composite material include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and 1,1-bis-(4-bis(4-methyl-phenyl)-amino-phenyl)-cyclohexane (abbreviation: TAPC). Specific examples of the carbazole derivative include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(10-phenylanthracen-9-yl)phenyl]-9H-carbazole (abbreviation: CzPA), and 1,4-bis[4-(N-carbazolyl)phenyl]-2,3,5,6-tetraphenylbenzene. Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-di phenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, and 2,5,8,11-tetra(tert-butyl)perylene. Other examples include pentacene and coronene. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA). Note that the organic compound of one embodiment of the present invention can also be used. In this case, F6-TCNNQ is preferably used as the acceptor substance.

Other examples include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD).

The organic compound of one embodiment of the present invention disclosed in Embodiment 1 is also a material having a hole-transport property and can be suitably used as a substance with a hole-transport property used for the composite material. A layer with a low refractive index can be formed in the EL layer 103 with the use of the organic compound of one embodiment of the present invention, leading to higher external quantum efficiency of the light-emitting device.

Note that mixing the above composite material with a fluoride of an alkali metal or an alkaline earth metal (the proportion of fluorine atoms in a layer using the mixed material is preferably greater than or equal to 20%) can lower the refractive index of the layer. This also enables a layer with a low refractive index to be formed in the EL layer 103, leading to higher external quantum efficiency of the light-emitting device.

The formation of the hole-injection layer 111 can improve the hole-injection property, which allows the light-emitting device to be driven at a low voltage. In addition, the organic compound having an acceptor property is easy to use because it is easily deposited by vapor deposition.

The hole-transport layer 112 contains a material having a hole-transport property. The material having a hole-transport property preferably has a hole mobility of $1 \times 10^{-6}$ cm$^2$/Vs or more. The hole-transport layer 112 preferably includes the organic compound of one embodiment of the present invention. When the organic compound described in Embodiment 1 is included in the hole-transport layer 112, a layer with a low refractive index can be formed in the EL layer 103, leading to higher external quantum efficiency of the light-emitting device.

Examples of the material having a hole-transport property include compounds having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]-spiro-9,9'-bifluoren-2-amine (abbreviation: PCBASF); compounds having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compound having an aromatic amine skeleton and the compound having a carbazole skeleton are preferable because these compounds are highly reliable and have high hole-transport properties to contribute to a reduction in driving voltage. Note that any of the substances given as examples of the material having a hole-transport property which is used in the composite material for the hole-injection layer 111 can also be suitably used as the material included in the hole-transport layer 112.

The light-emitting layer 113 is a layer containing the host material and the light-emitting material. The light-emitting material may be fluorescent substances, phosphorescent substances, substances exhibiting thermally activated delayed fluorescence (TADF), or other light-emitting materials. Furthermore, it may be a single layer or be formed of a plurality of layers including different light-emitting materials.

Examples of a material that can be used as a fluorescent substance in the light-emitting layer 113 are as follows. Fluorescent substances other than those given below can also be used.

The examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-diphenyl-N,N'-bis[4-(9-phenyl-9H-fluoren-9-yl)phenyl]pyrene-1,6-diamine (abbreviation: 1,6FLPAPrn), N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N",N",N'",N'"-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6- bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), and N,N'-diphenyl-N,N'-(1,6-pyrene-diyl)bis[(6-phenylbenzo[b]naphtho[1,2-d]furan)-8-amine] (abbreviation:1,6BnfAPrn-03). Condensed aromatic diamine compounds typified by pyrenediamine compounds such as 1,6FLPAPrn, 1,6mMemFLPAPrn, and 1,6BnfAPrn-03 are particularly preferable because of their high hole-trapping properties, high emission efficiency, and high reliability.

Examples of a material that can be used as a phosphorescent substance in the light-emitting layer 113 are as follows.

The examples are as follows: an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and an organometallic iridium complex in which a phenylpyridine derivative having an electron-withdrawing group is a ligand, such as bis[2-(4',6'-difluorophenyl)pyridinato-N,C$^2$]iridium(III) tetrakis(1-pyrazolyl)borate (abbreviation: FIr6), bis[2-(4',6'-difluorophenyl)pyridinato-N,C$^2$]iridium(III) picolinate (abbreviation: FIrpic), bis{2-[3',5'-bis(trifluoromethyl)phenyl]pyridinato-N,C$^2$}iridium(III) picolinate (abbreviation: [Ir(CF$_3$ppy)$_2$(pic)]), and bis[2-(4',6'-difluorophenyl)pyridinato-N,C$^2$]iridium(III) acetylacetonate (abbreviation: FIracac). These compounds emit blue phosphorescence and have an emission peak at 440 nm to 520 nm.

Other examples include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C$^{2'}$)iridium(III) (abbreviation: [Ir(ppy)$_3$]), bis(2-phenylpyridinato-N,C$^{2-}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and a rare earth metal complex such as tris(acetylacetonato) (monophenanthroline)terbium(III) (abbreviation: [Tb(acac)$_3$(Phen)]). These are mainly compounds that emit green phosphorescence and have an emission peak at 500 nm to 600 nm. Note that organometallic iridium complexes having a pyrimidine skeleton have distinctively high reliability and emission efficiency and thus are particularly preferable.

Other examples include organometallic iridium complexes having a pyrimidine skeleton, such as (diisobutyryl-methanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato(dipivaloylmethanato)iridium(III) (abbreviation: [Ir(d1npm)$_2$(dpm)]); organometallic iridium complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having a pyridine skeleton, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrinplatinum(II) (abbreviation: [PtOEP]); and rare earth metal complexes such as tris(1,3-diphenyl-1,3-propanedionato) (monophenanthroline)europium(III) (abbreviation: [Eu(DBM)$_3$(Phen)]) and tris[1-(2-thenoyl)-3,3,3-trifluoroacetonato(monophenanthroline)europium(III) (abbreviation: [Eu(TTA)$_3$(Phen)]). These compounds emit red phosphorescence having an emission peak at 600 nm to 700 nm. Furthermore, the organometallic iridium complexes having a pyrazine skeleton can provide red light emission with favorable chromaticity.

Besides the above-described phosphorescent compounds, other known phosphorescent materials may be selected and used.

Examples of the TADF material include a fullerene, a derivative thereof, an acridine, a derivative thereof, and an eosin derivative. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$OEP), which are represented by the following structural formulae.

[Chemical Formulae 26]
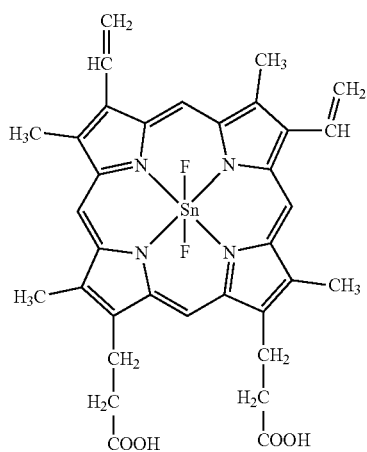
SnF$_2$(Proto IX)
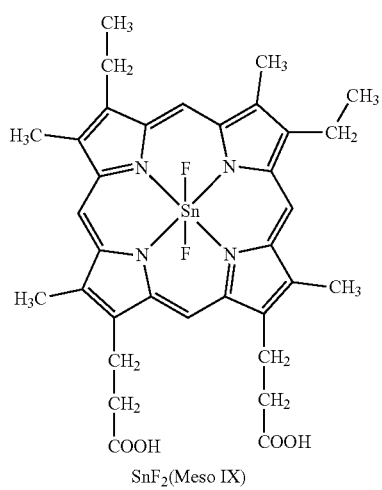
SnF$_2$(Meso IX)
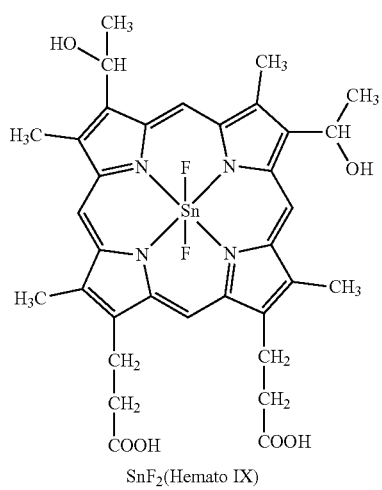
SnF$_2$(Hemato IX)
-continued
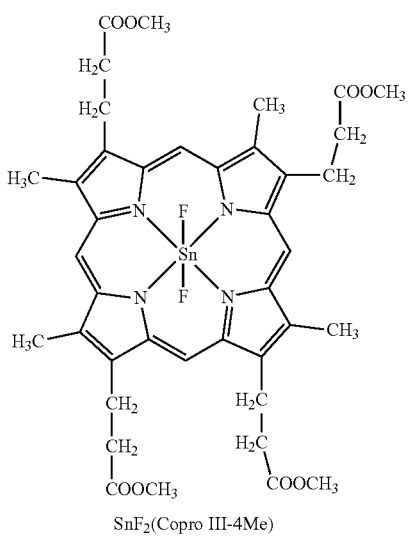
SnF$_2$(Copro III-4Me)
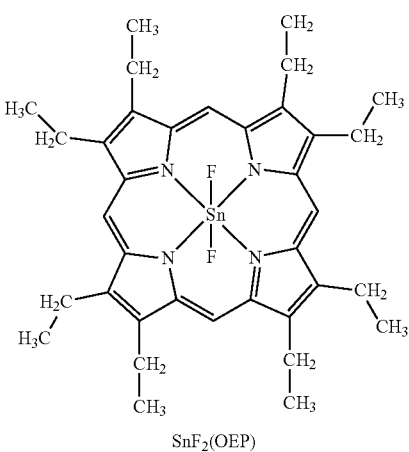
SnF$_2$(OEP)
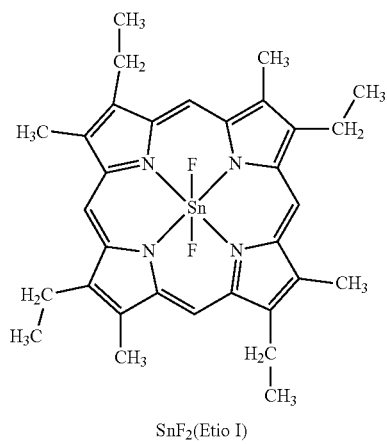
SnF$_2$(Etio I)

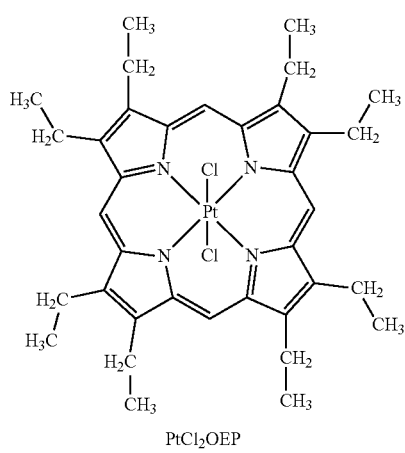

PtCl₂OEP

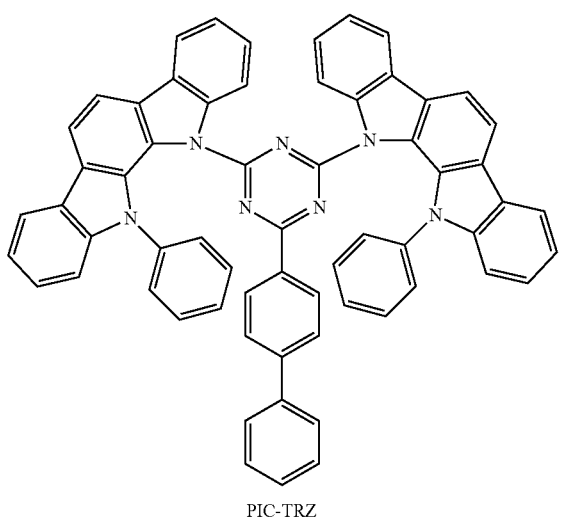

PIC-TRZ

Alternatively, a heterocyclic compound having both of a π-electron rich heteroaromatic ring and a π-electron deficient heteroaromatic ring that is represented by the following structural formulae, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 9-[4-(4,6-diphenyl-1,3,5-triazin-2-yl)phenyl]-9'-phenyl-9H,9'H-3,3'-bicarbazole (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5, 10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DP S), or 10-phenyl-10H,10'H-spiro[acridin-9,9'-anthracen]-10'-one (abbreviation: ACRSA) can be used. The heterocyclic compound is preferable because of having both a high electron-transport property and a high hole-transport property owing to a π-electron rich heteroaromatic ring and a π-electron deficient heteroaromatic ring. Note that a substance in which the π-electron rich heteroaromatic ring and the π-electron deficient heteroaromatic ring are directly bonded to each other is particularly preferable because the donor property of the π-electron rich heteroaromatic ring and the acceptor property of the π-electron deficient heteroaromatic ring are both increased and the energy difference between the S1 level and the T1 level becomes small, so that thermally activated delayed fluorescence can be obtained with high efficiency. Note that an aromatic ring to which an electron-withdrawing group such as a cyano group is bonded may be used instead of the π-electron deficient heteroaromatic ring.

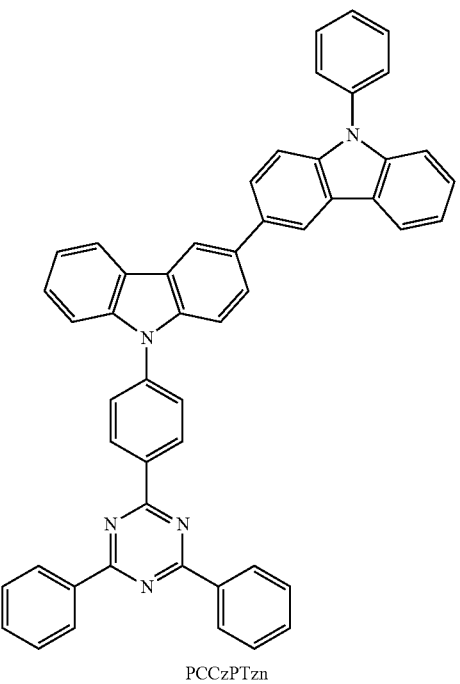

PCCzPTzn

-continued

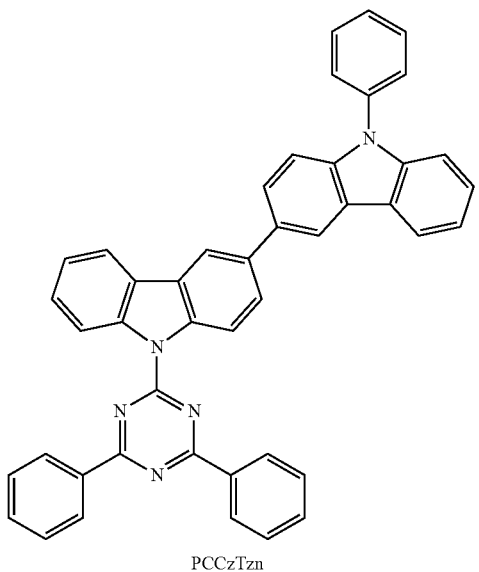

PCCzTzn

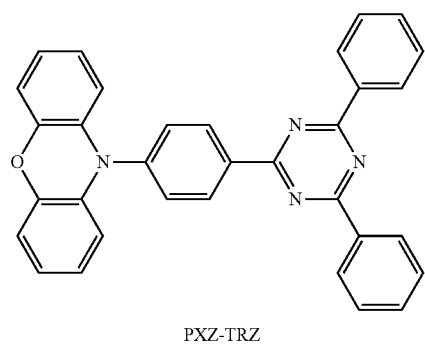

PXZ-TRZ

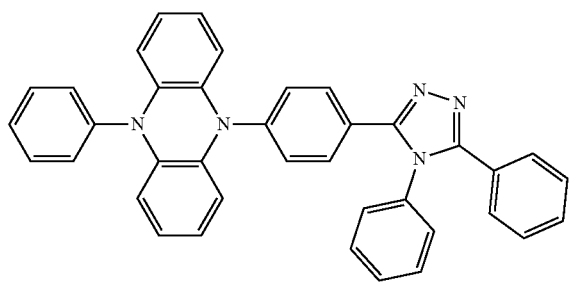

PPZ-3TPT

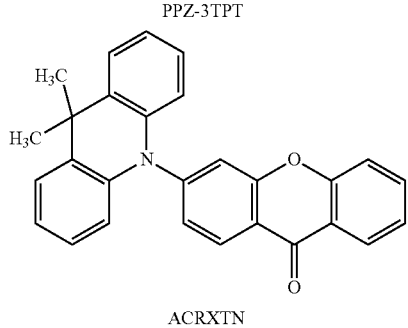

ACRXTN

-continued

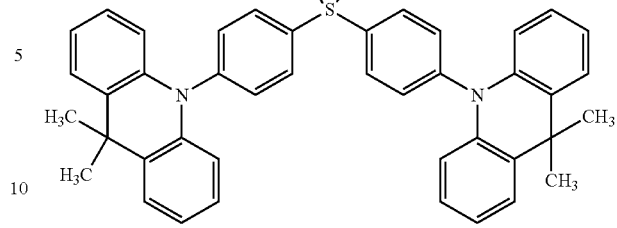

DMAC-DPS

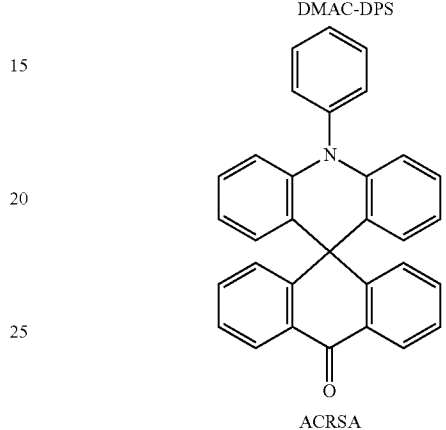

ACRSA

As the host material in the light-emitting layer, a variety of carrier-transport materials such as a material having an electron-transport property and a material having a hole-transport property can be used.

As the material having a hole-transport property, the substances given above as materials having a hole-transport property contained in the hole-transport layer 112 can be suitably used.

As the material having an electron-transport property, for example, a metal complex such as bis(10-hydroxybenzo[h]quinolinato)beryllium(II) (abbreviation: BeBq$_2$), bis(2-methyl-8-quinolinolato) (4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato]zinc(II) (abbreviation: ZnBTZ), a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II), a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II), and a heterocyclic compound having a pyridine skeleton, such as 3,5-bis[3-(9H-carbazol-9-yl)phenyl]pyridine (abbreviation:

35DCzPPy) or 1,3,5-tri[3-(3-pyridyl)-phenyl]benzene (abbreviation: TmPyPB) can be given. Among the above, the heterocyclic compound having a diazine skeleton and the heterocyclic compound having a pyridine skeleton have favorable reliability and thus are preferable. In particular, the heterocyclic compound having a diazine (pyrimidine or pyrazine) skeleton has a high electron-transport property and contributes to a reduction in driving voltage.

In the case where a fluorescent substance is used as the light-emitting material, a material having an anthracene skeleton is favorably used as the host material. The use of a substance having an anthracene skeleton as the host material for the fluorescent substance makes it possible to obtain a light-emitting layer with high emission efficiency and high durability. Most of materials having an anthracene skeleton have a deep HOMO level; therefore, such a material can be preferably used in one embodiment of the present invention. Among the substances having an anthracene skeleton, a substance having a diphenylanthracene skeleton, in particular, a substance having a 9,10-diphenylanthracene skeleton, is chemically stable and thus is preferably used as the host material. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material preferably has a dibenzocarbazole skeleton because the HOMO level thereof is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole or dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), and 9-phenyl-10-{4-(9-phenyl-9H-fluoren-9-yl)biphenyl-4'-yl}anthracene (abbreviation: FLPPA). In particular, CzPA, cgDBCzPA, 2mBnfPPA, and PCzPA are preferably selected because they exhibit excellent characteristics.

Note that the host material may be a mixture of a plurality of kinds of substances; in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

An exciplex may be formed of these mixed materials. When these mixed materials are selected so as to form an exciplex that exhibits light emission whose wavelength overlaps with the wavelength on a lowest-energy-side absorption band of the light-emitting material, energy can be transferred smoothly and light emission can be obtained efficiently, which is preferable. The use of such a structure is preferable because the driving voltage can also be reduced.

An electron-transport layer 114 contains a substance having an electron-transport property. As the substance having an electron-transport property, it is possible to use any of the above-listed substances having electron-transport properties that can be used as the host material.

A layer containing an alkali metal, an alkaline earth metal, or a compound thereof such as lithium fluoride (LiF), cesium fluoride (CsF), or calcium fluoride ($CaF_2$) may be provided as the electron-injection layer 115 between the electron-transport layer 114 and the second electrode 102. For example, an electride or a layer that is formed using a substance having an electron-transport property and that includes an alkali metal, an alkaline earth metal, or a compound thereof can be used as the electron-injection layer 115. Examples of the electride include a substance in which electrons are added at high concentration to calcium oxide-aluminum oxide.

Note that as the electron-injection layer 115, it is possible to use a layer containing a substance that has an electron-transport property (preferably an organic compound having a bipyridine skeleton) and contains a fluoride of the alkali metal or the alkaline earth metal at a concentration higher than that at which the electron-injection layer 115 becomes in a microcrystalline state (50 wt % or higher). Since the layer has a low refractive index, a light-emitting device including the layer can have high external quantum efficiency.

Figure 1B:
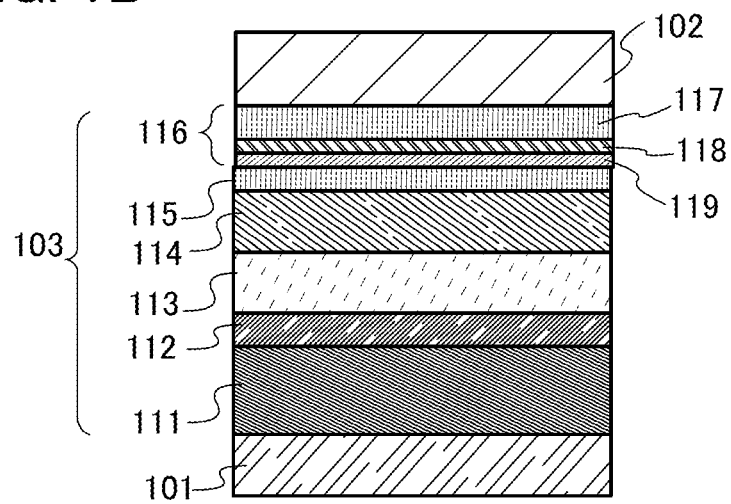

Instead of the electron-injection layer 115, a charge-generation layer 116 may be provided (FIG. 1(B)). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential is applied to the p-type layer 117, electrons are injected into the electron-transport layer 114 and holes are injected into the second electrode 102 serving as a cathode; thus, the light-emitting device operates. Since the organic compound of one embodiment of the present invention has a low refractive index, using the organic compound for the p-type layer 117 enables the light-emitting device to have high external quantum efficiency.

Note that the charge-generation layer 116 preferably includes an electron-relay layer 118 and/or an electron-injection buffer layer 119 in addition to the p-type layer 117.

The electron-relay layer 118 includes at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the acceptor substance in the p-type layer 117 and the LUMO level of a substance contained in a layer of the electron-transport layer 114 that is in contact with the charge-generation layer 116. As a specific value of the energy level, the LUMO level of the substance having an electron-transport property in the electron-relay layer 118 is preferably higher than or equal to −5.0 eV, more preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (e.g., an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)). As the substance having an electron-transport property, a material similar to the above-described material for the electron-transport layer 114 can be used.

For the second electrode 102, a metal, an alloy, an electrically conductive compound, or a mixture thereof each having a low work function (specifically, lower than or equal to 3.8 eV) or the like can be used. Specific examples of such a cathode material are elements belonging to Group 1 or Group 2 of the periodic table, such as alkali metals (e.g., lithium (Li) and cesium (Cs)), magnesium (Mg), calcium (Ca), and strontium (Sr), alloys containing these elements (e.g., MgAg and AlLi), rare earth metals such as europium (Eu) and ytterbium (Yb), and alloys containing these rare earth metals. However, when the electron-injection layer is provided between the second electrode 102 and the electron-transport layer, for the second electrode 102, a variety of conductive materials such as Al, Ag, ITO, or indium oxide-tin oxide containing silicon or silicon oxide can be used regardless of the work function. Films of these conductive materials can be formed by a dry process such as a vacuum evaporation method or a sputtering method, an ink-jet method, a spin coating method, or the like. Alternatively, a wet process using a sol-gel method or a wet process using a paste of a metal material may be employed.

Furthermore, any of a variety of methods can be used for forming the EL layer 103, regardless of a dry method or a wet method. For example, a vacuum evaporation method, a gravure printing method, an offset printing method, a screen printing method, an ink-jet method, a spin coating method, or the like may be used.

Different methods may be used to form the electrodes or the layers described above.

The structure of the layers provided between the first electrode 101 and the second electrode 102 is not limited to the above-described structure. Preferably, a light-emitting region where holes and electrons recombine is positioned away from the first electrode 101 and the second electrode 102 so as to prevent quenching due to the proximity of the light-emitting region and a metal used for electrodes and carrier-injection layers.

Furthermore, in order that transfer of energy from an exciton generated in the light-emitting layer can be suppressed, preferably, the hole-transport layer and the electron-transport layer which are in contact with the light-emitting layer 113, particularly a carrier-transport layer closer to the recombination region in the light-emitting layer 113, are formed using a substance having a wider band gap than the light-emitting material of the light-emitting layer or the light-emitting material included in the light-emitting layer.

Next, an embodiment of a light-emitting device with a structure where a plurality of light-emitting units is stacked (also referred to as a stacked-type device or a tandem device) will be described with reference to FIG. 1(C). This light-emitting device is a light-emitting device including a plurality of light-emitting units between an anode and a cathode. One light-emitting unit has substantially the same structure as that of the EL layer 103, which is illustrated in FIG. 1(A). In other words, the light-emitting device illustrated in FIG. 1(C) can be called a light-emitting device including a plurality of light-emitting units, and the light-emitting device illustrated in FIG. 1(A) or FIG. 1(B) can be called a light-emitting device including one light-emitting unit.

Figure 1C:
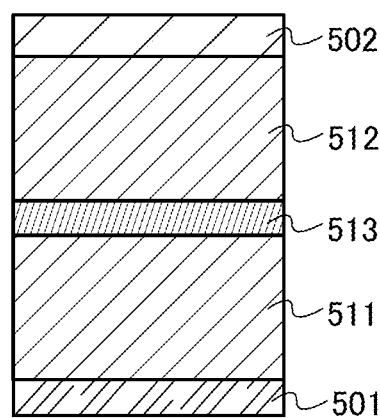

In FIG. 1(C), a first light-emitting unit 511 and a second light-emitting unit 512 are stacked between an anode 501 and a cathode 502, and a charge-generation layer 513 is provided between the first light-emitting unit 511 and the second light-emitting unit 512. The anode 501 and the cathode 502 correspond, respectively, to the first electrode 101 and the second electrode 102 illustrated in FIG. 1(A), and the materials given in the description for FIG. 1(A) can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the anode 501 and the cathode 502. That is, in FIG. 1(C), the charge-generation layer 513 injects electrons into the first light-emitting unit 511 and holes into the second light-emitting unit 512 when a voltage is applied so that the potential of the anode becomes higher than the potential of the cathode.

The charge-generation layer 513 preferably has a structure similar to that of the charge-generation layer 116 described with reference to FIG. 1(B). A composite material of an organic compound and a metal oxide has an excellent carrier-injection property and an excellent carrier-transport property; thus, low-voltage driving and low-current driving can be achieved. In the case where the anode-side surface of a light-emitting unit is in contact with the charge-generation layer 513, the charge-generation layer 513 can also function as a hole-injection layer of the light-emitting unit; therefore, a hole-injection layer is not necessarily provided in the light-emitting unit.

In the case where the charge-generation layer 513 includes the electron-injection buffer layer 119, the electron-injection buffer layer 119 functions as the electron-injection layer in the light-emitting unit on the anode side and thus, an electron-injection layer is not necessarily formed in the light-emitting unit on the anode side.

The light-emitting device having two light-emitting units is described with reference to FIG. 1(C); however, one embodiment of the present invention can also be applied to a light-emitting device in which three or more light-emitting units are stacked. With a plurality of light-emitting units partitioned by the charge-generation layer 513 between a pair of electrodes as in the light-emitting device of this embodiment, it is possible to provide a long-life device which can emit light with high luminance at a low current density. A light-emitting apparatus which can be driven at a low voltage and has low power consumption can be provided.

When the emission colors of the light-emitting units are different, light emission of a desired color can be obtained from the light-emitting device as a whole. For example, in a light-emitting device having two light-emitting units, the emission colors of the first light-emitting unit may be red and green and the emission color of the second light-emitting unit may be blue, so that the light-emitting device can emit white light as the whole.

The above-described layers and electrodes such as the EL layer 103, the first light-emitting unit 511, the second light-emitting unit 512, and the charge-generation layer can be formed by a method such as an evaporation method (including a vacuum evaporation method), a droplet discharge method (also referred to as an ink-jet method), a coating method, or a gravure printing method. A low molecular material, a middle molecular material (including an oligomer and a dendrimer), or a high molecular material may be included in the layers and electrodes.

Embodiment 3

In this embodiment, a light-emitting apparatus using the light-emitting device described in Embodiment 2 will be described.

In this embodiment, a light-emitting apparatus fabricated using the light-emitting device described in Embodiment 2 will be described with reference to FIG. 2. Note that FIG. 2(A) is a top view illustrating the light-emitting apparatus, and FIG. 2(B) is a cross-sectional view taken along A-B and C-D in FIG. 2(A). This light-emitting apparatus includes a driver circuit portion (source line driver circuit) 601, a pixel portion 602, and a driver circuit portion (gate line driver circuit) 603, which are for controlling light emission of a light-emitting device and are illustrated with dotted lines. Furthermore, 604 denotes a sealing substrate, 605 denotes a sealant, and the inside surrounded by the sealant 605 is a space 607.

Note that a lead wiring 608 is a wiring for transmitting signals to be input to the source line driver circuit 601 and the gate line driver circuit 603 and receiving a video signal, a clock signal, a start signal, a reset signal, and the like from an FPC (flexible printed circuit) 609 serving as an external input terminal. Although only the FPC is illustrated here, a printed wiring board (PWB) may be attached to this FPC. The light-emitting apparatus in this specification includes not only the light-emitting apparatus itself but also the apparatus provided with the FPC or the PWB.

Next, a cross-sectional structure will be described with reference to FIG. 2(B). The driver circuit portion and the pixel portion are formed over a device substrate 610. Here, the source line driver circuit 601, which is the driver circuit portion, and one pixel of the pixel portion 602 are illustrated.

The device substrate 610 may be fabricated using a substrate containing glass, quartz, an organic resin, a metal, an alloy, a semiconductor, or the like, or a plastic substrate formed of FRP (Fiber Reinforced Plastic), PVF (polyvinyl fluoride), polyester, acrylic resin, or the like.

The structure of transistors used in pixels and driver circuits is not particularly limited. For example, an inverted staggered transistor or a staggered transistor may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as In-Ga-Zn-based metal oxide, may be used.

There is no particular limitation on the crystallinity of a semiconductor material used for the transistors, and any of an amorphous semiconductor or a semiconductor having crystallinity (a microcrystalline semiconductor, a polycrystalline semiconductor, a single-crystal semiconductor, and a semiconductor partly including crystal regions) may be used. A semiconductor having crystallinity is preferably used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. The use of an oxide semiconductor material having a wider band gap than silicon can reduce the off-state current of the transistors.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such a material as the semiconductor layer makes it possible to achieve a highly reliable transistor in which a change in the electrical characteristics is reduced.

Charge accumulated in a capacitor through a transistor including the above-described semiconductor layer can be retained for a long time because of the low off-state current of the transistor. The use of such a transistor in pixels allows a driver circuit to stop while the gray level of an image displayed on each display region is maintained. As a result, electronic equipment with significantly reduced power consumption can be achieved.

For stable characteristics of the transistor or the like, a base film is preferably provided. The base film can be formed to be a single-layer or a stacked-layer using an inorganic insulating film such as a silicon oxide film, a silicon nitride film, a silicon oxynitride film, or a silicon nitride oxide film. The base film can be formed by a sputtering method, a CVD (Chemical Vapor Deposition) method (e.g., a plasma CVD method, a thermal CVD method, or an MOCVD (Metal Organic CVD) method), an ALD (Atomic Layer Deposition) method, a coating method, a printing method, or the like. Note that the base film is not necessarily provided when not needed.

Note that an FET 623 is illustrated as a transistor formed in the driver circuit portion 601. The driver circuit can be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and can be formed outside.

The pixel portion 602 is formed with a plurality of pixels including a switching FET 611, a current control FET 612, and a first electrode 613 electrically connected to a drain of the current control FET 612; however, without being limited thereto, a pixel portion in which three or more FETs and a capacitor are combined may be employed.

Note that an insulator 614 is formed to cover an end portion of the first electrode 613. The insulator 614 can be formed using a positive photosensitive acrylic resin film here.

In order to improve the coverage with an EL layer or the like to be formed later, the insulator 614 is formed so as to have a curved surface with curvature at its upper end portion or lower end portion. For example, in the case where positive photosensitive acrylic resin is used as a material for the insulator 614, only the upper end portion of the insulator 614 preferably has a curved surface with a curvature radius (0.2 μm to 3 μm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material with a high work function is desirably used. For example, a single-layer film of an ITO film, an indium tin oxide film containing silicon, an indium oxide film containing zinc oxide at 2 to 20 wt %, a titanium nitride film, a chromium film, a tungsten film, a Zn film, a Pt film, or the like, a stacked layer of titanium nitride film and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 2. Alternatively, a material included in the EL layer 616 may be a low molecular compound or a high molecular compound (including an oligomer or a dendrimer).

As a material used for the second electrode 617, which is formed over the EL layer 616 and functions as a cathode, a material with a low work function (e.g., Al, Mg, Li, Ca, or an alloy or a compound thereof (e.g., MgAg, MgIn, or AlLi)) is preferably used. Note that in the case where light generated in the EL layer 616 passes through the second electrode 617, it is preferable to use, for the second electrode 617, a stacked layer of a thin metal film and a transparent conductive film (e.g., ITO, indium oxide containing zinc oxide at 2 to 20 wt %, indium tin oxide containing silicon, or zinc oxide (ZnO)).

Note that a light-emitting device is formed with the first electrode 613, the EL layer 616, and the second electrode 617. The light-emitting device is the light-emitting device described in Embodiment 2. A plurality of light-emitting devices are formed in the pixel portion, and the light-emitting apparatus of this embodiment may include both the light-emitting device described in Embodiment 2 and a light-emitting device having a different structure.

The sealing substrate 604 and the device substrate 610 are attached to each other using the sealant 605, so that a structure is employed in which a light-emitting device 618 is provided in the space 607 surrounded by the device substrate 610, the sealing substrate 604, and the sealant 605. The space 607 is filled with a filler; it is filled with an inert gas (e.g., nitrogen or argon) in some cases, and filled with the sealant in some cases. The structure of the sealing substrate in which a recessed portion is formed and a desiccant is provided is preferable because deterioration due to the influence of moisture can be inhibited.

Note that an epoxy-based resin or glass frit is preferably used for the sealant 605. Furthermore, these materials are preferably materials that transmit moisture or oxygen as little as possible. As the material used for the sealing substrate 604, in addition to a glass substrate and a quartz substrate, a plastic substrate formed of FRP (Fiber Reinforced Plastics), PVF (polyvinyl fluoride), polyester, acrylic resin, or the like can be used.

Although not illustrated in FIG. 2, a protective film may be provided over the second electrode. The protective film may be formed using an organic resin film or an inorganic insulating film. The protective film may be formed so as to cover an exposed portion of the sealant 605. The protective film may be provided so as to cover surfaces and side surfaces of the pair of substrates and exposed side surfaces of a sealing layer, an insulating layer, and the like.

For the protective film, a material that is less likely transmit an impurity such as water. Thus, diffusion of an impurity such as water from the outside into the inside can be effectively inhibited.

As a material included in the protective film, an oxide, a nitride, a fluoride, a sulfide, a ternary compound, a metal, a polymer, or the like can be used; for example, it is possible to use a material containing aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide; a material containing aluminum nitride, hafnium nitride, silicon nitride, tantalum nitride, titanium nitride, niobium nitride, molybdenum nitride, zirconium nitride, gallium nitride; a material containing a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method that enables favorable step coverage. One such method is an atomic layer deposition (ALD) method. A material that can be formed by an ALD method is preferably used for the protective film. With the use of an ALD method, a dense protective film with reduced defects such as cracks and pinholes or with a uniform thickness can be formed. Furthermore, damage caused to a process member in forming the protective film can be reduced.

By an ALD method, a uniform protective film with few defects can be formed even on a surface with a complex uneven shape or upper, side, and lower surfaces of a touch panel.

As described above, the light-emitting apparatus fabricated using the light-emitting device described in Embodiment 2 can be obtained.

For the light-emitting apparatus in this embodiment, the light-emitting device described in Embodiment 2 is used and thus a light-emitting apparatus having favorable characteristics can be obtained. Specifically, since the light-emitting device described in Embodiment 2 has high emission efficiency, the light-emitting apparatus can achieve low power consumption.

FIG. 3 illustrates examples of a light-emitting apparatus in which full color display is achieved by formation of a light-emitting device exhibiting white light emission and provision of coloring layers (color filters) and the like. FIG. 3(A) illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of the light-emitting devices, a partition 1025, an EL layer 1028, a second electrode 1029 of the light-emitting devices, a sealing substrate 1031, a sealant 1032, and the like.

In FIG. 3(A), coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black matrix is positioned and fixed to the substrate 1001. Note that the coloring layers and the black matrix 1035 are covered with an overcoat layer 1036. In FIG. 3(A), a light-emitting layer from which light is emitted to the outside without passing through the coloring layer and light-emitting layers from which light is emitted to the outside, passing through the coloring layers of the respective colors are shown. Since light that does not pass through the coloring layer is white and light that passes through the coloring layer is red, green, or blue, an image can be expressed by pixels of the four colors.

FIG. 3(B) illustrates an example in which the coloring layers (the red coloring layer 1034R, the green coloring layer 1034G, and the blue coloring layer 1034B) are formed between the gate insulating film 1003 and the first interlayer insulating film 1020. The coloring layers may be provided between the substrate 1001 and the sealing substrate 1031 in this manner.

Figure 4:
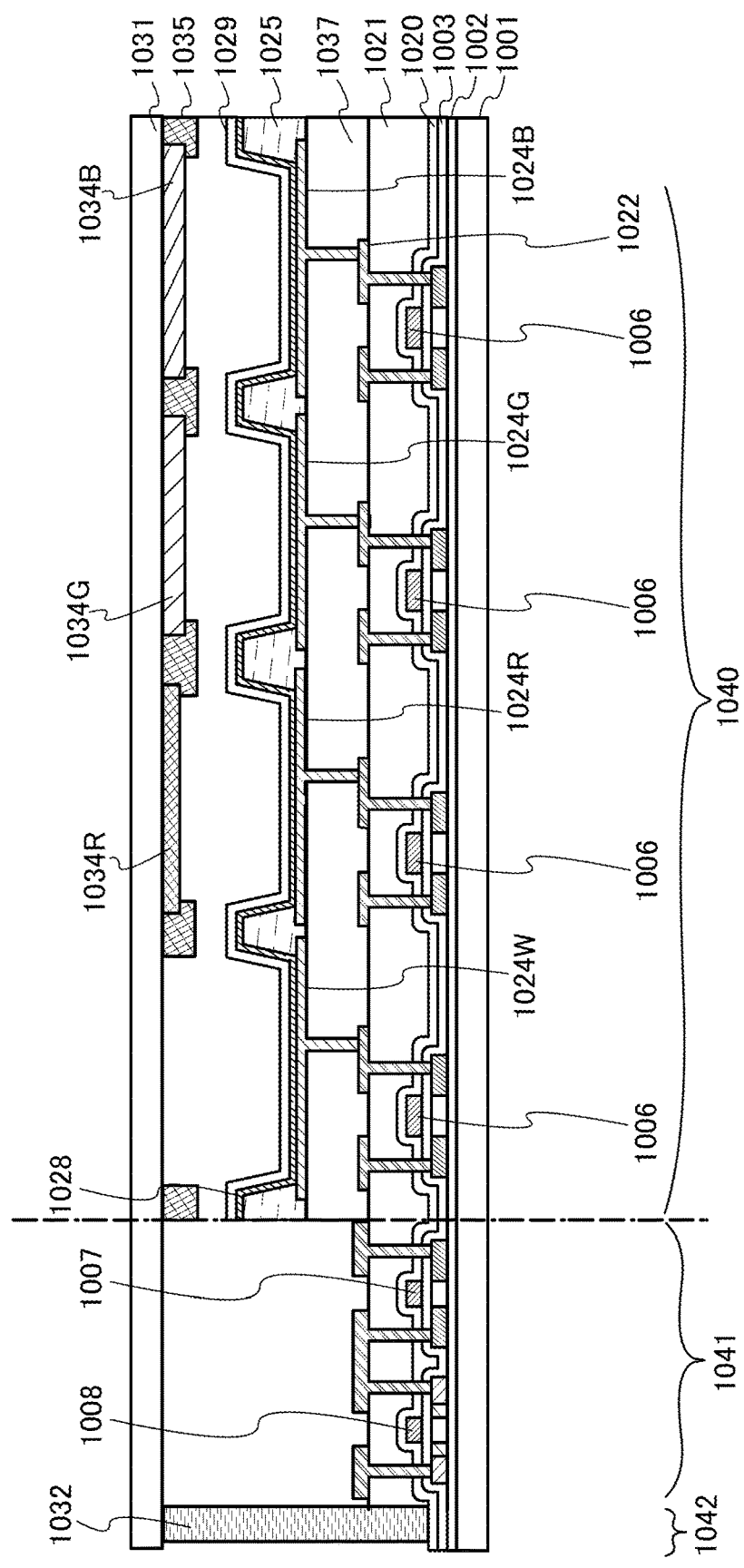
FIG. 4 is a schematic diagram of an active matrix light-emitting apparatus.

The above-described light-emitting apparatus is a light-emitting apparatus having a structure in which light is extracted to the substrate 1001 side where the FETs are formed (a bottom-mission type), but may be a light-emitting apparatus having a structure in which light emission is extracted to the sealing substrate 1031 side (a top-emission type). FIG. 4 illustrates a cross-sectional view of a top-emission light-emitting apparatus. In this case, a substrate that does not transmit light can be used as the substrate 1001. The top-emission light-emitting apparatus is formed in a manner similar to that of the bottom-emission light-emitting apparatus until a connection electrode which connects the FET and the anode of the light-emitting device is formed. Then, a third interlayer insulating film 1037 is formed to cover an electrode 1022. This insulating film may have a planarization function. The third interlayer insulating film 1037 can be formed using a material similar to that for the second interlayer insulating film or using any other known materials.

The first electrodes 1024W, 1024R, 1024G, and 1024B of the light-emitting devices are each an anode here, but may each be a cathode. Furthermore, in the case of the top-emission light-emitting apparatus illustrated in FIG. 4, the first electrodes are preferably reflective electrodes. The structure of the EL layer 1028 is such a structure as described as that of the EL layer 103 in Embodiment 2, and a device structure with which white light emission can be obtained.

In the case of such a top-emission structure as in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer. Note that a light-transmitting substrate is used as the sealing substrate 1031. Although an example in which full color display is performed using four colors of red, green, blue, and white is shown here, there is no particular limitation and full color display may be performed using four colors of red, yellow, green, and blue or three colors of red, green, and blue.

In the top-emission-type light-emitting apparatus, a microcavity structure can be favorably employed. A light-emitting device with a microcavity structure can be obtained with the use of a reflective electrode as the first electrode and a semi-transmissive and semi-reflective electrode as the second electrode. The light-emitting device with a microcavity structure includes at least an EL layer between the reflective electrode and the semi-transmissive and semi-reflective electrode, which includes at least a light-emitting layer serving as a light-emitting region.

Note that the reflective electrode is a film having a visible light reflectivity of 40% to 100%, preferably 70% to 100%, and a resistivity of $1 \times 10^{-2}$ Ωcm or lower. In addition, the semi-transmissive and semi-reflective electrode is a film having a visible light reflectivity of 20% to 80%, preferably 40% to 70%, and a resistivity of $1 \times 10^{-2}$ Ωcm or lower.

Light emitted from the light-emitting layer included in the EL layer is reflected and resonated by the reflective electrode and the semi-transmissive and semi-reflective electrode.

In the light-emitting device, by changing thicknesses of the transparent conductive film, the above-described composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light); therefore, the optical path length between the reflective electrode and the light-emitting layer is preferably adjusted to $(2n-1)\lambda/4$ (n is a natural number of 1 or larger and $\lambda$ is a wavelength of light emission to be amplified). By adjusting the optical path length, the phases of the first reflected light and the first incident light can be aligned with each other and the light emitted from the light-emitting layer can be further amplified.

Note that in the above structure, the EL layer may have a structure including a plurality of light-emitting layers or may have a structure including a single light-emitting layer. In combination with the tandem light-emitting device described above, for example, it can be used in a structure where a light-emitting device is provided with a plurality of EL layers, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting apparatus which displays images with subpixels of four colors, red, yellow, green, and blue, the light-emitting apparatus can have favorable characteristics because a microcavity structure suitable for wavelengths of the corresponding color is employed in each subpixel, in addition to the effect of an improvement in luminance awing to yellow light emission.

For the light-emitting apparatus in this embodiment, the light-emitting device described in Embodiment 2 is used and thus a light-emitting apparatus having favorable characteristics can be obtained. Specifically, since the light-emitting device described in Embodiment 2 has high emission efficiency, the light-emitting apparatus with a low power consumption can be obtained.

Figure 5A:
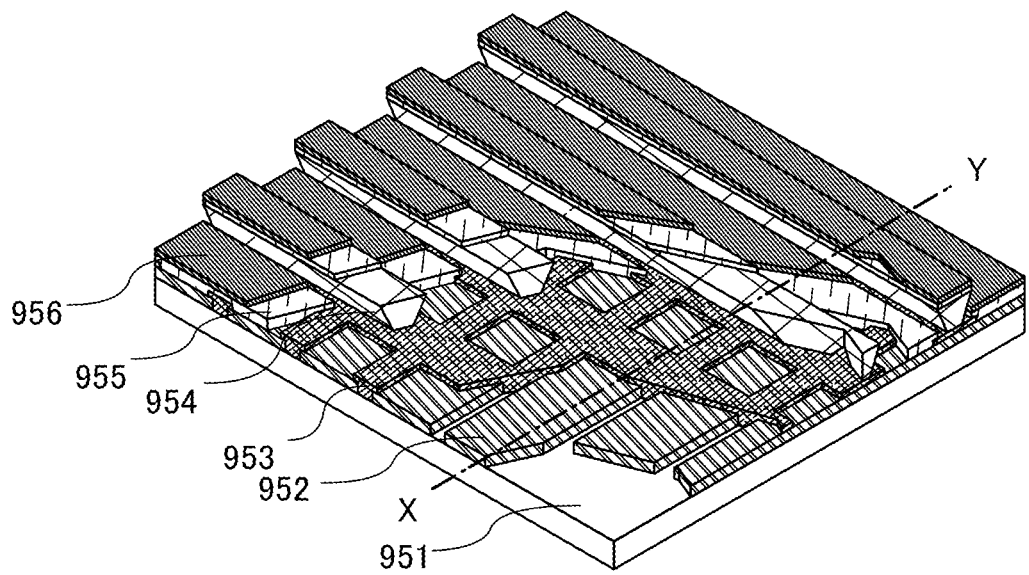
FIGS. 5A and 5B are conceptual diagrams of a passive matrix light-emitting apparatus.
Figure 5B:
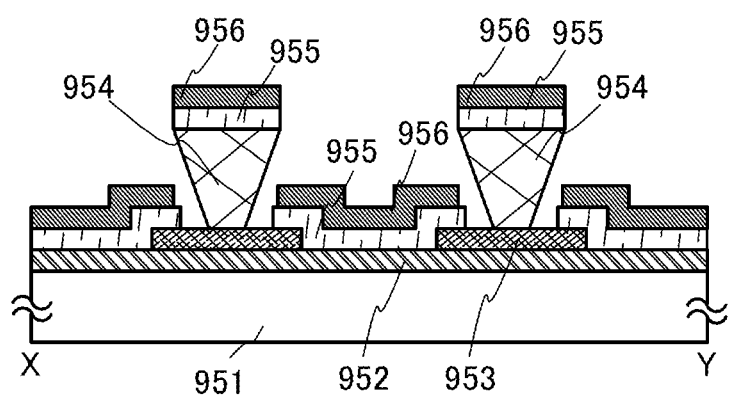

The active matrix light-emitting apparatus is described above, whereas a passive matrix light-emitting apparatus is described below. FIG. 5 illustrates a passive matrix light-emitting apparatus fabricated using the present invention. Note that FIG. 5(A) is a perspective view illustrating the light-emitting apparatus, and FIG. 5(B) is a cross-sectional view taken along X-Y in FIG. 5(A). In FIG. 5, over a substrate 951, an EL layer 955 is provided between an electrode 952 and an electrode 956. An end portion of the electrode 952 is covered with an insulating layer 953. A partition layer 954 is provided over the insulating layer 953. Sidewalls of the partition layer 954 are aslope such that the distance between one sidewall and the other sidewall is gradually narrowed toward the surface of the substrate. That is, a cross section in the short side direction of the partition layer 954 is a trapezoidal shape, and the lower side (the side facing the same direction as the plane direction of the insulating layer 953 and touching the insulating layer 953) is shorter than the upper side (the side facing the same direction as the plane direction of the insulating layer 953, and not touching the insulating layer 953). By providing the partition layer 954 in this manner, defects of the light-emitting device due to static charge or the like can be prevented. The passive-matrix light-emitting apparatus also uses the light-emitting device described in Embodiment 2; thus, the light-emitting apparatus can have favorable reliability or low power consumption.

Since many minute light-emitting devices arranged in a matrix can each be controlled in the light-emitting apparatus described above, the light-emitting apparatus can be suitably used as a display device for displaying images.

This embodiment can be freely combined with any of the other embodiments.

Embodiment 4

Figure 6A:
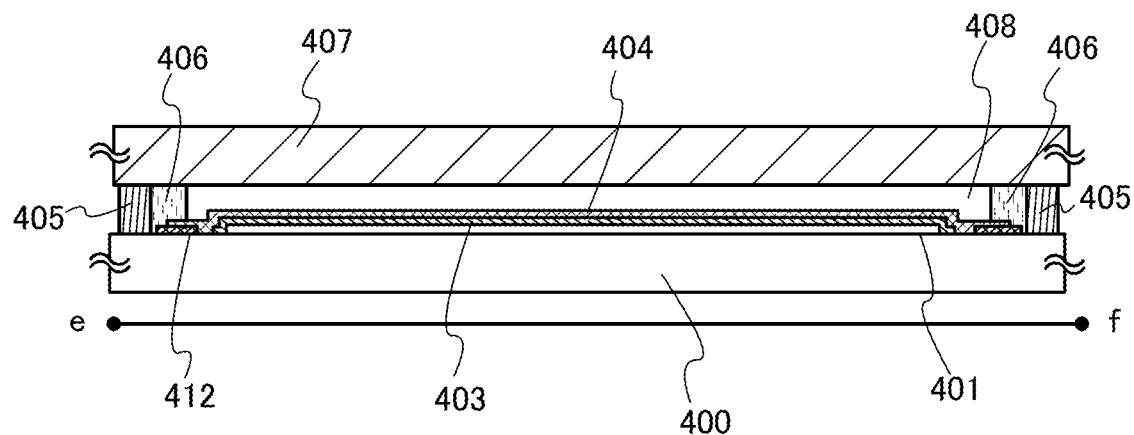
FIGS. 6A and 6B are diagrams illustrating a lighting device.
Figure 6B:
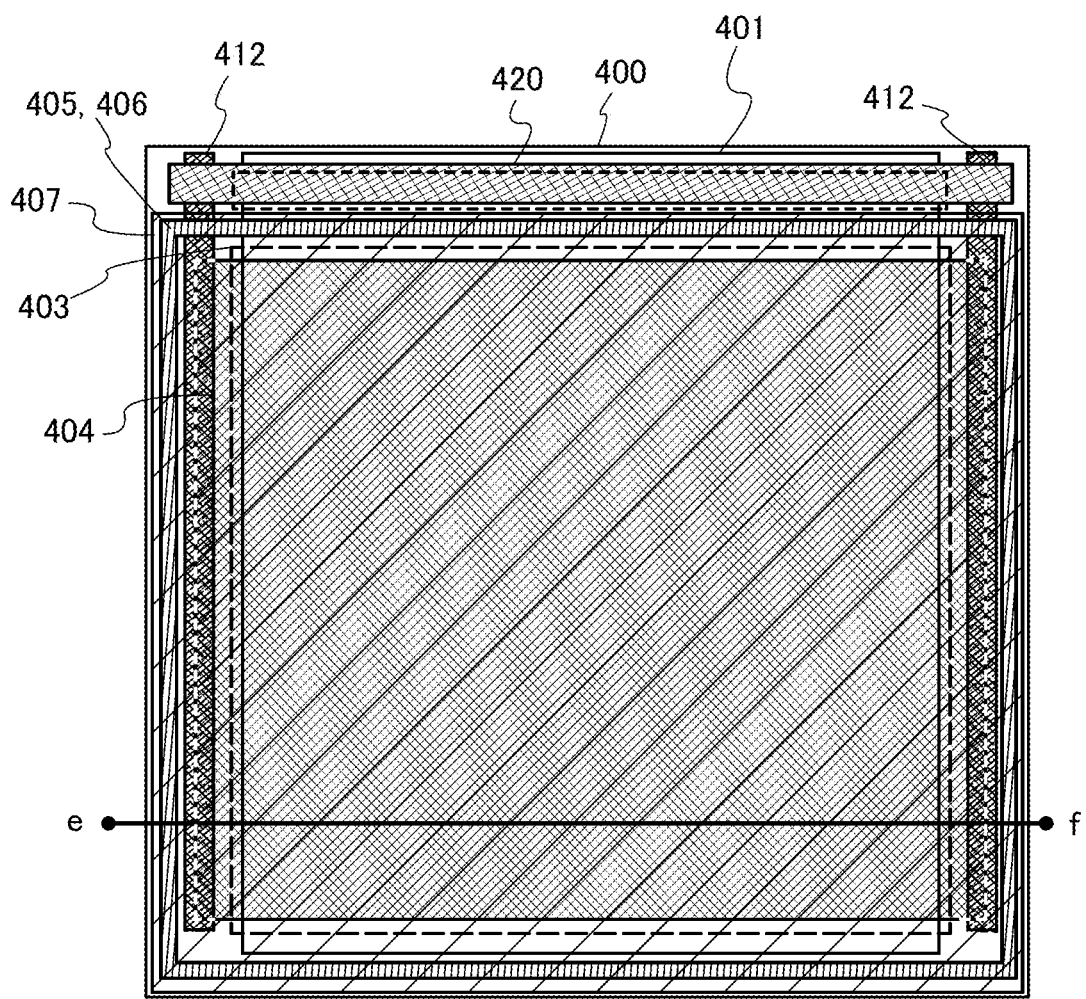

In this embodiment, an example in which the light-emitting device described in Embodiment 2 is used for a lighting device will be described with reference to FIG. 6. FIG. 6(B) is a top view of the lighting device, and FIG. 6(A) is a cross-sectional view taken along e-f in FIG. 6(B).

In the lighting device in this embodiment, a first electrode 401 is formed over a substrate 400 which is a support and has a light-transmitting property. The first electrode 401 corresponds to the first electrode 101 in Embodiment 2. In the case where light emission is extracted from the first electrode 401 side, the first electrode 401 is formed with a material having a light-transmitting property.

A pad 412 for supplying a voltage to a second electrode 404 is formed over the substrate 400.

An EL layer 403 is formed over the first electrode 401. The EL layer 403 has a structure corresponding to that of the EL layer 103 in Embodiment 2, or the structure in which the light-emitting units 511 and 512 are combined with the charge-generation layer 513. Note that for these structures, the corresponding description can be referred to.

The second electrode 404 is formed to cover the EL layer 403. The second electrode 404 corresponds to the second electrode 102 in Embodiment 2. In the case where light-emission is extracted from the first electrode 401 side, the second electrode 404 is formed with a material having high reflectivity. The second electrode 404 is supplied with a voltage when connected to the pad 412.

As described above, the lighting device described in this embodiment includes a light-emitting device including the first electrode 401, the EL layer 403, and the second electrode 404. Since the light-emitting device is a light-emitting device with high emission efficiency, the lighting device in this embodiment can be a lighting device with low power consumption.

The substrate 400 over which the light-emitting device having the above structure is formed is fixed to a sealing substrate 407 with sealants 405 and 406 and sealing is performed, whereby the lighting device is completed. It is possible to use only either the sealant 405 or 406. In addition, the inner sealant 406 (not illustrated in FIG. 6(B)) can be mixed with a desiccant, which enables moisture to be adsorbed, resulting in improved reliability.

When parts of the pad 412 and the first electrode 401 are provided to extend to the outside of the sealants 405 and 406, those can serve as external input terminals. An IC chip 420 mounted with a converter or the like may be provided over the external input terminals.

The lighting device described in this embodiment uses the light-emitting device described in Embodiment 2 as an EL device; thus, the light-emitting apparatus can have low power consumption.

Embodiment 5

In this embodiment, examples of electronic equipment each partly including the light-emitting device described in Embodiment 2 will be described. The light-emitting device described in Embodiment 2 is a light-emitting device having a high emission efficiency and low power consumption. As a result, the electronic equipment described in this embodiment can be electronic equipment each including a light-emitting portion with low power consumption.

Examples of electronic equipment to which the light-emitting device is applied include a television devices (also referred to as TV or television receivers), monitors for computers and the like, cameras such as digital cameras and digital video cameras, digital photo frames, mobile phones (also referred to as portable telephones or portable telephone devices), portable game machines, portable information terminals, audio playback devices, and large game machines such as pin-ball machines. Specific examples of the electronic equipment are shown below.

Figure 7A:
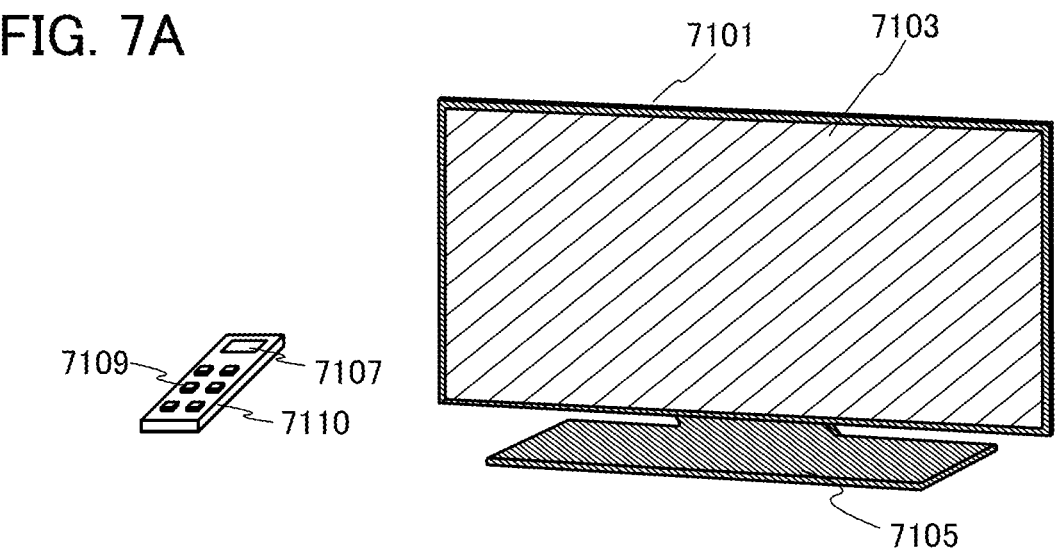
Figure 7A:
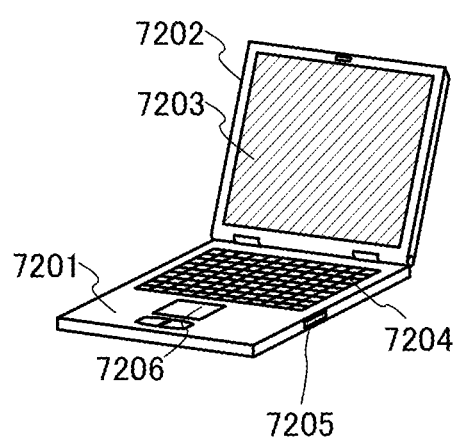
Figure 7A:
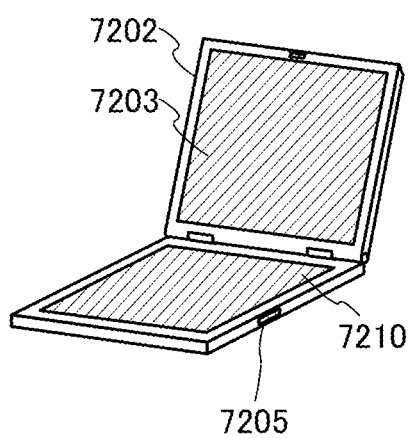

FIG. 7(A) illustrates an example of a television device. In the television device, a display portion 7103 is incorporated in a housing 7101. Here, a structure in which the housing 7101 is supported by a stand 7105 is shown. Images can be displayed on the display portion 7103, and the light-emitting devices described in Embodiment 2 are arranged in a matrix in the display portion 7103.

The television device can be operated with an operation switch of the housing 7101 or a separate remote controller

7110. With operation keys 7109 of the remote controller 7110, channels and volume can be operated and images displayed on the display portion 7103 can be operated. Furthermore, a structure may be employed in which the remote controller 7110 is provided with a display portion 7107 for displaying data output from the remote controller 7110.

Note that the television device has a structure of including a receiver, a modem, and the like. With the use of the receiver, a general television broadcast can be received, and moreover, when the television device is connected to a communication network with or without a wire via the modem, one-way (from a sender to a receiver) or two-way (between a sender and a receiver or between receivers) data communication can be performed.

FIG. 7(B1) is a computer which includes a main body 7201, a housing 7202, a display portion 7203, a keyboard 7204, an external connection port 7205, a pointing device 7206, and the like. Note that this computer is fabricated using the light-emitting devices described in Embodiment 2 arranged in a matrix in the display portion 7203. The computer in FIG. 7(B1) may be such a mode as illustrated in FIG. 7(B2). The computer in FIG. 7(B2) is provided with a second display portion 7210 instead of the keyboard 7204 and the pointing device 7206. The second display portion 7210 is of a touch-panel type, and input can be performed by operating display for input displayed on the second display portion 7210 with a finger or a dedicated pen. The second display portion 7210 can also display images other than the display for input. The display portion 7203 may also be a touch panel. Connecting the two screens with a hinge can prevent troubles such as a crack in or damage to the screens caused when the computer is stored or carried.

Figure 7C:
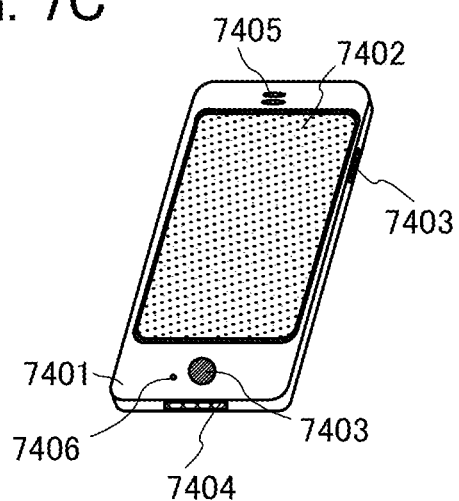

FIG. 7(C) illustrates a mobile phone as an example of a portable terminal. The mobile phone includes operation buttons 7403, an external connection port 7404, a speaker 7405, a microphone 7406, and the like in addition to a display portion 7402 incorporated in a housing 7401. Note that the mobile phone includes the display portion 7402 which is fabricated by arranging the light-emitting devices described in Embodiment 2 in a matrix.

The portable terminal illustrated in FIG. 7(C) may have a structure in which information can be input by touching the display portion 7402 with a finger or the like. In this case, operations such as making a call and creating an e-mail can be performed by touching the display portion 7402 with a finger or the like.

The display portion 7402 has mainly three screen modes. The first one is a display mode mainly for displaying images, and the second one is an input mode mainly for inputting data such as text. The third one is a display+input mode in which two modes of the display mode and the input mode are combined.

For example, in the case of making a call or creating an e-mail, a text input mode mainly for inputting text is selected for the display portion 7402 so that an operation of inputting text displayed on the screen may be performed. In this case, it is preferable to display a keyboard or number buttons on almost the entire screen of the display portion 7402.

When a sensing device including a sensor for sensing inclination, such as a gyroscope sensor or an acceleration sensor, is provided inside the portable terminal, screen display of the display portion 7402 can be automatically changed by determining the orientation of the portable terminal (vertically or horizontally).

The screen modes are changed by touching the display portion 7402 or operating the operation buttons 7403 of the housing 7401. Alternatively, the screen modes can be changed depending on the kind of image displayed on the display portion 7402. For example, when a signal of an image displayed on the display portion is moving image data, the screen mode is changed to the display mode, and when the signal is text data, the screen mode is changed to the input mode.

Moreover, in the input mode, when input by the touch operation of the display portion 7402 is not performed for a certain period while a signal sensed by an optical sensor in the display portion 7402 is sensed, the screen mode may be controlled so as to be changed from the input mode to the display mode.

The display portion 7402 can also function as an image sensor. For example, an image of a palm print, a fingerprint, or the like is taken when the display portion 7402 is touched with the palm or the finger, whereby personal authentication can be performed. Furthermore, by using a backlight which emits near-infrared light or a sensing light source which emits near-infrared light in the display portion, an image of a finger vein, a palm vein, or the like can be taken.

Note that the structures described in this embodiment can be combined with the structures described in any of Embodiment 1 to Embodiment 4 as appropriate.

As described above, the application range of the light-emitting apparatus including the light-emitting device described in Embodiment 2 is wide so that this light-emitting apparatus can be applied to electronic equipment in a variety of fields. With the use of the light-emitting device described in Embodiment 2, electronic equipment with low power consumption can be obtained.

Figure 8A:
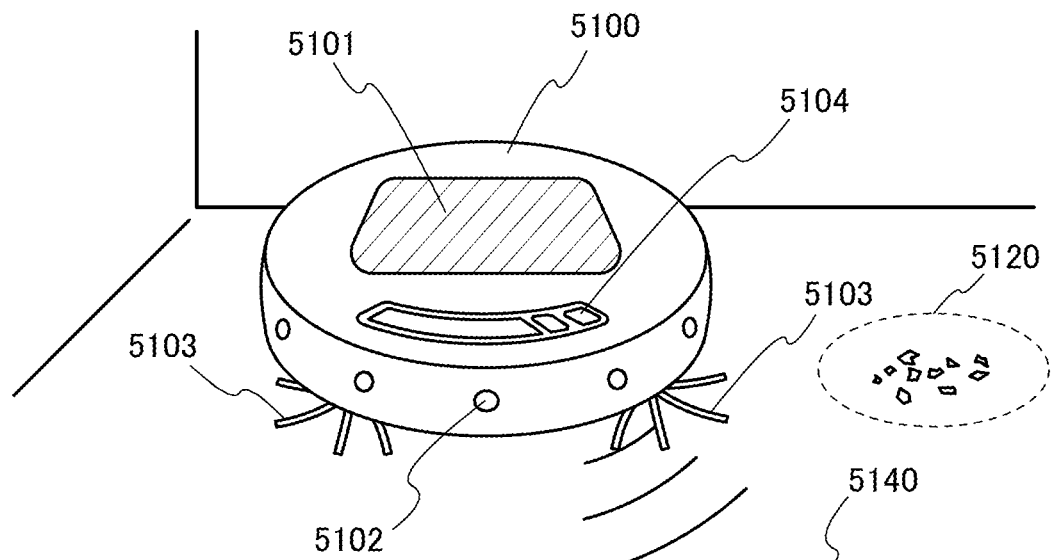
FIGS. 8A-8C are diagrams illustrating electronic equipment.

FIG. 8(A) is a schematic view illustrating an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and sucks up the dust through the inlet provided on the bottom surface.

The cleaning robot 5100 can judge whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display a path on which the cleaning robot 5100 has run. The display 5101 may be a touch panel, and the operation buttons 5104 may be provided on the display 5101.

The cleaning robot 5100 can communicate with portable electronic equipment 5140 such as a smartphone. The portable electronic equipment 5140 can display images taken by the cameras 5102. Accordingly, an owner of the cleaning robot 5100 can monitor the room even from the outside. The display on the display 5101 can be checked by the portable electronic equipment such as a smartphone.

The light-emitting apparatus of one embodiment of the present invention can be used for the display 5101.

Figure 8B:
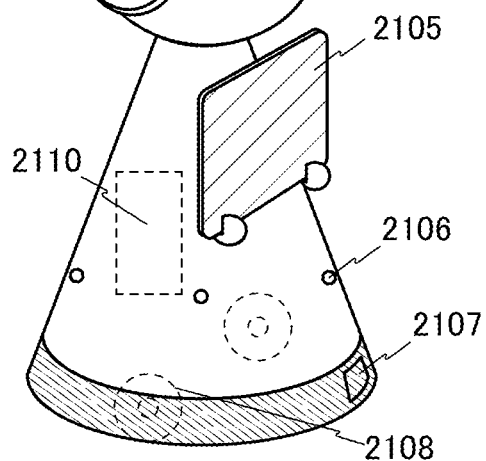

A robot 2100 illustrated in FIG. 8(B) includes an arithmetic device 2110, an illuminance sensor 2101, a microphone 2102, an upper camera 2103, a speaker 2104, a display 2105, a lower camera 2106, and an obstacle sensor 2107, a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 8C:
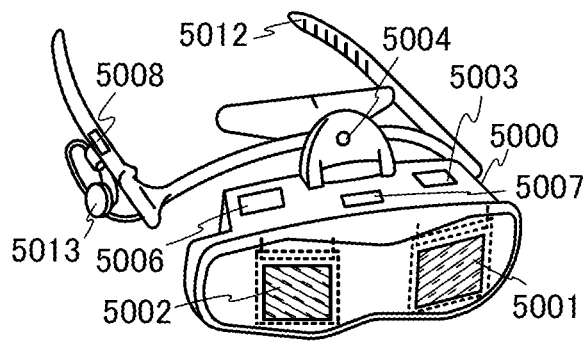

FIG. 8(C) shows an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 5008, a display portion 5002, a support 5012, and an earphone 5013.

The light-emitting apparatus of one embodiment of the present invention can be used for the display portion 5001 and the display portion 5002.

Figure 9:
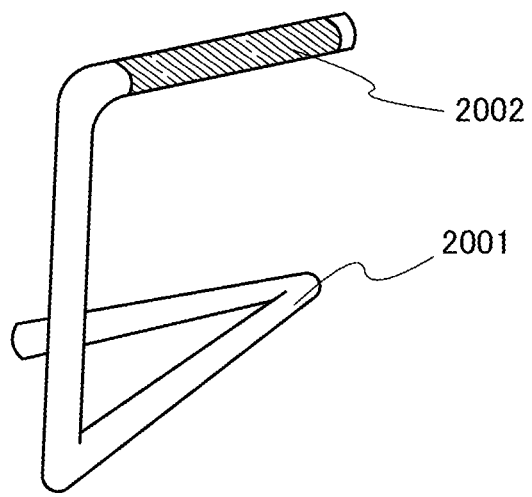
FIG. 9 is a diagram illustrating a lighting device.

FIG. 9 illustrates an example in which the light-emitting device described in Embodiment 2 is used for a table lamp which is a lighting device. The table lamp illustrated in FIG. 9 includes a housing 2001 and a light source 2002, and the lighting device described in Embodiment 4 may be used for the light source 2002.

Figure 10:
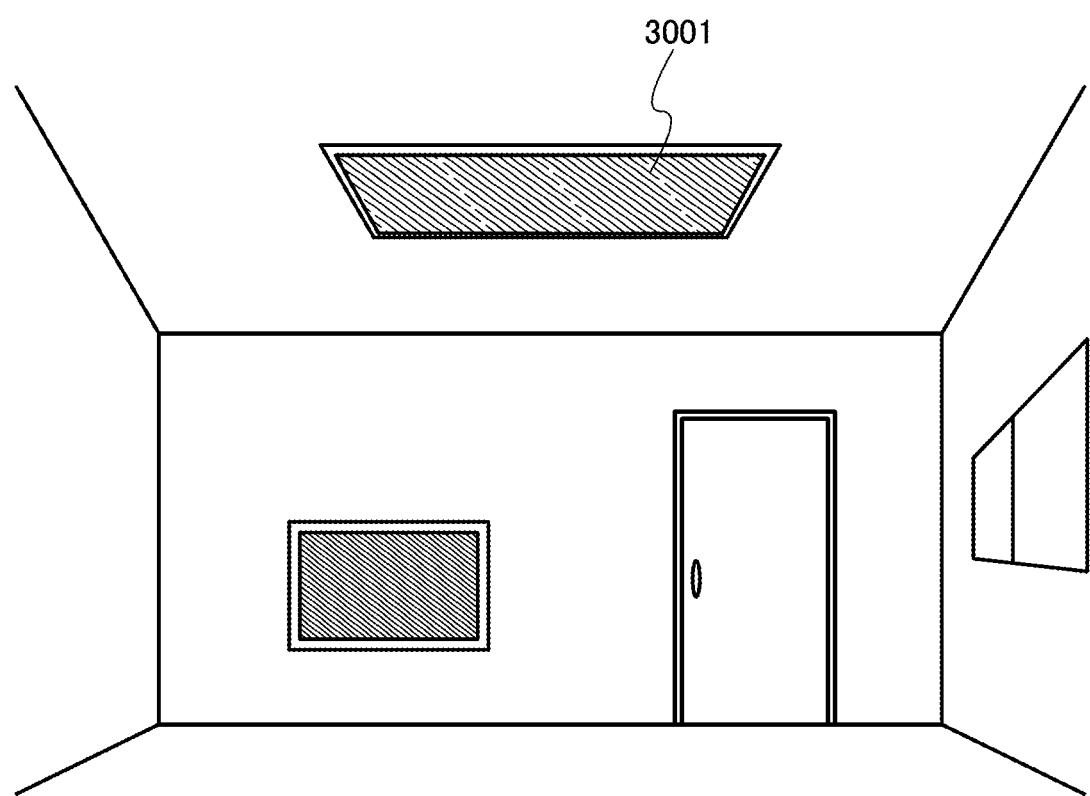
FIG. 10 is a diagram illustrating a lighting device.

FIG. 10 illustrates an example in which the light-emitting device described in Embodiment 2 is used for an indoor lighting device 3001. Since the light-emitting device described in Embodiment 2 is a light-emitting device having high emission efficiency, the lighting device can have low power consumption. Furthermore, the light-emitting device described in Embodiment 2 can have a larger area, and thus can be used for a large-area lighting device. Furthermore, the light-emitting device described in Embodiment 2 is thin, and thus can be used for a lighting device having a reduced thickness.

Figure 11:
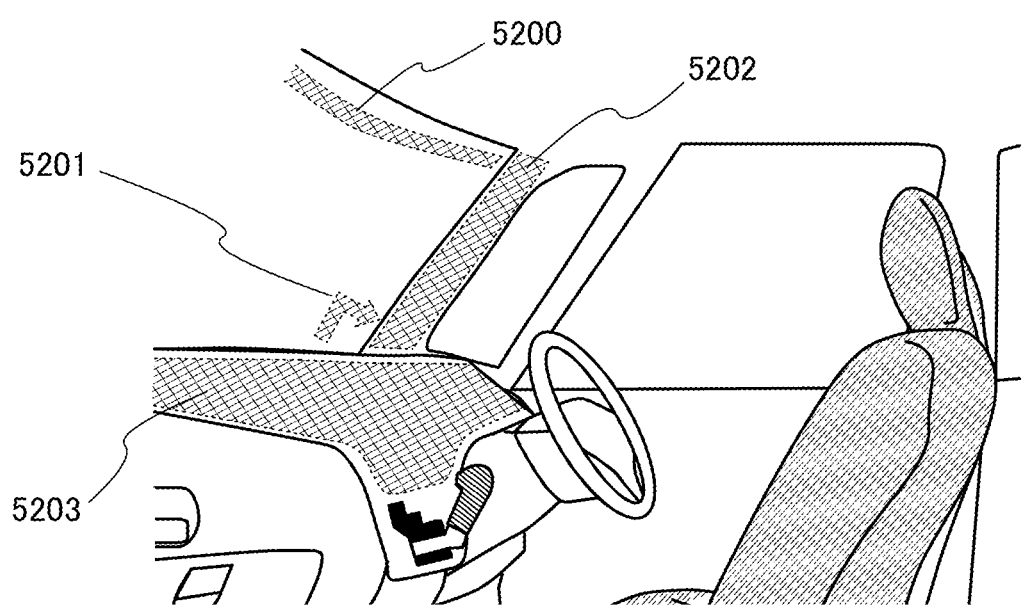
FIG. 11 is a diagram illustrating in-vehicle display devices and lighting devices.

The light-emitting device described in Embodiment 2 can also be incorporated in an automobile windshield or an automobile dashboard. FIG. 11 illustrates one mode in which the light-emitting device described in Embodiment 2 is used for a windshield and a dashboard of an automobile. A display region 5200 to a display region 5203 are each a display provided using the light-emitting device described in Embodiment 2.

The display region 5200 and the display region 5201 are display devices provided in the automobile windshield, in which the light-emitting devices described in Embodiment 2 are incorporated. When the light-emitting devices described in Embodiment 2 are fabricated using electrodes having light-transmitting properties as a first electrode and a second electrode, what is called see-through display devices, through which the opposite side can be seen, can be obtained. See-through display devices can be provided without hindering the vision even when being provided in the automobile windshield. Note that in the case where a driving transistor or the like is provided, a transistor having a light-transmitting property, such as an organic transistor using an organic semiconductor material or a transistor using an oxide semiconductor, is preferably used.

The display region 5202 is a display device provided in a pillar portion, in which the light-emitting devices described in Embodiment 2 are incorporated. The display region 5202 can compensate for the view hindered by the pillar by displaying an image taken by an imaging means provided on the car body. Similarly, the display region 5203 provided in the dashboard portion can compensate for the view hindered by the car body by displaying an image taken by an imaging means provided on the outside of the automobile. Thus, blind areas can be compensated for and the safety can be enhanced. Showing an image so as to compensate for the area that cannot be seen makes it possible to confirm safety more naturally and comfortably.

The display region 5203 can provide a variety of kinds of information by displaying navigation data, a speedometer, a tachometer, a mileage, a fuel meter, a gearshift state, air-condition setting, and the like. The content or layout of the display can be changed freely in accordance with the preference of a user. Note that such information can also be provided on the display region 5200 to the display region 5202. The display region 5200 to the display region 5203 can also be used as lighting devices.

Figure 12A:
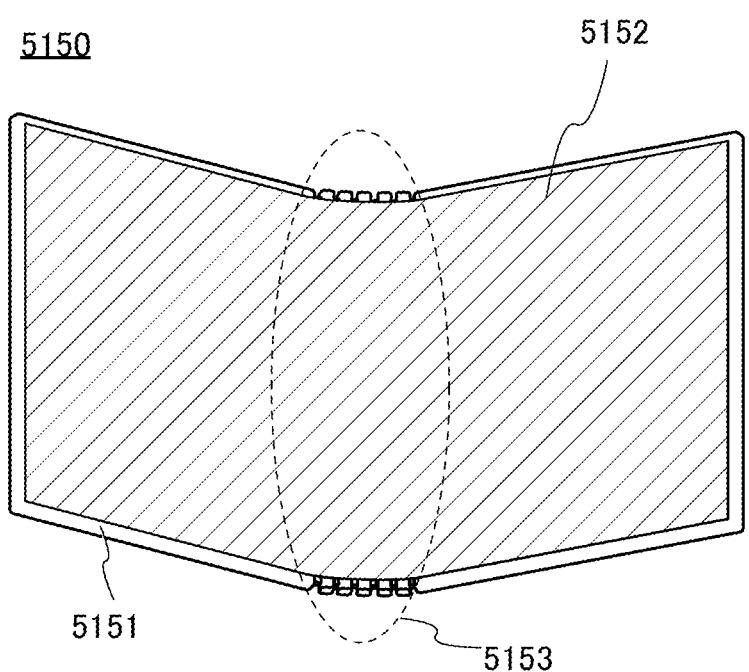
FIGS. 12A and 12B are diagrams illustrating electronic equipment.
Figure 12B:
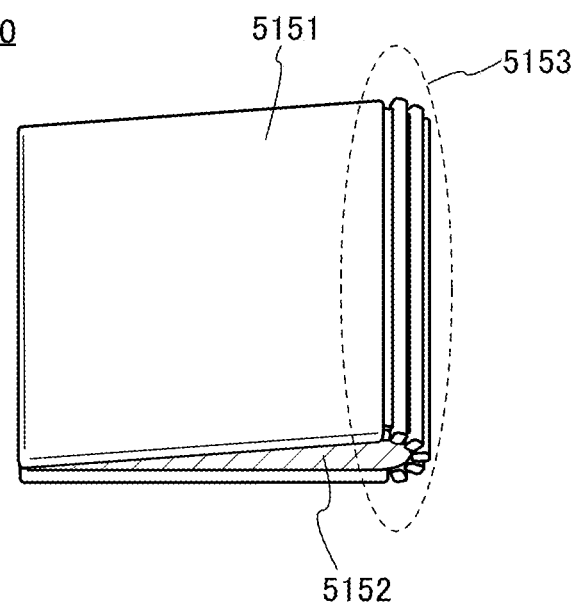

FIGS. 12(A) and 12(B) illustrate a foldable portable information terminal 5150. The foldable portable information terminal 5150 includes a housing 5151, a display region 5152, and a bend portion 5153. FIG. 12(A) illustrates the portable information terminal 5150 that is opened. FIG. 12(B) illustrates the portable information terminal that is folded. The portable information terminal 5150 is compact in size and has excellent portability when folded, despite its large display region 5152.

The display region 5152 can be folded in half with the bend portion 5153. The bend portion 5153 includes a flexible member and a plurality of supporting members, and when the display region is folded, the flexible member expands and the bend portion 5153 has a radius of curvature of 2 mm or more, preferably 3 mm or more.

Note that the display region 5152 may be a touch panel (an input/output device) including a touch sensor (an input device). The light-emitting apparatus of one embodiment of the present invention can be used for the display region 5152.

Figure 13A:
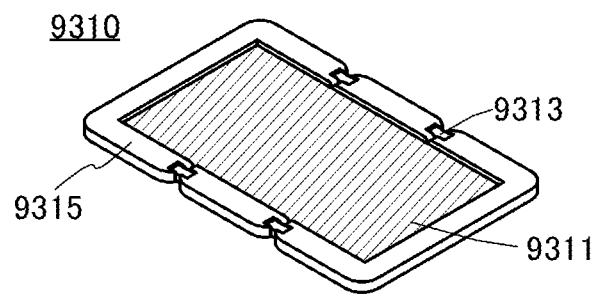
FIGS. 13A-13C are diagrams illustrating electronic equipment.
Figure 13B:
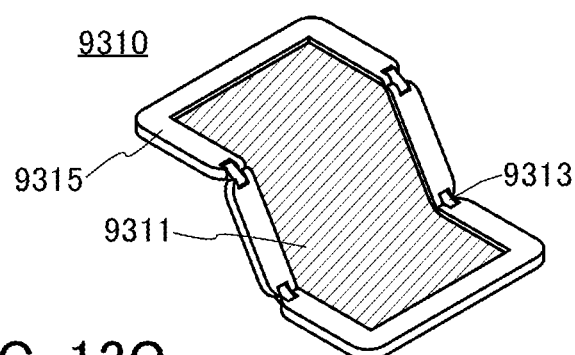
Figure 13C:
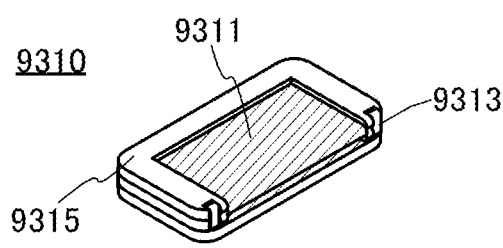

FIGS. 13(A) to 13(C) illustrate a foldable portable information terminal 9310. FIG. 13(A) illustrates the portable information terminal 9310 that is opened. FIG. 13(B) illustrates the portable information terminal 9310 which is in the state of being changed from one of an opened state and a folded state to the other. FIG. 13(C) illustrates the portable information terminal 9310 that is folded. The portable information terminal 9310 is excellent in portability when folded, and is excellent in display browsability when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. A light-emitting apparatus of one embodiment of the present invention can be used for the display panel 9311.

EXAMPLE 1

Synthesis Example 1

In this example, a method for synthesizing the organic compound of one embodiment of the present invention, 4,4'-(1,1-cyclohexane-diyl)bis[N,N-bis(4-cyclohexylbenzen-1-yl)aminobenzene] (abbreviation: TAPC-02) will be described. The structure of TAPC-02 is shown below.

[Chemical Formula 24]

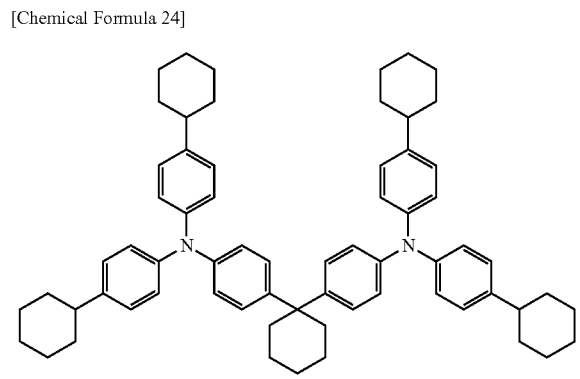 [SMILES: c1cc(N(c2ccc(C3CCCCC3)cc2)c2ccc(C3(c4ccc(N(c5ccc(C6CCCCC6)cc5)c5ccc(C6CCCCC6)cc5)cc4)CCCCC3)cc2)ccc1C1CCCCC1]

Step 1: Synthesis of 4,4'-(1,1-cyclohexane-diyl)bis[N,N-bis(4-cyclohexylbenzen-1-yl)aminobenzene]

Into a three-neck flask were put 5.3 g (20 mmol) of 1,1-bis(4-aminophenyl)cyclohexane, 21.0 g (88 mmol) of 4-cyclohexyl-1-bromobenzene, 25.4 g (264 mmol) of sodium tert-butoxide, and 400 mL of a xylene mixture, the mixture was degassed under reduced pressure, and then the air in the flask was replaced with nitrogen. The mixture was stirred while being heated to approximately 50° C. Then, 293 mg (0.8 mmol) of allylpalladium(II) chloride dimer (abbreviation: (Allyl)PdCl)$_2$) and 1128 mg (3.2 mmol) of di-tert-butyl(1-methyl-2,2-diphenylcyclopropyl)phosphine (product name: cBRIDP (registered trademark)) were added, and the mixture was heated and refluxed for 6 hours. After that, the temperature of the flask was lowered to approximately 60° C., approximately 4 mL of water was added, a precipitated solid was separated by filtration, and the solid was washed with toluene. The filtrate was concentrated, and the obtained xylene solution was purified by silica gel column chromatography. The obtained solution was concentrated to give a concentrated toluene solution. The toluene solution was dropped into ethanol for reprecipitation. The precipitate was filtrated at approximately 0° C. and the obtained solid was dried at approximately 75° C. under reduced pressure, so that 16.5 g of a target white solid was obtained in a yield of 92%. The synthesis scheme of Step 1 is shown below.

[Chemical Formula 29]

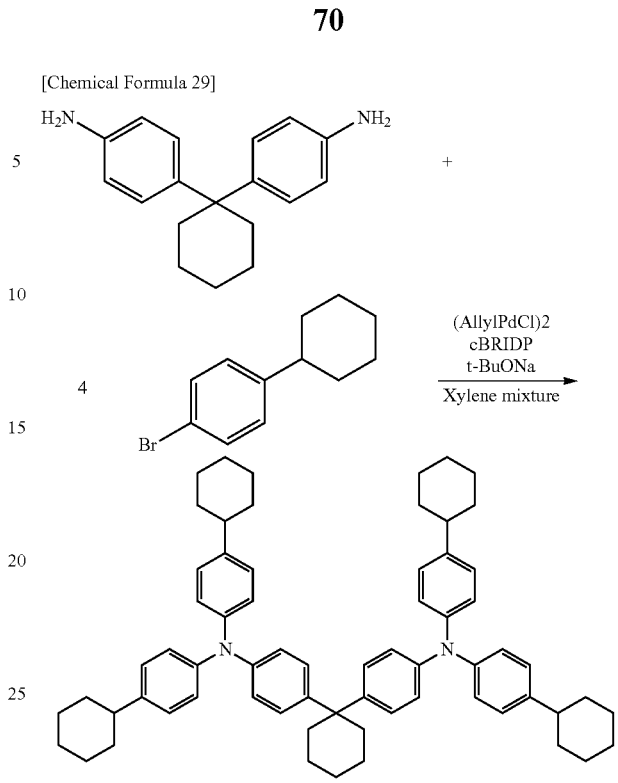

Figure 14A:
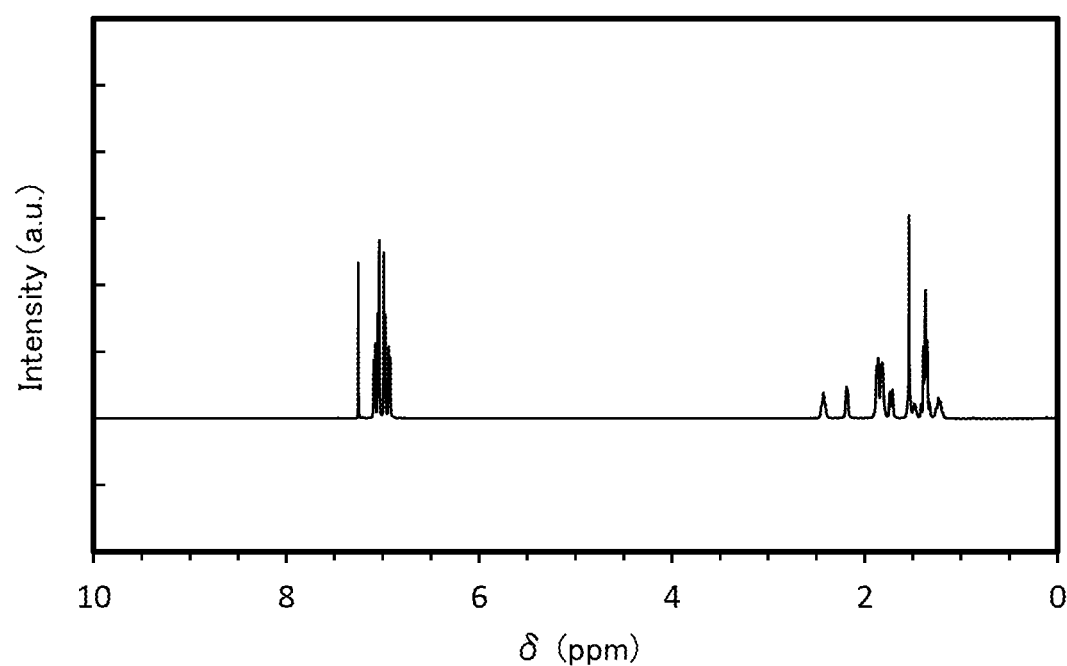
FIGS. 14A and 14B are $^1$H NMR charts of TAPC-02.
Figure 14B:
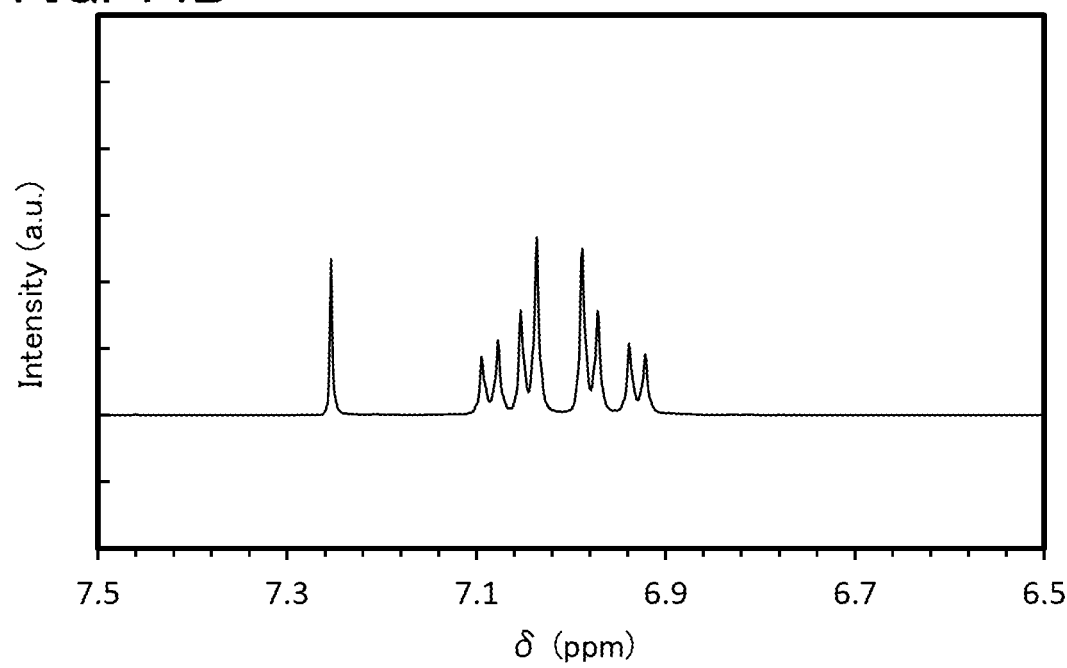

Analysis results by nuclear magnetic resonance spectroscopy ($^1$H-NMR) of the white solid obtained in Step 1 are shown below and FIG. 14. These results show that 4,4'-(1,1-cyclohexane-diyl)bis[N,N-bis(4-cyclohexylbenzen-1-yl)aminobenzene] was synthesized in Step 1 above.

$^1$H-NMR. δ (CDCl$_3$): 7.02-7.11 (m, 12H), 6.91-7.00 (m, 12H), 2.39-2.47 (brm, 4H), 2.16-2.21 (brm, 4H), 1.78-1.91 (brm, 16H), 1.69-1.76 (brm, 4H), 1.51-1.57 (brm, 4H), 1.45-1.51 (brm, 2H), 1.31-1.42 (brm, 16H), 1.17-1.28 (brm, 4H).

Next, by a train sublimation method, 6.0 g of the obtained solid was sublimated and purified. The sublimation purification was performed by heating at 355° C. under the conditions where the pressure was 3.0 Pa and the argon flow rate was 12.3 mL/min. After the sublimation purification, 4.5 g of a pale yellowish white solid was obtained at a collection rate of 74%.

Next, absorption spectra and emission spectra of a toluene solution and a solid thin film of TAPC-02 were measured. The solid thin film was formed over a quartz substrate by a vacuum evaporation method. For the measurement of the absorption spectra, UV-visible spectrophotometers (solution: V-550 manufactured by JASCO Corporation, thin film: U-4100 manufactured by Hitachi High-Technologies Corporation) were used. Note that the absorption spectrum of the solution was calculated by subtracting the absorption spectrum measured by putting only toluene in a quartz cell, and the absorption spectrum of the thin film was calculated from an absorbance ($-\log_{10}$[% T/(100−% R)]) obtained from a transmittance and a reflectance of the substrate and the thin film. Note that % T represents transmittance and % R represents reflectance. The emission spectra were measured using a fluorescence spectrophotometer (FS920 manufactured by Hamamatsu Photonics K.K.).

Figure 15:
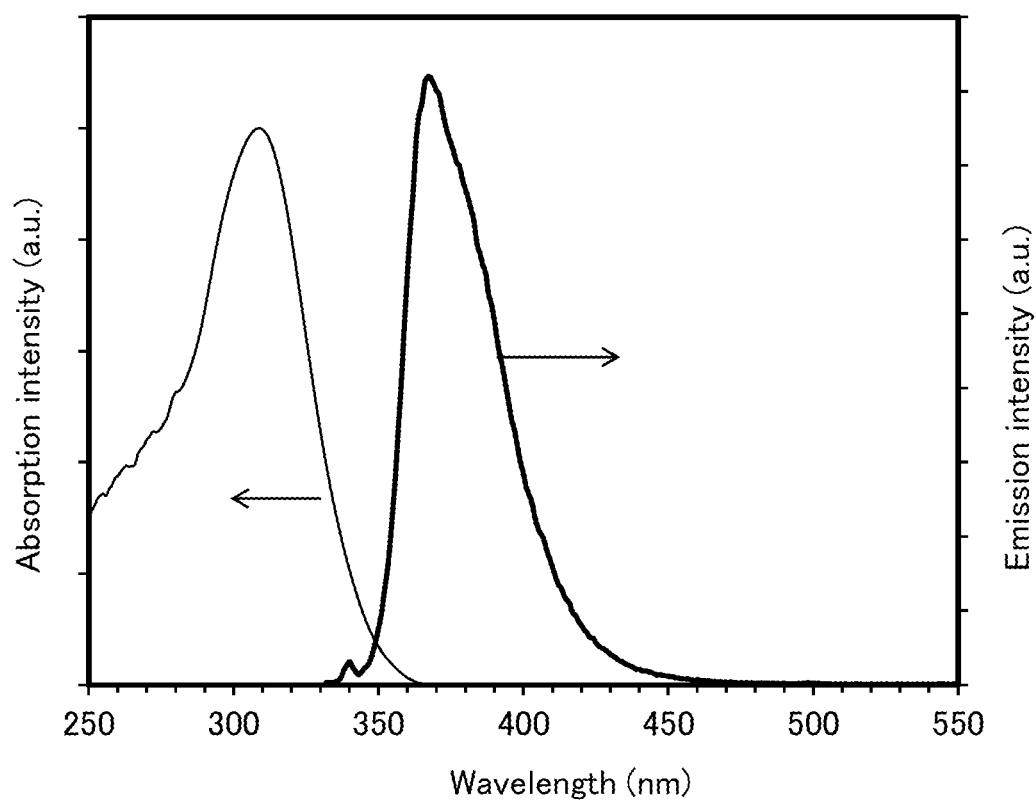
FIG. 15 is an absorption spectrum and an emission spectrum of TAPC-02 in a toluene solution.
Figure 16:
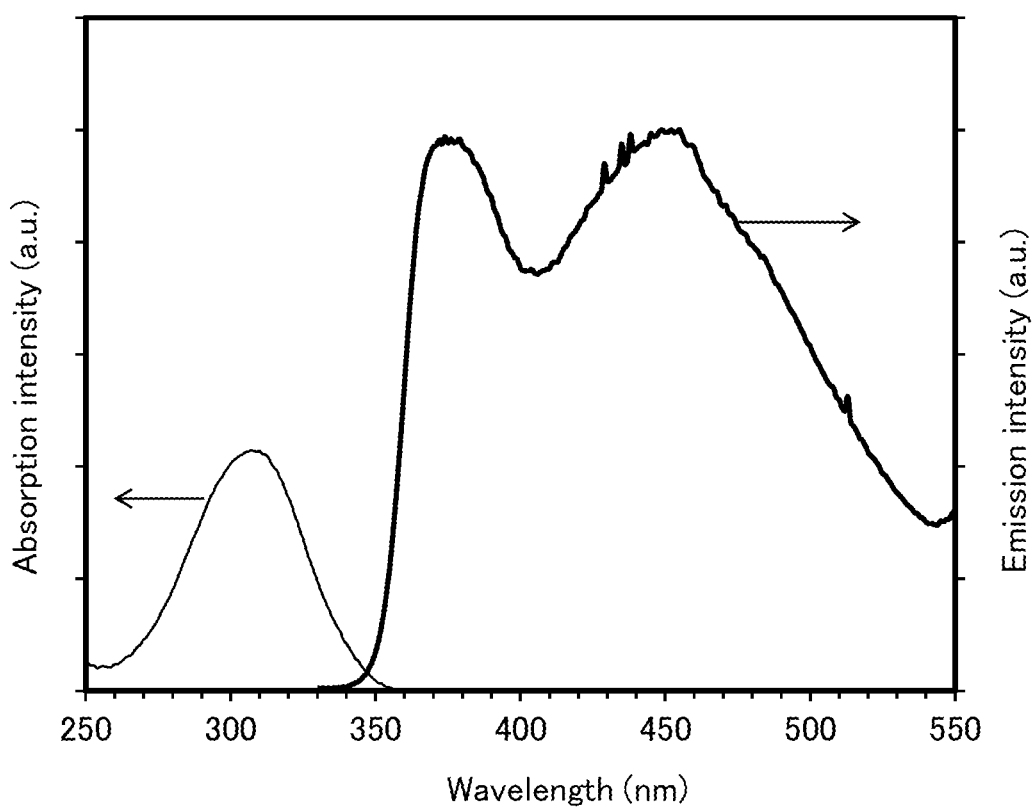
FIG. 16 is an absorption spectrum and an emission spectrum of TAPC-02 in a thin film state.

FIG. 15 shows the obtained measurement results of the absorption spectrum and the emission spectrum of the toluene solution. The horizontal axis represents wavelength and the vertical axes represent absorption intensity and emission intensity. FIG. 16 shows the measurement results of the absorption spectrum and the emission spectrum of the solid thin film.

Next, mass spectrometry of the organic compound TAPC-02 was performed by liquid chromatography mass spectrometry (abbreviation: LC/MS analysis).

In the LC/MS analysis, LC (liquid chromatography) separation was carried out with Acquity UPLC (registered trademark) manufactured by Waters Corporation, and MS analysis (mass spectrometry) was carried out with Xevo G2 Tof MS manufactured by Waters Corporation. Acquity UPLC BEH C4 (2.1×100 mm, 1.7 μm) was used as a column for the LC separation, and the column temperature was set to 40° C. As for mobile phases, a cetonitrile was used for Mobile Phase A and a 0.1% aqueous solution of formic acid was used for Mobile Phase B. A sample was prepared in such a manner that TAPC-02 was dissolved in toluene at a given concentration and the mixture was diluted with acetonitrile. The injection amount was 5.0 μL.

In the LC separation, the ratio of Mobile Phase A to Mobile Phase B was 95:5 for 10 minutes after the start (0 minutes) of the measurement.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z=899 which underwent the ionization under the above-described conditions was collided with an argon gas in a collision cell to dissociate into product ions. Energy (collision energy) for the collision with argon was set to 70 eV. The measurement mass range was set to m/z (mass-to-charge ratio)=100 to 1000. The detection result of the dissociated product ions by time-of-flight (TOF) MS are shown in FIG. 17.

Figure 17:
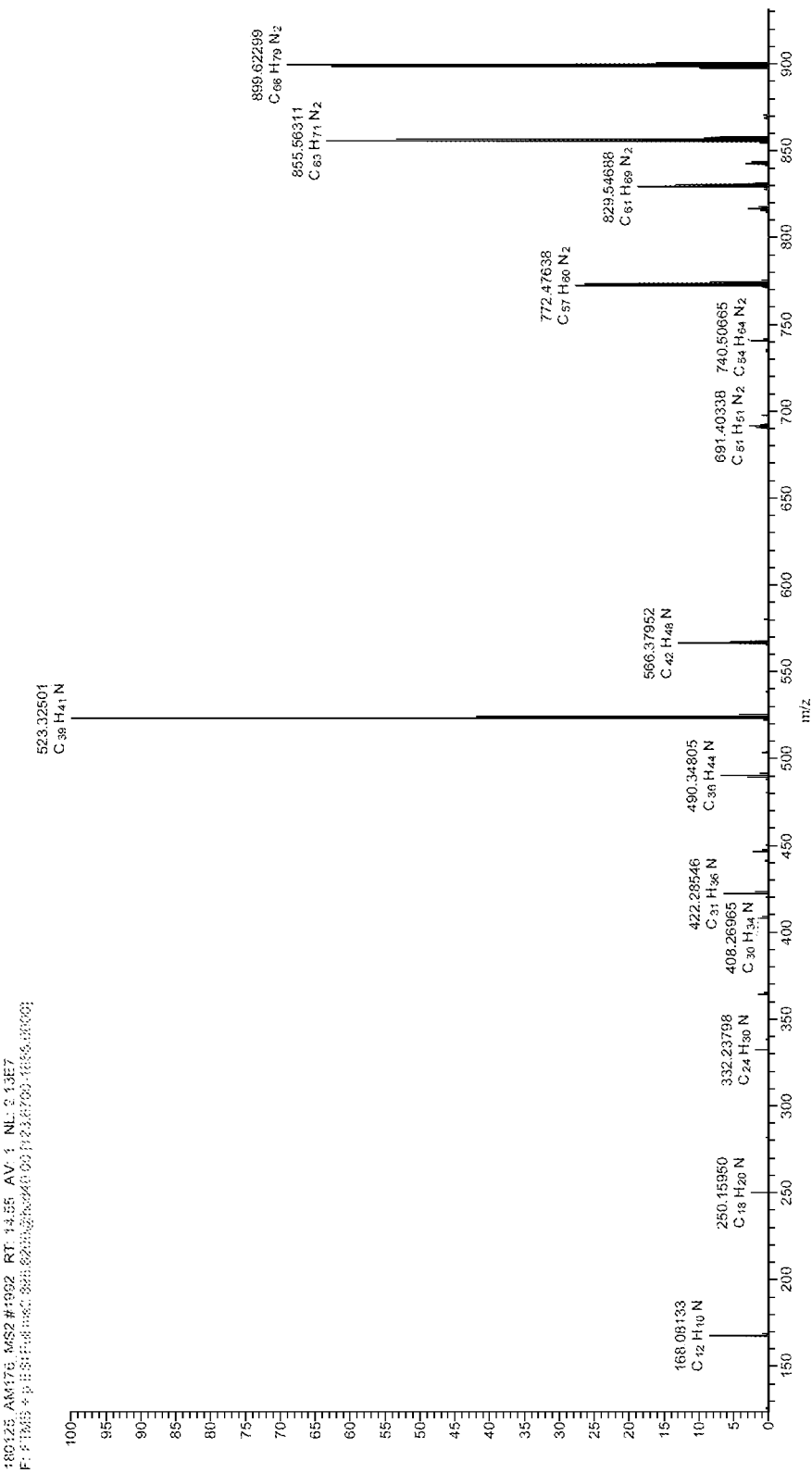
FIG. 17 is an MS spectrum of TAPC-02.

FIG. 17 shows that product ions of TAPC-02 are mainly detected around m/z=899. Note that the results shown in FIG. 17 exhibit characteristic results derived from TAPC-02 and therefore are important data for identifying TAPC-02 contained in a mixture.

Note that a fragment ion of m/z=566, which was observed in measurement with a collision energy of 70 eV, is estimated to be derived from 4,4'-(1,1-cyclohexane-diyl)[N-bis (4-cyclohexylbenzen-1-yl)aminobenzene][N'-(4-cyclohexylbenzen-1-yl)aminobenzene] generated in such a manner that a C—N bond of TAPC-02 was cut, and this is one characteristic of TAPC-02.

Figure 38:
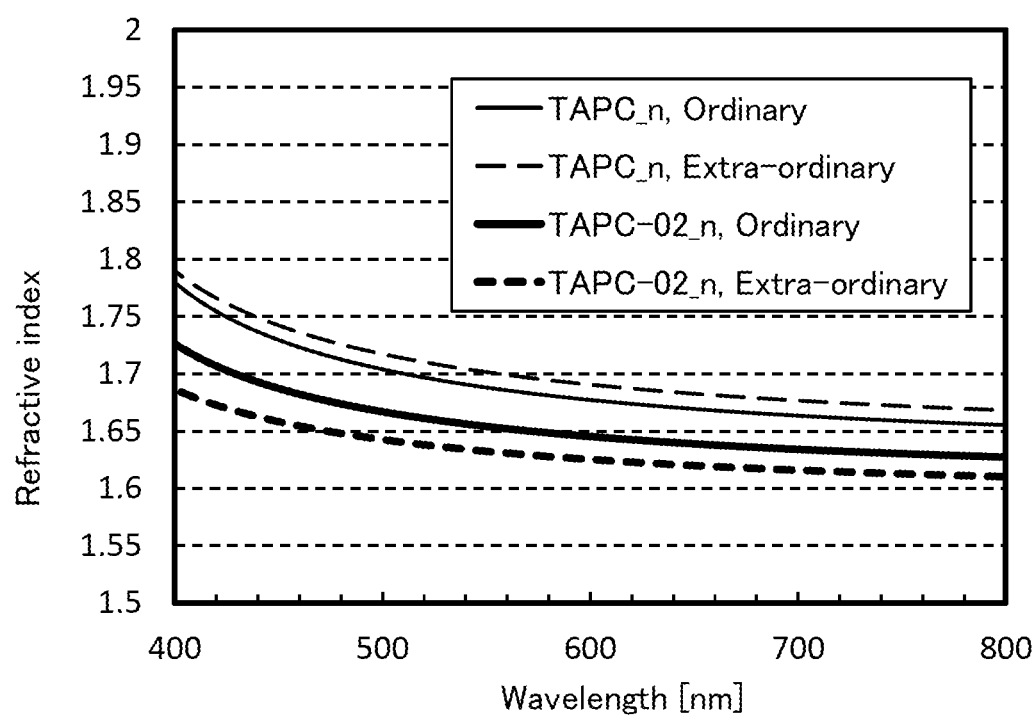
FIG. 38 is Refractive indeces of TAPC and TAPC-02 with respect to wavelength.

FIG. 38 shows the refractive index of TAPC-02 which was synthesized and the refractive index of 1,1-bis-(4-bis (4-methyl-phenyl)-amino-phenyl)-cyclohexane (abbreviation: TAPC) which is known as an organic compound having a low refractive index. Note that examples of a refractive index n includes a refractive index of an ordinary ray, n Ordinary, a refractive index of an extraordinary ray, n Extra-ordinary, and the average of them, n average. In this specification, the simple term "refractive index" may be rephrased as n average when anisotropy analysis is not performed. Note that n average is a value obtained by dividing the sum of n Extra-ordinary and 2 n Ordinary by 3.

As shown in FIG. 38, TAPC-02 which is the organic compound of one embodiment of the present invention was found to be an organic compound having an extremely low refractive index.

Next, the glass transition temperatures (Tg) of TAPC-02 and TAPC were measured with a differential scanning calorimeter (DSC). The measurement results of Tg were 119° C. for TAPC-02 and 85° C. for TAPC. This indicates that TAPC-02 has high heat resistance.

EXAMPLE 2

Synthesis Example 2

In this example, a method for synthesizing the organic compound of one embodiment of the present invention, 4,4'-(1,1-Cyclohexane-diyl)bis{N-(4-cyclohexylphenyl)N-[(4'-cyclohexyl)-1,1'-biphenyl-4-yl]aminobenzene} (abbreviation: TAPC-03) will be described. The structure of TAPC-03 is shown below.

[Chemical Formula 30]

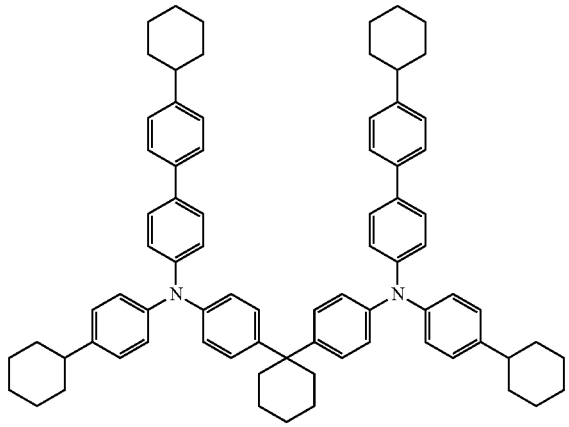

Step 1: Synthesis of 4,4'-(1,1-cyclohexane-diyl) bis{N-(4-cyclohexylphenyl)aminobenzene}

Into a three-neck flask were put 5.3 g (20 mmol) of 1,1-bis(4-aminophenyl)cyclohexane, 10.0 g (42 mmol) of 4-cyclohexyl-1-bromobenzene, 12.1 g (126 mmol) of sodium tert-butoxide, and 200 mL of a xylene mixture, the mixture was degassed under reduced pressure, and then the air in the flask was replaced with nitrogen. The mixture was stirred while being heated to approximately 50° C. Then, 150 mg (0.4 mmol) of allylpalladium(II) chloride dimer (abbreviation: (AllylPdCl)$_2$) and 660 mg (1.6 mmol) of dicyclohexyl(2',6'-dimethoxy-{1,1'-biphenyl}-2-yl)phosphine (abbreviation: SPhos) were added, and the mixture was heated and refluxed for 6 hours. After that, the temperature of the flask was lowered to approximately 60° C., approximately 2 mL of water was added, a precipitated solid was separated by filtration, and the solid was washed with toluene. The filtrate was concentrated, and the obtained xylene solution was purified by silica gel column chromatography. The obtained solution was concentrated to give a concentrated toluene solution. The toluene solution was dropped into ethanol for reprecipitation. The precipitate was filtrated at approximately 0° C. and the obtained solid was dried at approximately 75° C. under reduced pressure, so that 9.5 g of a target white solid was obtained in a yield of 81%. The synthesis scheme of Step 1 is shown below.

[Chemical Formula 31]

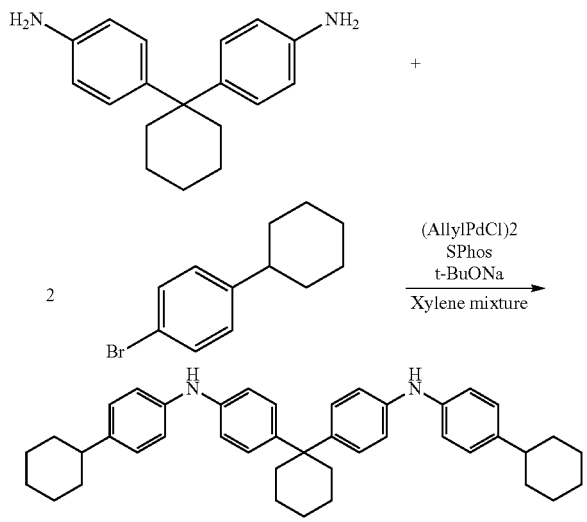

Figure 18A:
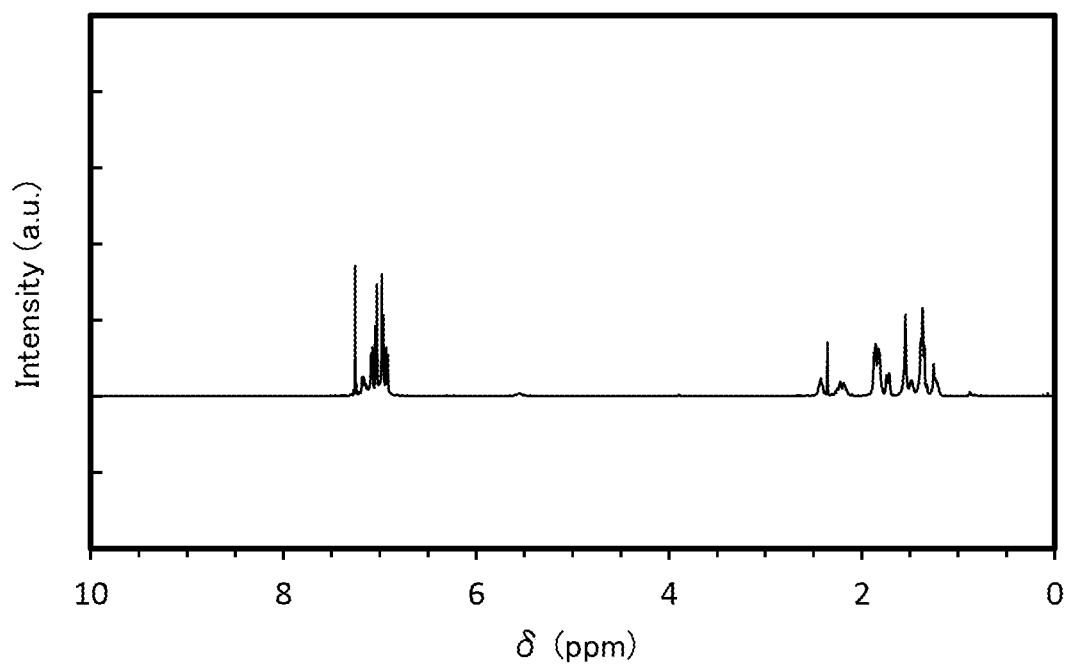
FIGS. 18A and 18B are $^1$H NMR charts of 4,4'-(1,1-cyclohexane-diyl)bis{N-(4-cyclohexylphenyl)aminobenzene}.
Figure 18B:
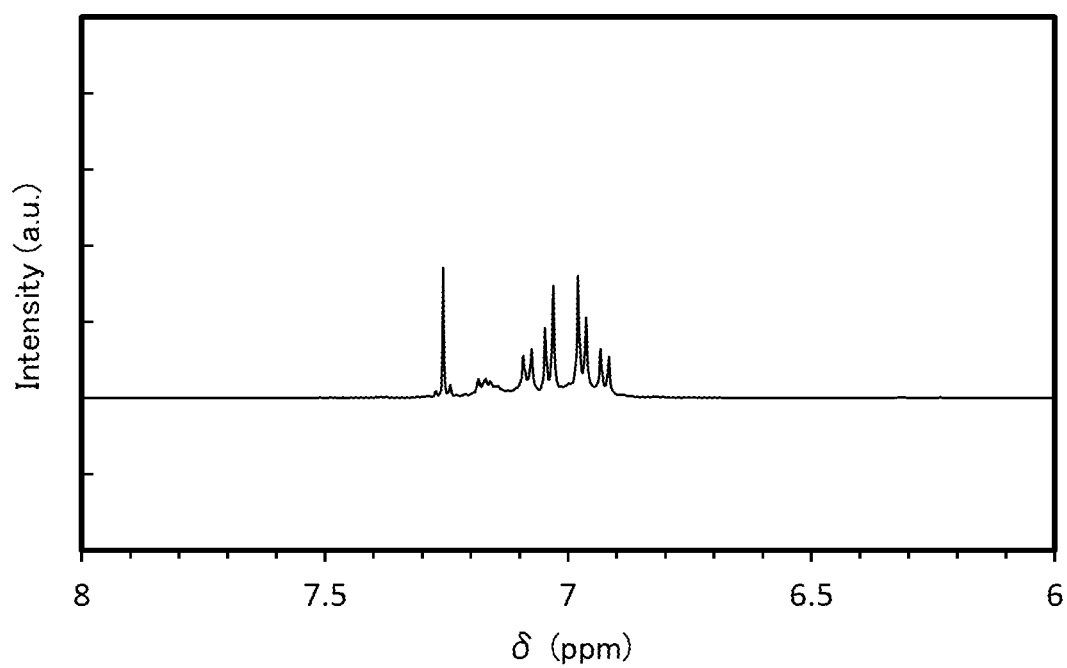

Analysis results by nuclear magnetic resonance spectroscopy ($^1$H-NMR) of the white solid obtained in Step 1 are shown below. FIG. 18 shows a $^1$H-NMR chart. These results show that the organic compound 4,4'-(1,1-cyclohexane-diyl)bis{N-(4-cyclohexylphenyl)aminobenzene} was synthesized in Step 1.

$^1$H-NMR. δ (CDCl$_3$): 7.02-7.11 (m, 8H), 6.91-6.99 (m, 8H), 5.55 (br, 2H), 2.39-2.47 (brm, 2H), 2.16-2.28 (brm, 4H), 1.76-1.91 (brm, 8H), 1.69-1.76 (brm, 2H), 1.52-1.60 (brm, 4H), 1.44-1.52 (brm, 2H), 1.31-1.44 (brm, 8H), 1.18-1.28 (brm, 4H).

Step 2: Synthesis of 4,4'-(1,1-Cyclohexane-diyl)bis{N-(4-cyclohexylphenyl)N-[(4'-cyclohexyl)-1,1'-biphenyl-4-yl]aminobenzene} (abbreviation: TAPC-03)

Into a three-neck flask were put 5.8 g (10 mmol) of 4,4'-(1,1-cyclohexane-diyl)bis{N-(4-cyclohexylphenyl)aminobenzene}, 5.4 g (20 mmol) of 4'-cyclohexyl-(1,1'-biphenyl)-4-chlorobenzene, 5.8 g (60 mmol) of sodium tert-butoxide, and 70 mL of a xylene mixture, the mixture was degassed under reduced pressure, and then the air in the flask was replaced with nitrogen. The mixture was stirred while being heated to approximately 50° C. Then, 73 mg (0.2 mmol) of allylpalladium(II) chloride dimer (abbreviation: (AllylPdCl)$_2$) and 280 mg (0.8 mmol) of di-tert-butyl(1-methyl-2,2-diphenylcyclopropyl)phosphine (abbreviation: cBRIDP) were added, and the mixture was heated and refluxed for 8 hours. After that, the temperature of the flask was lowered to approximately 60° C., approximately 2 mL of water was added, a precipitated solid was separated by filtration, and the solid was washed with toluene. The filtrate was concentrated, and the obtained xylene solution was purified by silica gel column chromatography. The obtained solution was concentrated to give a concentrated toluene solution. The toluene solution was dropped into ethanol for reprecipitation. The precipitate was filtrated at approximately 0° C. and the obtained solid was dried at approximately 75° C. under reduced pressure, so that 5.8 g of a target white solid was obtained in a yield of approximately 100%. The synthesis scheme of Step 2 is shown below.

[Chemical Formula 32]

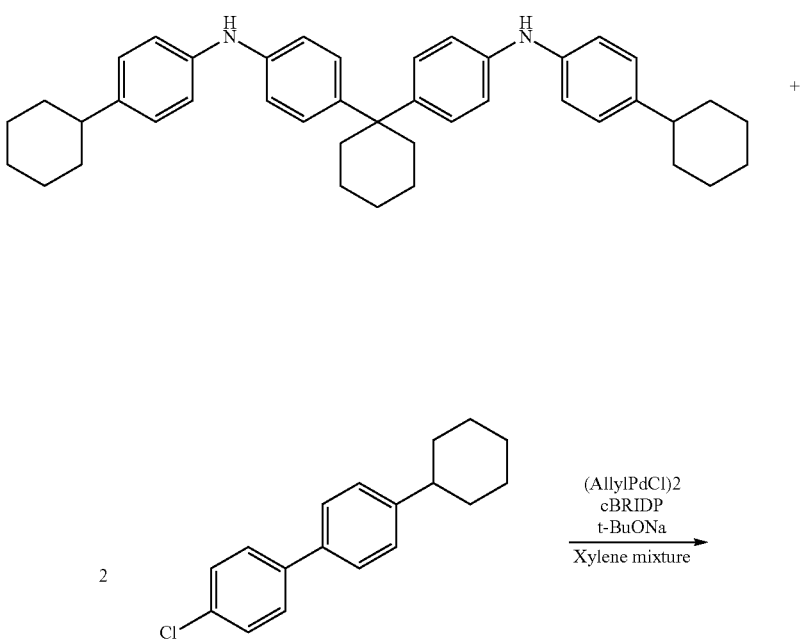

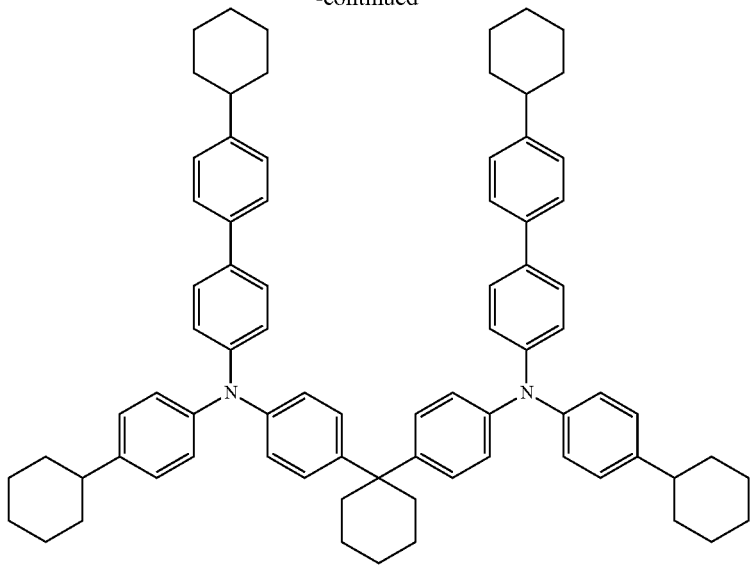

Figure 19A:
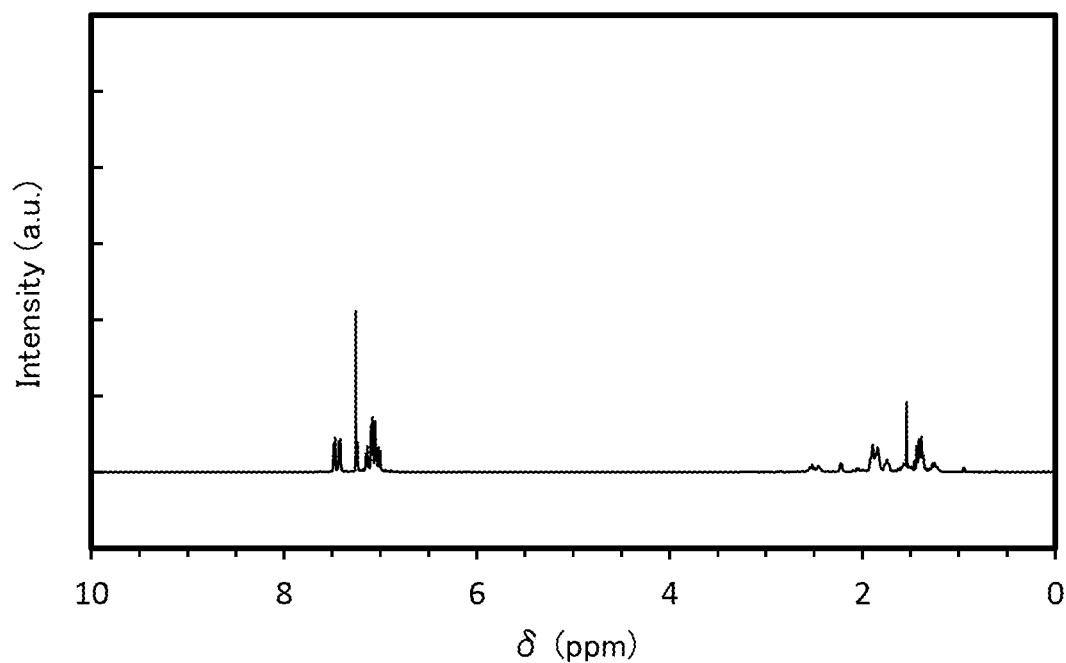
FIGS. 19A and 19B are $^1$H NMR charts of TAPC-03.
Figure 19B:
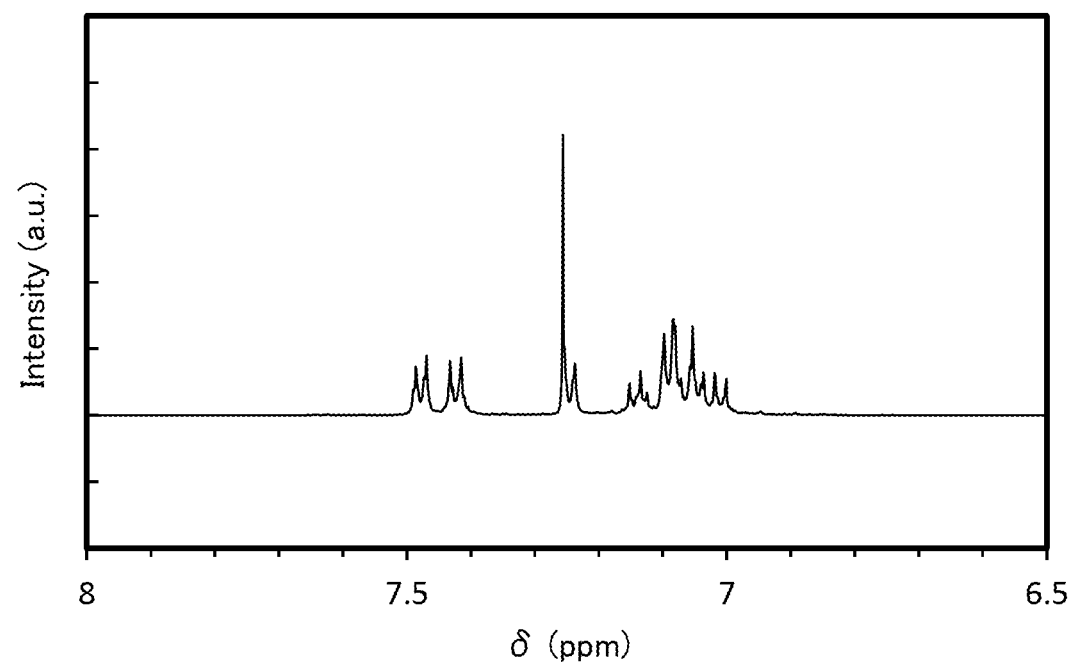

Analysis results by nuclear magnetic resonance spectroscopy ($^1$H-NMR) of the white solid obtained in Step 2 are shown below. FIG. 19 shows an $^1$H-NMR chart. These results show that the organic compound 4,4'-(1,1-Cyclohexane-diyl)bis{N-(4-cyclohexylphenyl)N-[(4'-cyclohexyl)-1,1'-biphenyl-4-yl]aminobenzene} (abbreviation: TAPC-03) was synthesized in Step 2.

$^1$H-NMR. δ (CDCl$_3$): 7.46-7.50 (m, 4H), 7.40-7.45 (m, 4H), 7.23-7.26 (m, 4H), 6.99-7.17 (brm, 20H), 2.42-2.59 (brm, 4H), 2.19-2.25 (brm, 2H), 1.79-1.95 (brm, 16H), 1.70-1.79 (brm, 4H), 1.32-1.64 (brm, 24H), 1.18-1.32 (brm, 4H).

EXAMPLE 3

In this example, a light-emitting device 1 of one embodiment of the present invention and a comparative light-emitting device 1 will be described. The structural formulae of organic compounds used in the light-emitting device 1 and the comparative light-emitting device 1 are shown below.

[Chemical Formulae 33]

(i)

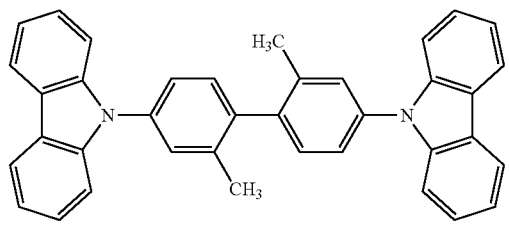

dmCBP (ii)

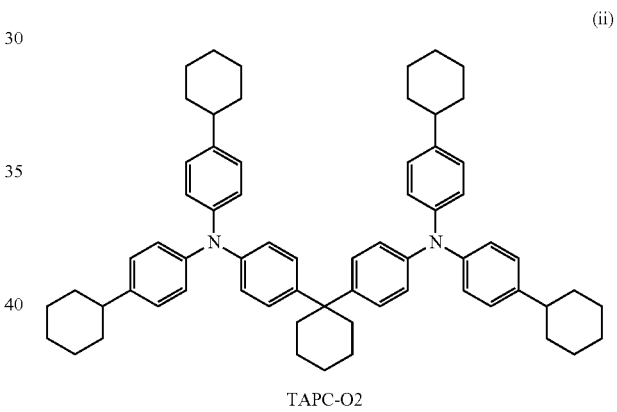

TAPC-O2

(iii)

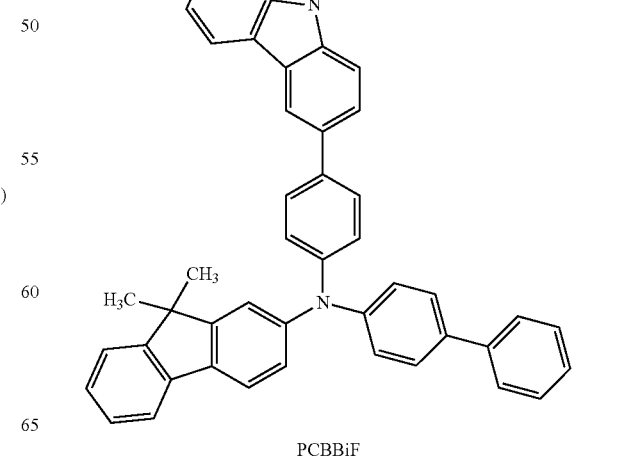

PCBBiF

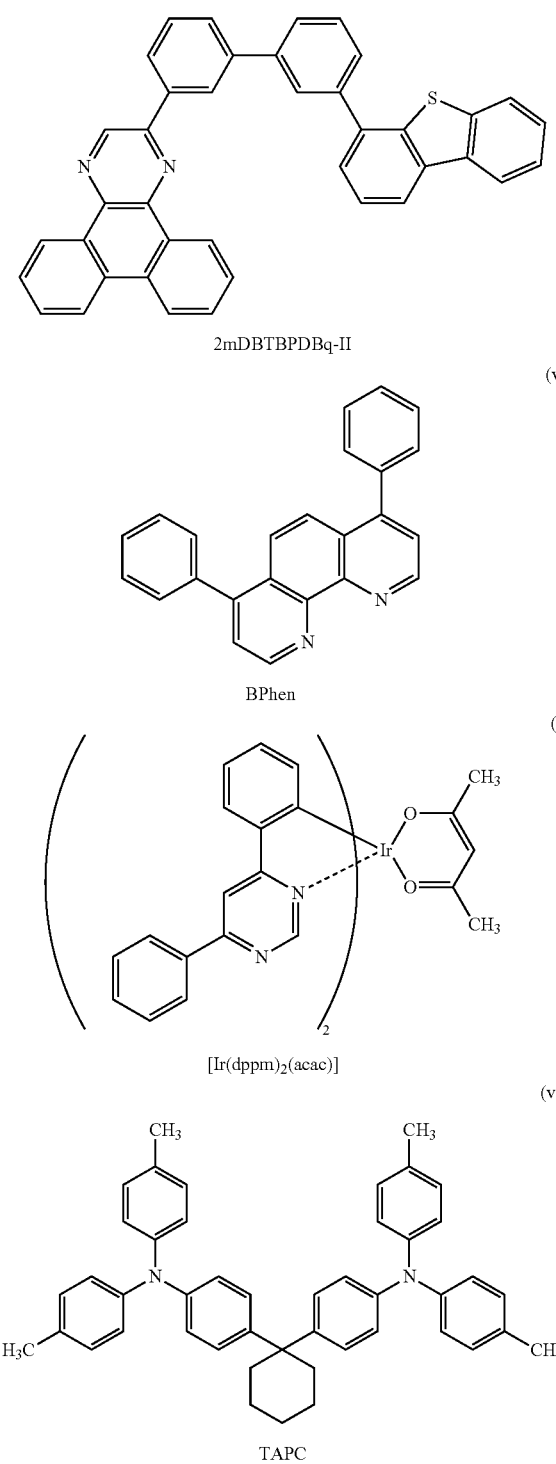

washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate over which the first electrode 101 was formed was fixed to a substrate holder provided in the vacuum evaporation apparatus so that the surface over which the first electrode 101 was formed faced downward, and 4,4'-bis(9-carbazolyl)-2,2'-dimethyl-biphenyl (abbreviation: dmCBP) represented by the structural formula (i) and molybdenum(VI) oxide were co-evaporated over the first electrode 101 to have a weight ratio of 2:0.5 (=dmCBP: MoOx) to a thickness of 10 nm by an evaporation method using resistance heating, whereby the hole-injection layer 111 was formed.

Next, 4,4'-(1,1-cyclohexane-diyl)bis[N,N-bis(4-cyclohexylbenzen-1-yl)aminobenzene] (abbreviation: TAPC-02) represented by the above structural formula (ii) was deposited by evaporation to a thickness of 65 nm over the hole-injection layer 111, and then, N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by the above structural formula (iii) was deposited by evaporation to a thickness of 5 nm, whereby the hole-transport layer 112 was formed.

Subsequently, 2-[3'-(dibenzothiophen-4-yl)biphenyl-3-yl]dibenzo[f,h]quinoxaline (abbreviation: 2mDBTBPDBq-II) represented by the above structural formula (iv), PCBBiF, and (acetylacetonato)bis(4,6-diphenylpyrimidinato)iridium (III) (abbreviation: [Ir(dppm)$_2$(acac)]) represented by the structural formula (v) were deposited by co-evaporation to a thickness of 20 nm at a weight ratio of 0.7:0.3:0.06 (=2mDBTBPDBq-II: PCBBiF: [Ir(dppm)$_2$(acac)]), and then deposited by co-evaporation to a thickness of 20 nm at a weight ratio of 0.8:0.2:0.06 (=2mDBTBPDBq-II: PCBBiF: [Ir(dppm)$_2$(acac)]), so that the light-emitting layer 113 was formed.

After that, over the light-emitting layer 113, 2mDBTBPDBq-II was deposited by evaporation to a thickness of 10 nm, and bathophenanthroline (abbreviation: BPhen) represented by the above structural formula (vi) was deposited by evaporation to a thickness of 5 nm, whereby the electron-transport layer 114 was formed.

After the formation of the electron-transport layer 114, lithium fluoride (LiF) and BPhen were deposited by co-evaporation to a thickness of 35 nm q a weight ratio of 0.75:0.25 (=LiF: BPhen) to form the electron-injection layer 115, and then aluminum was deposited by evaporation to a thickness of 200 nm to form the second electrode 102, whereby the light-emitting device 1 of this example was fabricated.

(Fabrication Method of Light-Emitting Device 1)

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting device over the substrate, the surface of the substrate was (Fabrication Method of Comparative Light-Emitting Device 1)

The comparative light-emitting device 1 was fabricated in a manner similar to that of the light-emitting device 1, except that the layer formed of TAPC-02 in the hole-transport layer 112 of the light-emitting device 1 was replaced with 1,1-bis-(4-bis(4-methyl-phenyl)-amino-phenyl)-cyclohexane (abbreviation: TAPC) represented by the above structural formula (vii) and the film thickness was set to 70 nm.

Figure 24:
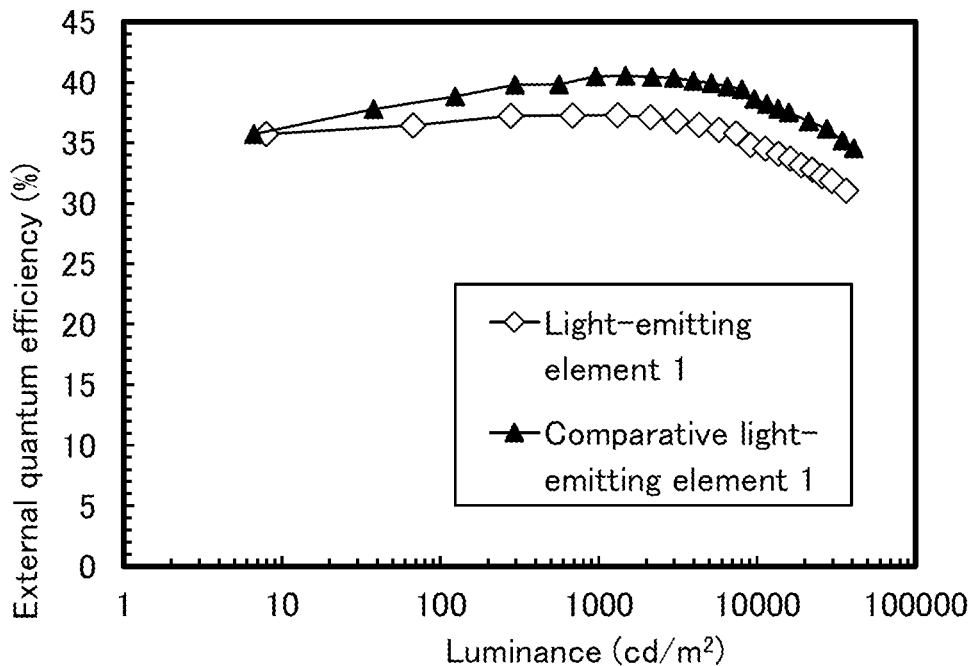
FIG. 24 is External quantum efficiency—luminance characteristics of the light-emitting device 1 and the comparative light-emitting device 1.

The device structures of the light-emitting device 1 and the comparative light-emitting device 1 are listed in the following table.

ciency in FIG. 24 shows values under the assumption of Lambertian, and for external quantum efficiency in the table below, the true values obtained by correcting deviation with respect to Lambertian distribution after measuring the angular dependency of an emission spectrum are adopted.

TABLE 2

|  | Voltage (V) | Current (mA) | Current density (mA/cm$^2$) | Chromaticity x | Chromaticity y | Current efficiency (cd/A) | External quantum efficiency (%) |
| --- | --- | --- | --- | --- | --- | --- | --- |
| Light-emitting device 1 | 2.9 | 0.04 | 1.0 | 0.57 | 0.43 | 95.8 | 39.0 |
| Comparative light-emitting device 1 | 2.6 | 0.03 | 0.8 | 0.57 | 0.43 | 87.4 | 36.7 |

TABLE 1

| Electron-injection layer | 35 nm | LiF:BPhen (0.75:0.25[vol %]) |
| --- | --- | --- |
| Electron-transport layer | 5 nm | BPhen |
| | 10 nm | 2mDBTBPDBq-II |
| Light-emitting layer | 20 nm | 2mDBTBPDBq-II:PCBBiF:Ir(dppm)$_2$(acac) (0.8:0.2:0.06) |
| | 20 nm | 2mDBTBPDBq-II:PCBBiF:Ir(dppm)$_2$(acac) (0.7:0.3:0.06) |
| Hole-transport layer | 5 nm *1 | PCBBiF *2 |
| Hole-injection layer | 10 nm | dmCBP:MoOx(2:0.5) |

*1 Light-emitting device 1: 65 nm, Comparative light-emitting device 1: 70 nm
*2 Light-emitting device 1: TAPC-O2, Comparative light-emitting device 1: TAPC Each of the light-emitting device 1 and the comparative light-emitting device 1 was subjected to sealing with a glass substrate (a sealing material was applied to surround the device, followed by UV treatment and one-hour heat treatment at 80° C. at the time of sealing) in a glove box containing a nitrogen atmosphere so that the light-emitting device is not exposed to the air. Then, initial characteristics of these light-emitting devices were measured. Note that the glass substrate over which the light-emitting device was formed was not subjected to particular treatment for improving outcoupling efficiency.

Figure 20:
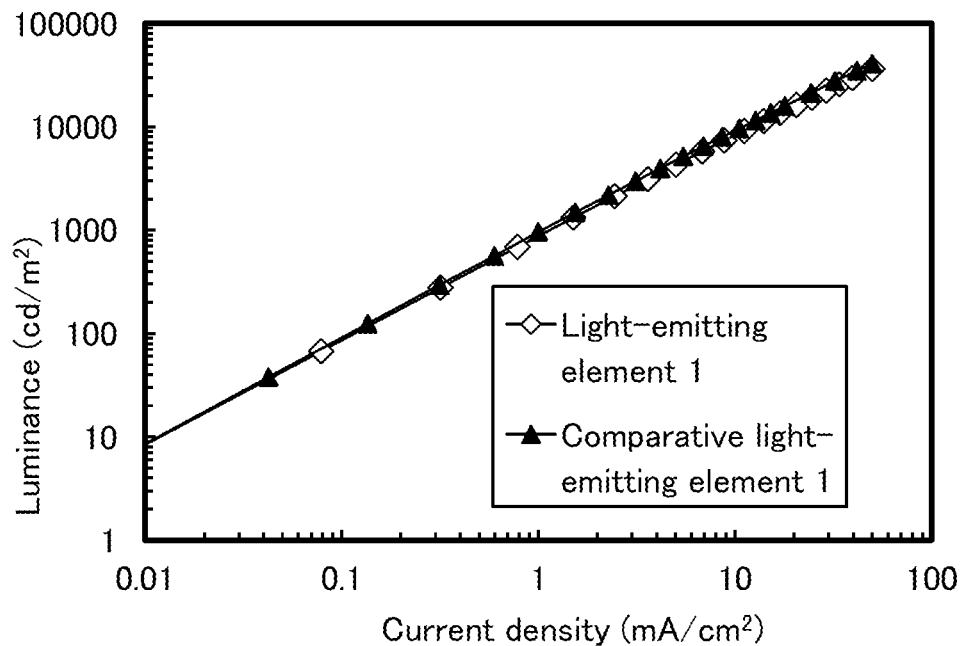
FIG. 20 is Luminance—current density characteristics of a light-emitting device 1 and a comparative light-emitting device 1.
Figure 21:
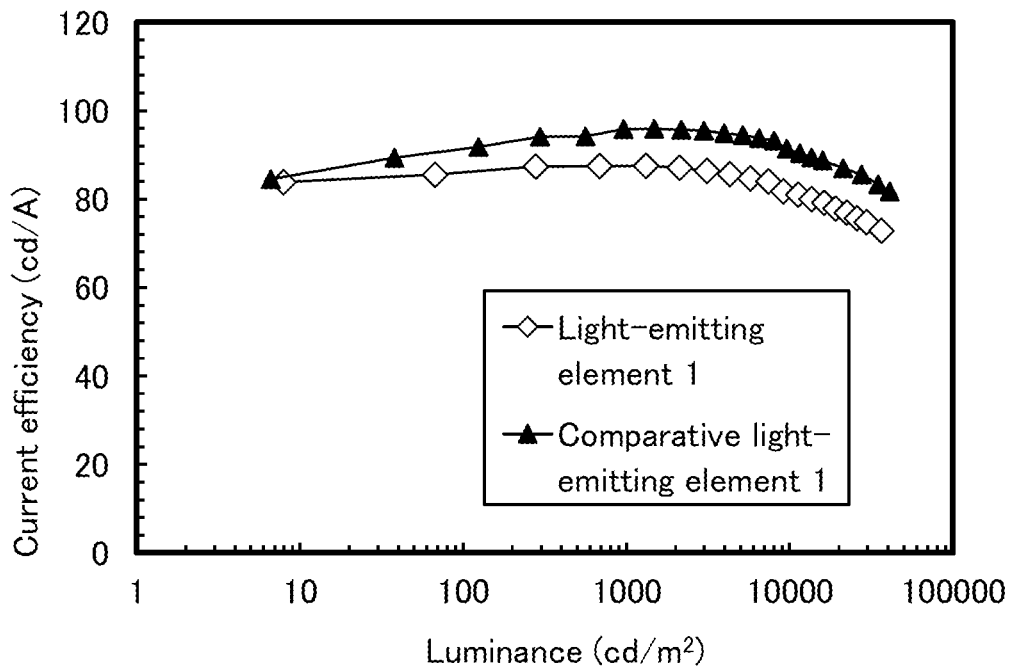
FIG. 21 is Current efficiency—luminance characteristics of the light-emitting device 1 and the comparative light-emitting device 1.
Figure 22:
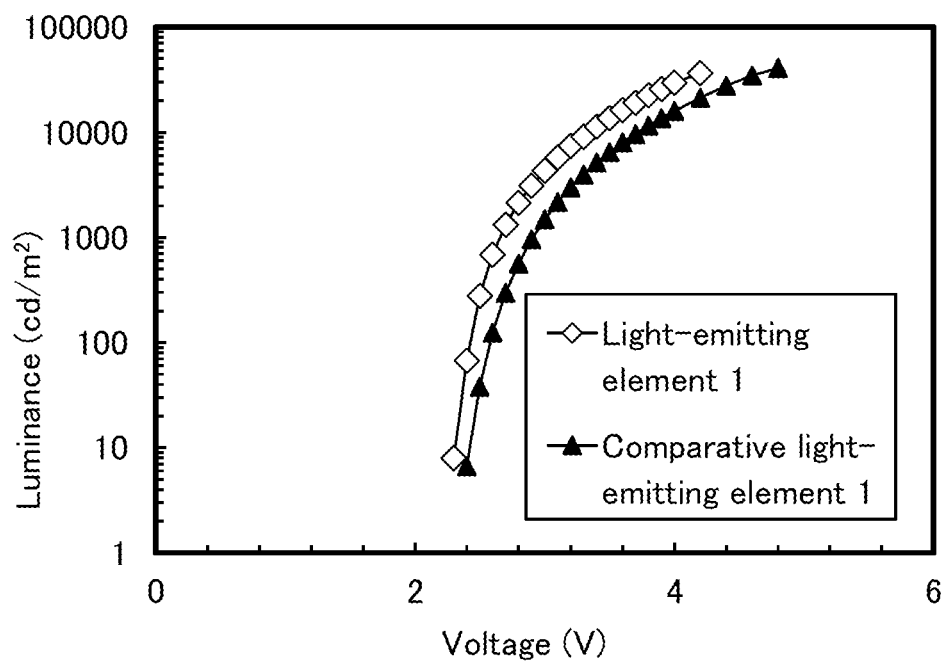
FIG. 22 is Luminance—voltage characteristics of the light-emitting device 1 and the comparative light-emitting device 1.
Figure 23:
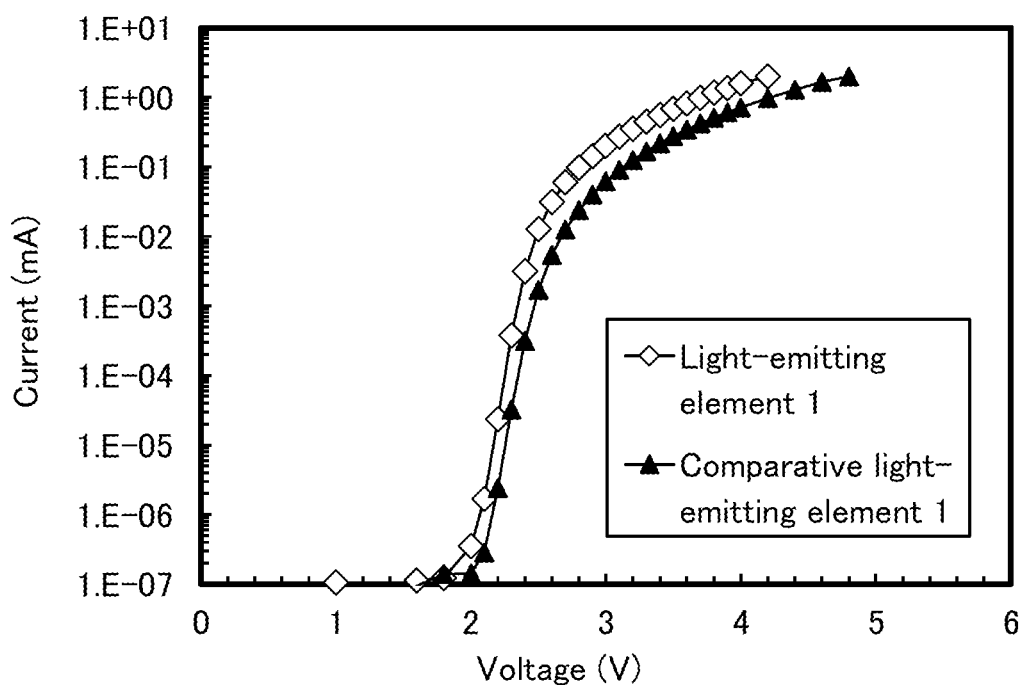
FIG. 23 is Current—voltage characteristics of the light-emitting device 1 and the comparative light-emitting device 1.
Figure 25:
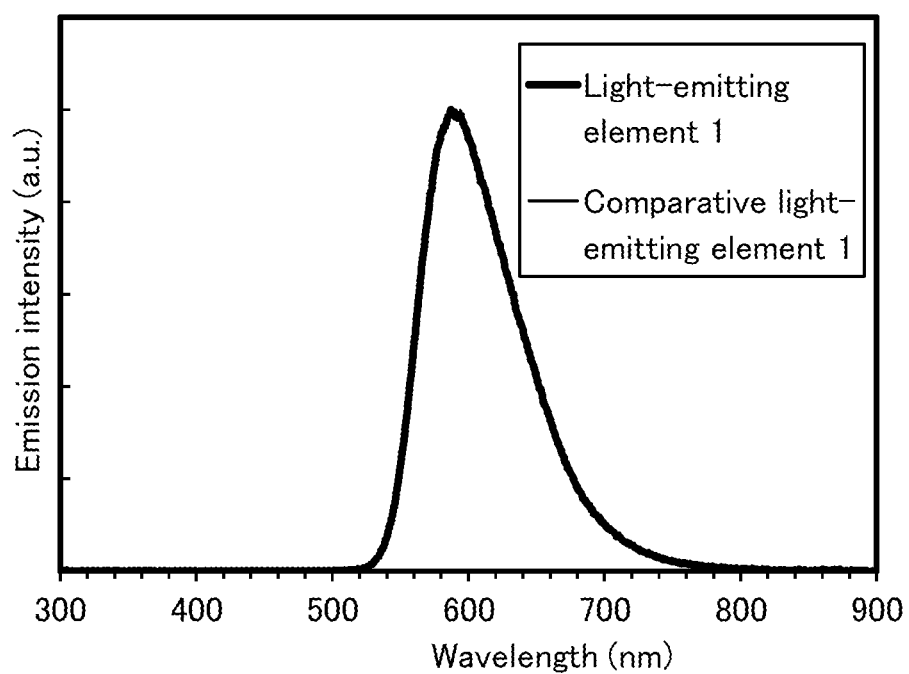
FIG. 25 is Emission spectra of the light-emitting device 1 and the comparative light-emitting device 1.

FIG. 20 shows the luminance-current density characteristics of the light-emitting device 1 and the comparative light-emitting device 1; FIG. 21, the current efficiency-luminance characteristics; FIG. 22, the luminance-voltage characteristics; FIG. 23, the current-voltage characteristics; FIG. 24, the external quantum efficiency-luminance characteristics; and FIG. 25, the emission spectra. In addition, Table 2 shows the main characteristics of the light-emitting devices at around 1000 cd/m$^2$. Note that luminance and CIE chromaticity were measured with a luminance colorimeter (BM-5A manufactured by TOPCON TECHNOHOUSE CORPORATION), and electroluminescence spectra were measured with a multi-channel spectrometer (PMA-11 manufactured by Hamamatsu Photonics K.K.). FIG. 25 shows that the emission spectra of the light-emitting device 1 and the comparative light-emitting device 1 considerably overlap with each other, and that the optical path lengths based on the product of the film thickness and the refractive index in the light-emitting device 1 and the comparative light-emitting device 1 are substantially the same. Accordingly, it can be said that strict comparison between the comparative light-emitting device 1 and the light-emitting device 1 is possible. Note that the external quantum effi- It was found from FIG. 20 to FIG. 25 and Table 2 that the light-emitting device 1 of one embodiment of the present invention has high emission efficiency because it includes, in the hole-transport layer, a layer formed of TAPC-O2 which is the organic compound of one embodiment of the invention, whose refractive index is lower than that of TAPC.

EXAMPLE 4

In this example, a light-emitting device 2 of one embodiment of the present invention will be described. Structural formulae of organic compounds used in the light-emitting device 2 are shown below.

[Chemical Formulae 34]

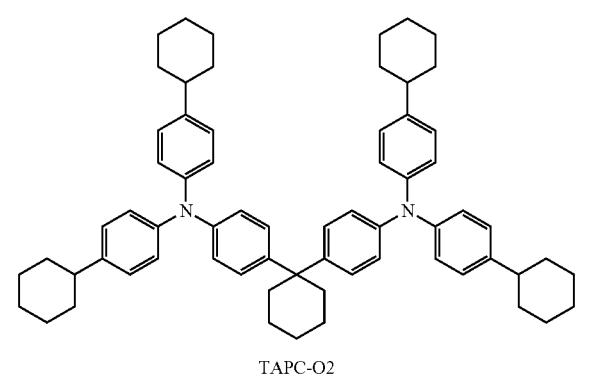

(ii)

TAPC-O2

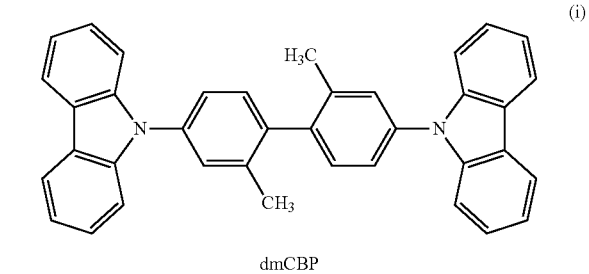

(i)

dmCBP

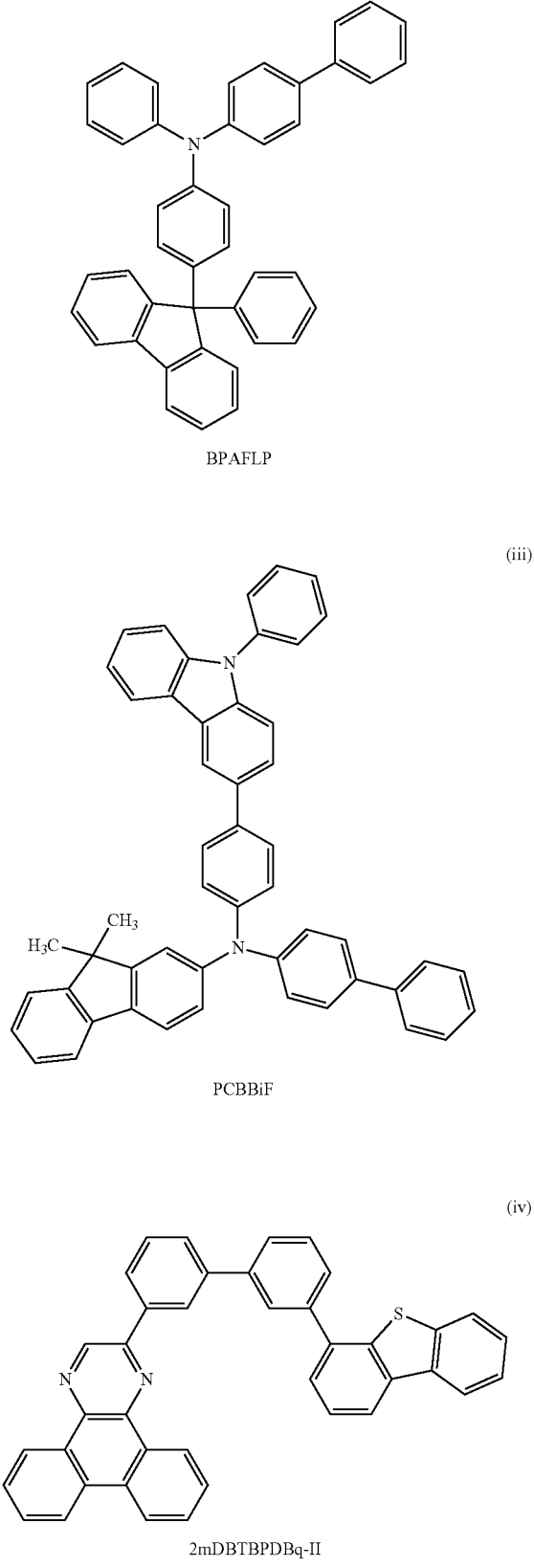

(Fabrication Method of Light-Emitting Device 2)

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate over which the first electrode 101 was formed was fixed to a substrate holder provided in the vacuum evaporation apparatus so that the surface over which the first electrode 101 was formed faced downward, and 4,4'-(1,1-cyclohexane-diyl)bis[N,N-bis(4-cyclohexyl-benzen-1-yl)aminobenzene] (abbreviation: TAPC-02) represented by the above structural formula (ii) and molybdenum (VI) oxide were co-evaporated over the first electrode 101 to have a weight ratio of 2:0.5 (=TAPC-02: molybdenum oxide) to a thickness of 50 nm by an evaporation method using resistance heating, and then, 4,4'-bis(9-carbazole)-2,2'-dimethyl-biphenyl (abbreviation: dmCBP) represented by the above structural formula (i) and molybdenum(VI) oxide were co-evaporated to have a weight ratio of 2:0.5 (=dmCBP: MoOx) to a thickness of 5 nm, whereby the hole-injection layer 111 was formed.

Next, 4-phenyl-4'-(9-phenylfluoren-9-yl)triphenylamine (abbreviation: BPAFLP) represented by the above structural formula (viii) was deposited by evaporation to a thickness of 20 nm over the hole-injection layer 111 to form the hole-transport layer 112.

Subsequently, 2-[3'-(dibenzothiophen-4-yl)biphenyl-3-yl]dibenzo[f,h]quinoxaline (abbreviation: 2mDBTBPDBq-II) represented by the above structural formula (iv), N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by the above structural formula (iii), and (acetylacetonato)bis(4,6-diphenylpyrimidinato)iridium(III) (abbreviation: [Ir(dppm)$_2$(acac)]) represented by the above structural formula (v) were deposited by co-evaporation to a thickness of 20 nm at a weight ratio of 0.7:0.3:0.06 (=2mDBTBPDBq-II: PCBBiF: [Ir(dppm)$_2$(acac)]), and then deposited by co-evaporation to a thickness of 20 nm at a weight ratio of 0.8:0.2:0.06 (=2mDBTBPDBq-II: PCBBiF: [Ir(dppm)$_2$(acac)]), so that the light-emitting layer 113 was formed.

After that, over the light-emitting layer 113, 2mDBTBPDBq-II was deposited to a thickness of 10 nm by evaporation, and bathophenanthroline (abbreviation: BPhen) represented by the above structural formula (vi) was deposited to a thickness of 5 nm by evaporation, whereby the electron-transport layer 114 was formed.

After the formation of the electron-transport layer 114, lithium fluoride (LiF) and BPhen were deposited by co-evaporation to a thickness of 35 nm to have a weight ratio of 0.75:0.25 (=LiF: BPhen) to form the electron-injection layer 115, and then aluminum was deposited by evaporation to a thickness of 200 nm to form the second electrode 102, whereby the light-emitting device 2 of this example was fabricated.

The device structure of the light-emitting device 2 is shown in the following table.

TABLE 3

| Electron-injection layer | 35 nm | LiF:BPhen (0.75:0.25[vol %]) |
|---|---|---|
| Electron-transport layer | 5 nm | BPhen |
| | 10 nm | 2mDBTBPDBq-II |
| Light-emitting layer | 20 nm | 2mDBTBPDBq-II:PCBBiF:Ir(dppm)$_2$(acac) (0.7:0.3:0.06) |
| | 20 nm | 2mDBTBPDBq-II:PCBBiF:Ir(dppm)$_2$(acac) (0.8:0.2:0.06) |
| Hole-transport layer | 20 nm | BPAFLP |
| Hole-injection layer | 5 nm | dmCBP:MoOx (2:0.5) |
| | 50 nm | TAPC-02:MoOx (2:0.5) |

The light-emitting device 3 was sealed using a glass substrate in a glove box containing a nitrogen atmosphere so as not to be exposed to the air (a sealant was applied to surround the device, and UV treatment and 1-hour heat treatment at 80° C. were performed in sealing). Then, initial characteristics of the light-emitting device 2 were measured. Note that the glass substrate over which the light-emitting device was formed was not subjected to particular treatment for improving outcoupling efficiency.

Figure 26:
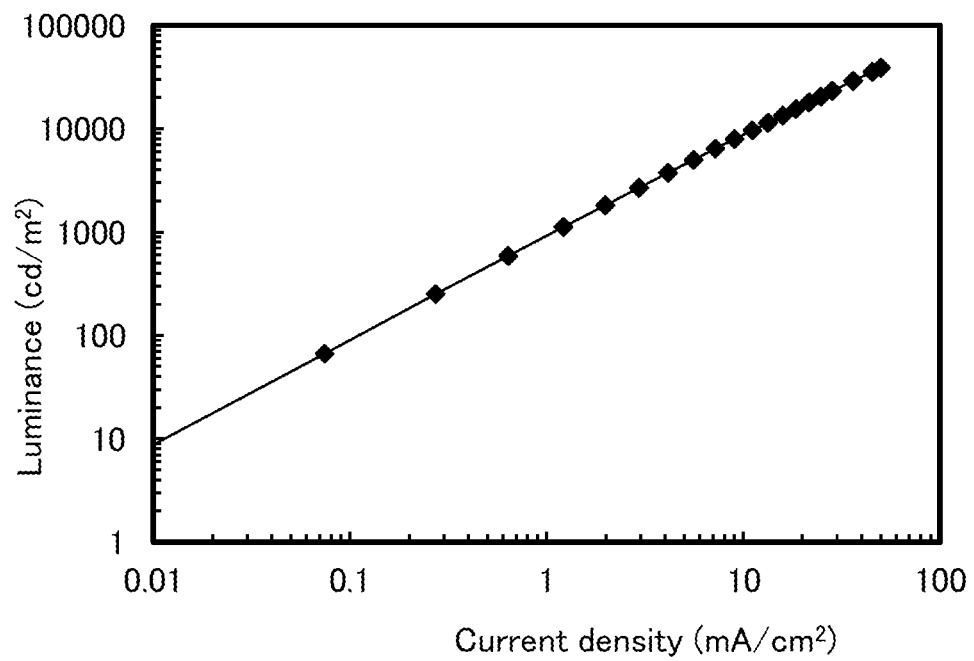
FIG. 26 is Luminance—current density characteristics of a light-emitting device 2.
Figure 27:
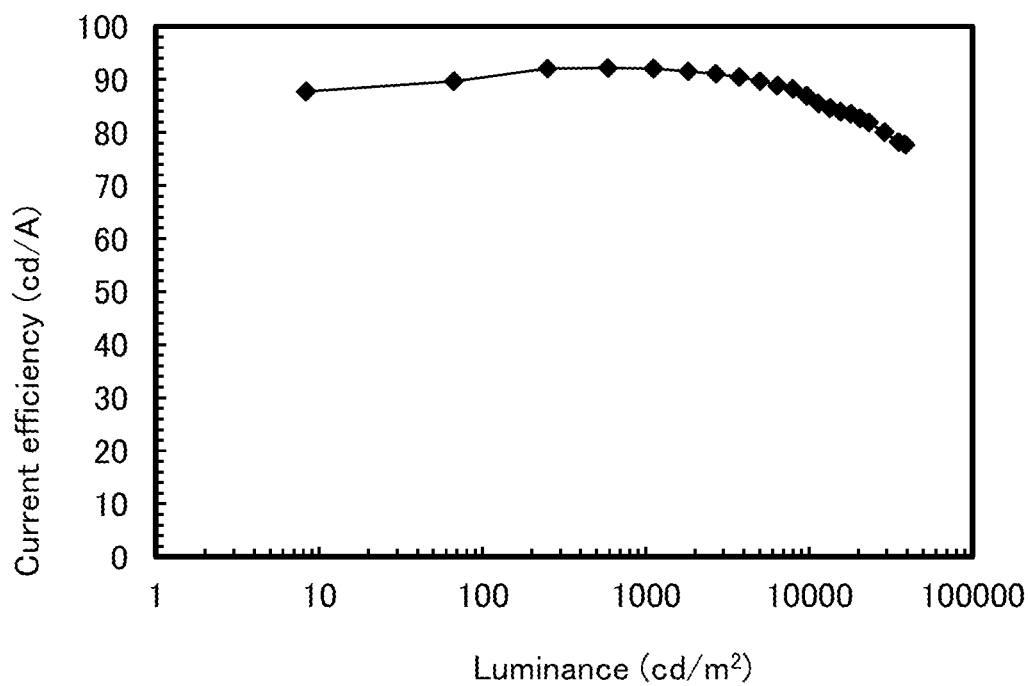
FIG. 27 is Current efficiency—luminance characteristics of the light-emitting device 2.
Figure 28:
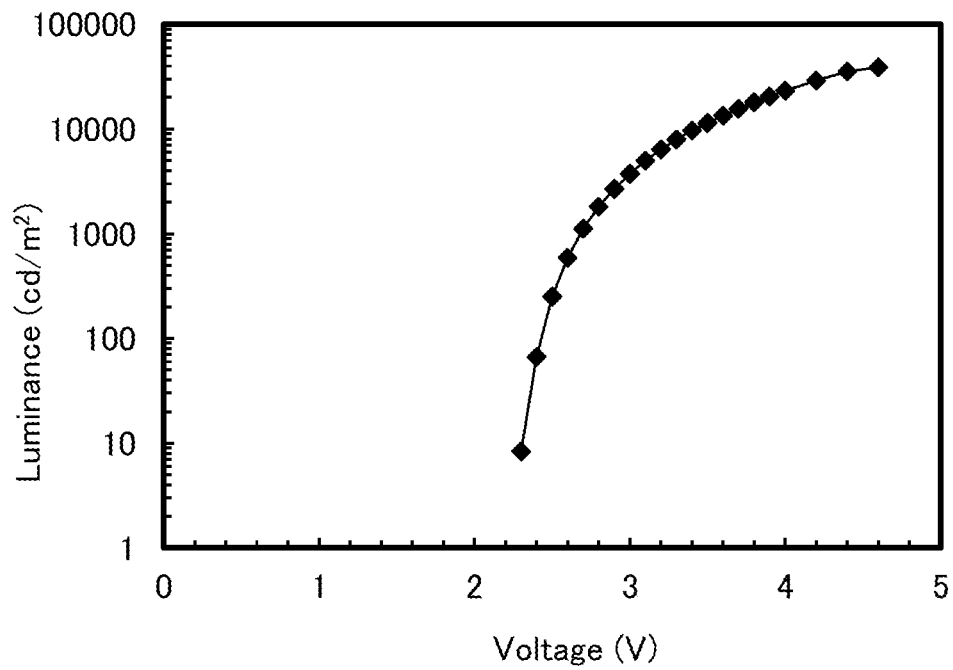
FIG. 28 is Luminance—voltage characteristics of the light-emitting device 2.
Figure 29:
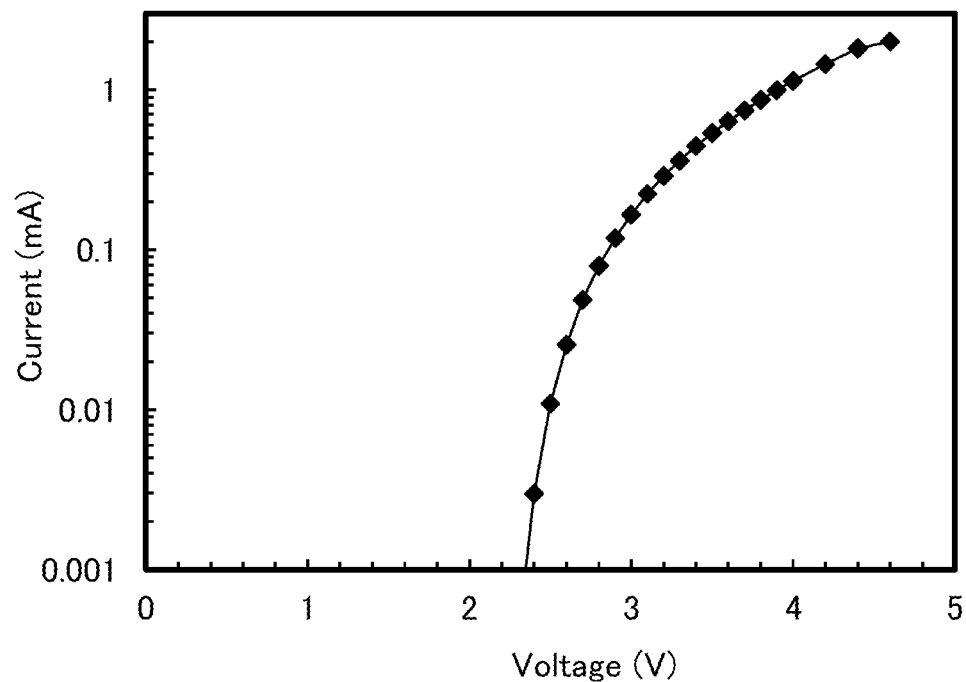
FIG. 29 is Current-voltage characteristics of the light-emitting device 2.
Figure 30:
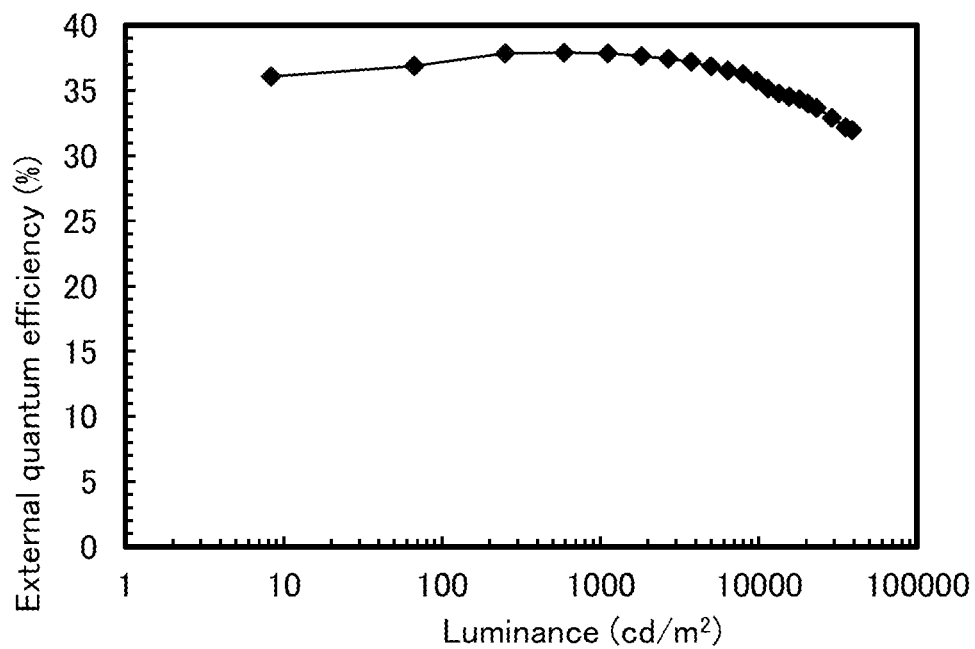
FIG. 30 is External quantum efficiency—luminance characteristics of the light-emitting device 2.
Figure 31:
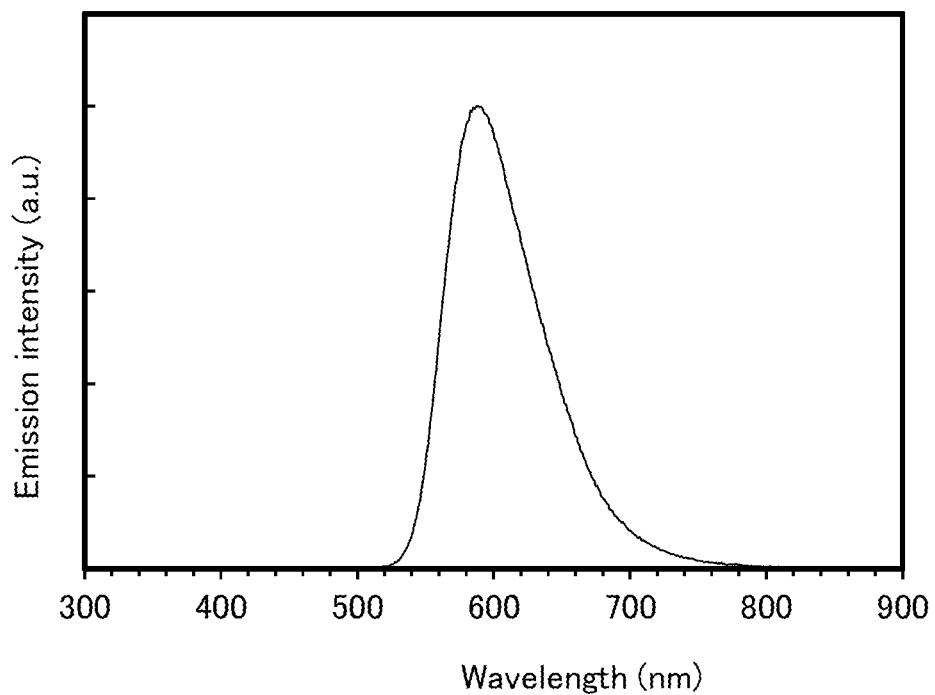
FIG. 31 is the emission spectrum of the light-emitting device 2.

FIG. 26 shows the luminance-current density characteristics of the light-emitting device 2; FIG. 27, the current efficiency-luminance characteristics; FIG. 28, the luminance-voltage characteristics; FIG. 29, the current-voltage characteristics; FIG. 30, the external quantum efficiency-luminance characteristics; and FIG. 31, the emission spectrum. In addition, Table 4 shows the main characteristics of the light-emitting device 2 at around 1000 cd/m$^2$. Note that the measurement method is similar to that in Example 3. Note that the external quantum efficiency in FIG. 30 shows values under the assumption of Lambertian, and for external quantum efficiency in the table below, the true values obtained by correcting deviation with respect to Lambertian distribution after measuring the angular dependency of an emission spectrum are adopted.

TABLE 4

| Voltage (V) | Current (mA) | Current density (mA/cm$^2$) | Chromaticity x | Chromaticity y | Current efficiency (cd/A) | External quantum efficiency (%) |
|---|---|---|---|---|---|---|
| 2.7 | 0.05 | 1.2 | 0.57 | 0.43 | 92.1 | 35.4 |

It was found from FIG. 26 to FIG. 31 and Table 4 that the light-emitting device 2 of one embodiment of the present invention was a yellow-orange light-emitting device with high emission efficiency. In particular, the external quantum efficiency exceeds 35%. Given the fact that the limit of light extraction efficiency of an EL device is considered to be approximately 30%, the external quantum efficiency of the present device is extremely high. This derives from the improvement in light extraction efficiency due to usage of TAPC-02 with a low refractive index.

EXAMPLE 5

In this example, a light-emitting device 3 of one embodiment of the present invention will be described. Structural formulae of organic compounds used in the light-emitting device 3 are shown below.

[Chemical Formulae 35]

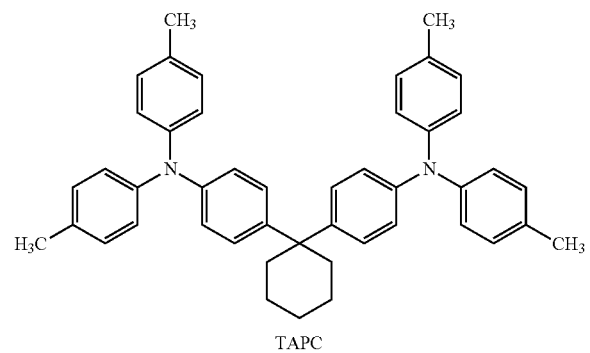

(vii) TAPC

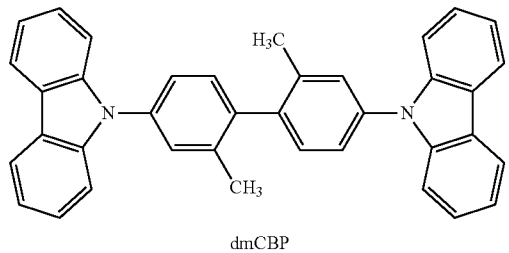

(i) dmCBP (ii)

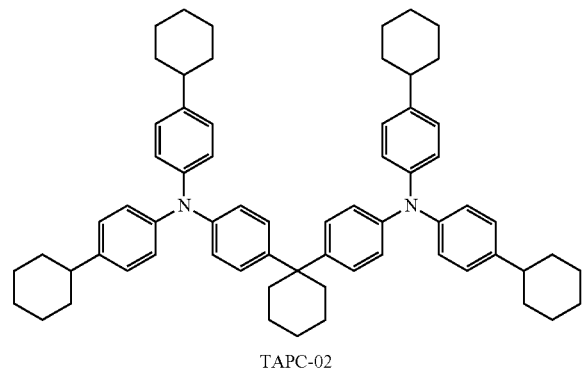

TAPC-02

(iii)

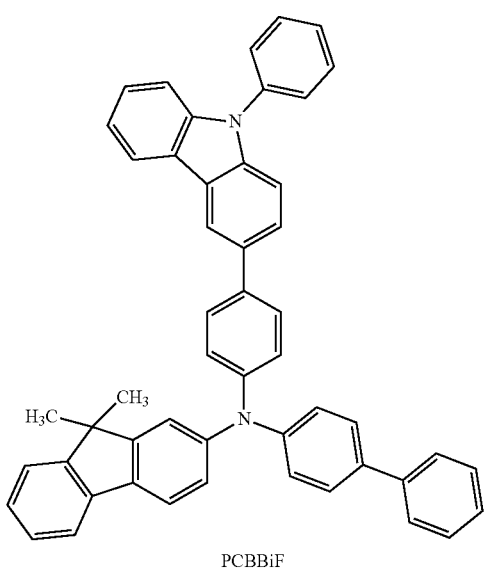

PCBBiF (iv)

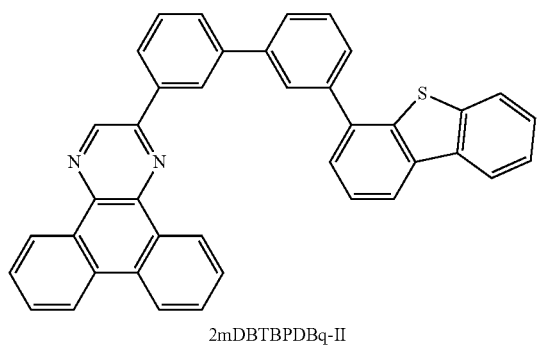

2mDBTBPDBq-II (ix)

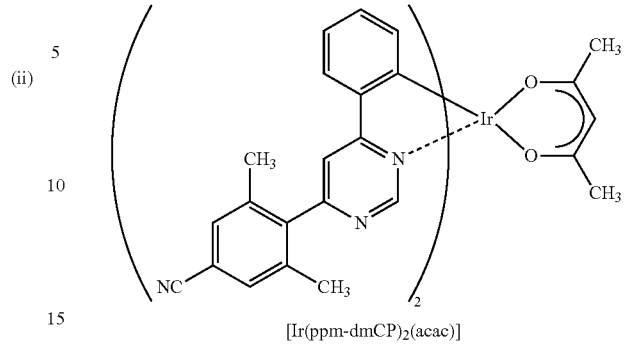

[Ir(ppm-dmCP)₂(acac)]

(x)

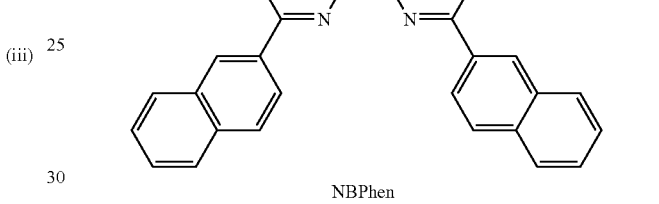

NBPhen (vi)

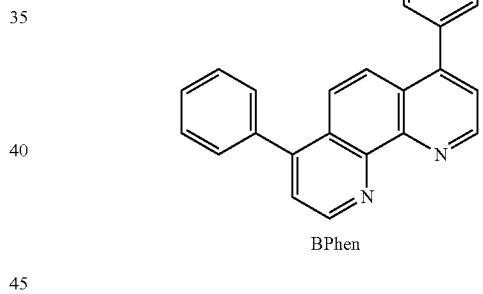

BPhen (Fabrication Method of Light-Emitting Device 3)

First, a film of indium tin oxide containing silicon oxide (ITSO) was formed over a glass substrate by a sputtering method, so that the first electrode 101 was formed. Note that the thickness was 70 nm and the area of the electrode was 2 mm×2 mm.

Next, in pretreatment for forming the light-emitting device over the substrate, the surface of the substrate was washed with water and baked at 200° C. for one hour, and then UV ozone treatment was performed for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate over which the first electrode 101 was formed was fixed to a substrate holder provided in the vacuum evaporation apparatus so that the surface over which the first electrode 101 was formed faced downward, and calcium fluoride (CaF₂), 1,1-bis-(4-bis(4-methyl-phenyl)-amino-phenyl)-cyclohexane (abbreviation: TAPC) represented by the above structural formula (vii), and molybdenum(VI) oxide were co-evaporated over the first electrode 101 to have a weight ratio of 3:1:0.5 (=CaF$_2$: TAPC: molybdenum oxide) to a thickness of 45 nm by an evaporation method using resistance heating, and then, 4,4'-bis(9-carbazole)-2,2'-dimethyl-biphenyl (abbreviation: dmCBP) represented by the above structural formula (i) and molybdenum(VI) oxide were co-evaporated to have a weight ratio of 2:0.5 (=dmCBP: MoOx) to a thickness of 5 nm, whereby the hole-injection layer 111 was formed.

Next, 4,4'-(1,1-cyclohexane-diyl)bis[N,N-bis(4-cyclohexylbenzen-1-yl)aminobenzene] (abbreviation: TAPC-02) represented by the above structural formula (ii) was deposited to a thickness of 15 nm over the hole-injection layer 111 by evaporation, and then, N-(1,1'-biphenyl-4-yl)-9,9-dimethyl-N-[4-(9-phenyl-9H-carbazol-3-yl)phenyl]-9H-fluoren-2-amine (abbreviation: PCBBiF) represented by the above structural formula (iii) was deposited to a thickness of 5 nm by evaporation, whereby the hole-transport layer 112 was formed.

Subsequently, 2-[3'-(dibenzothiophen-4-yl)biphenyl-3-yl]dibenzo[f,h]quinoxaline (abbreviation: 2mDBTBPDBq-II) represented by the above structural formula (iv), PCBBiF, and bis{2-[6-(4-cyano-2,6-dimethylphenyl)-4-pyrimidinyl-κN$^3$]phenyl-κC}(2,4-pentanedionato-κO,O')iridium(III) (abbreviation: [Ir(ppm-dmCP)$_2$(acac)]) represented by the above structural formula (ix) were deposited by co-evaporation to have a weight ratio of 0.75:0.25:0.05 (=2mDBTBPDBq-II: PCBBiF: [Ir(ppm-dmCP)$_2$(acac)]) to a thickness of 40 nm, whereby the light-emitting layer 113 was formed.

After that, over the light-emitting layer 113, 2mDBTBPDBq-II was deposited by evaporation to a thickness of 5 nm, and then 2,9-bis(naphthalen-2-yl)-4,7-diphenyl-1,10-phenanthroline (abbreviation: NBPhen) represented by the above structural formula (x) was deposited by evaporation to a thickness of 5 nm, whereby the electron-transport layer 114 was formed.

After the formation of the electron-transport layer 114, lithium fluoride (LiF) and BPhen were deposited by co-evaporation to a thickness of 35 nm to have a weight ratio of 0.75:0.25 (=LiF: BPhen) to form the electron-injection layer 115, and then aluminum was deposited by evaporation to a thickness of 200 nm to form the second electrode 102, whereby the light-emitting device 3 of this example was fabricated.

The device structure of the light-emitting device 3 is shown in the following table.

TABLE 5

| Electron-injection layer | 35 nm | LiF:BPhen (0.75:0.25[vol %]) |
|---|---|---|

TABLE 5-continued

| Electron-transport layer | 5 nm | NBPhen |
|---|---|---|
| | 5 nm | 2mDBTBPDBq-II |
| Light-emitting layer | 40 nm | 2mDBTBPDBq-II:PCBBiF:Ir(ppm-cmCP)$_2$(acac) (40 0.75:0.25:0.05) |
| Hole-transport layer | 5 nm | PCBBiF |
| | 15 nm | TAPC-02 |
| Hole-injection layer | 5 nm | dmCBP:MoOx(2:0.5) |
| | 45 nm | CaF$_2$:TAPC:MoOx (3:1:0.5) |

The light-emitting device 3 was sealed using a glass substrate in a glove box containing a nitrogen atmosphere so as not to be exposed to the air (a sealant was applied to surround the device, and UV treatment and 1-hour heat treatment at 80° C. were performed in sealing). Then, initial characteristics of the light-emitting device 3 were measured. Note that the glass substrate over which the light-emitting device was formed was not subjected to particular treatment for improving outcoupling efficiency.

Figure 32:
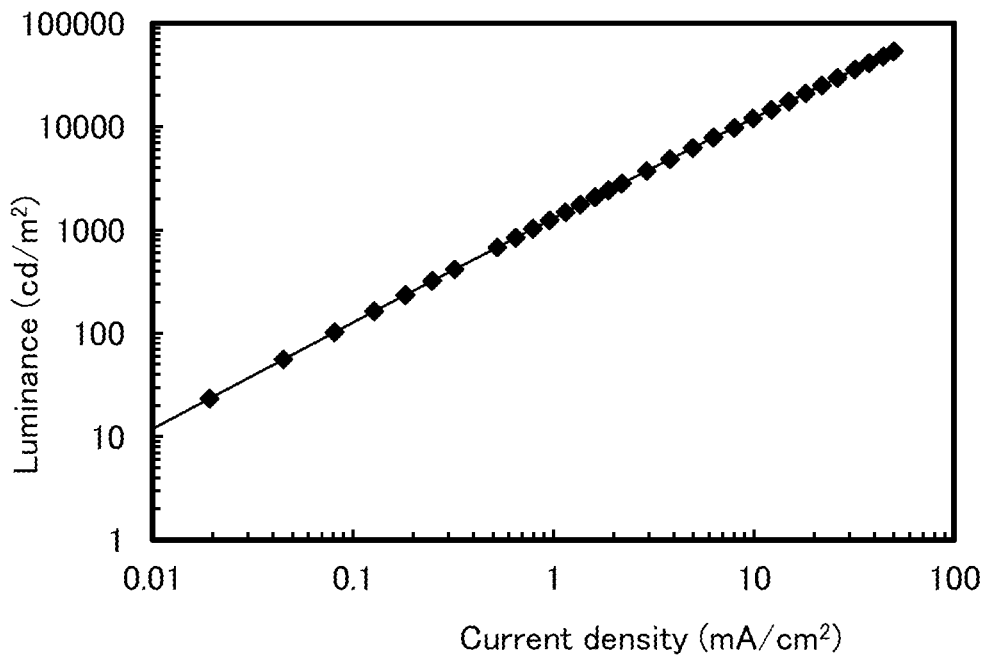
FIG. 32 is Luminance—current density characteristics of a light-emitting device 3.
Figure 33:
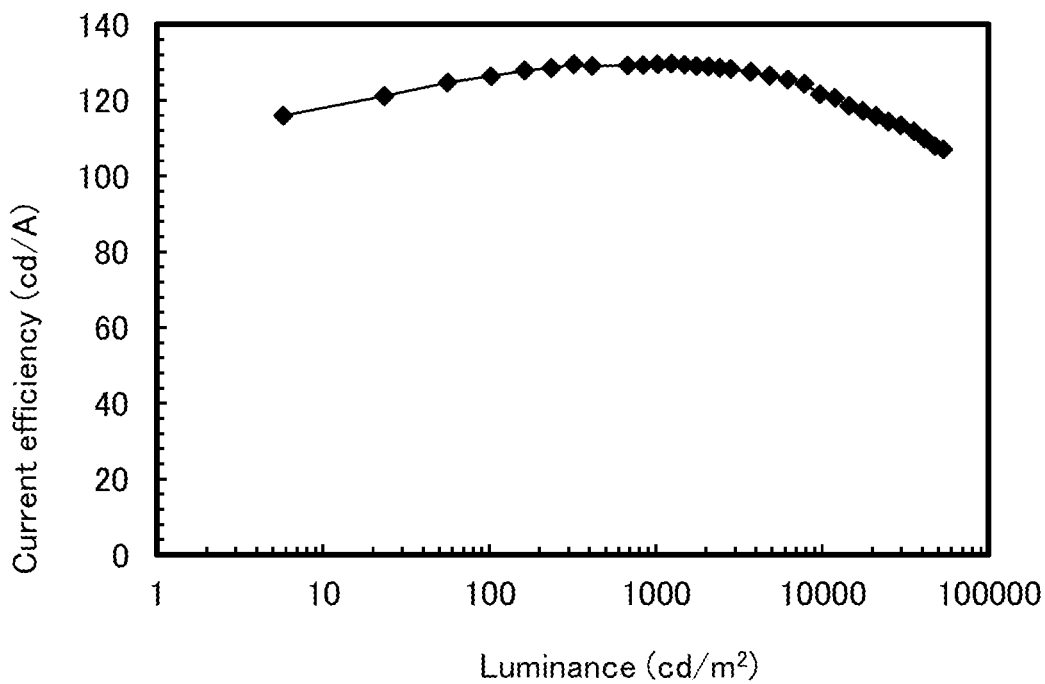
FIG. 33 is Current efficiency—luminance characteristics of the light-emitting device 3.
Figure 34:
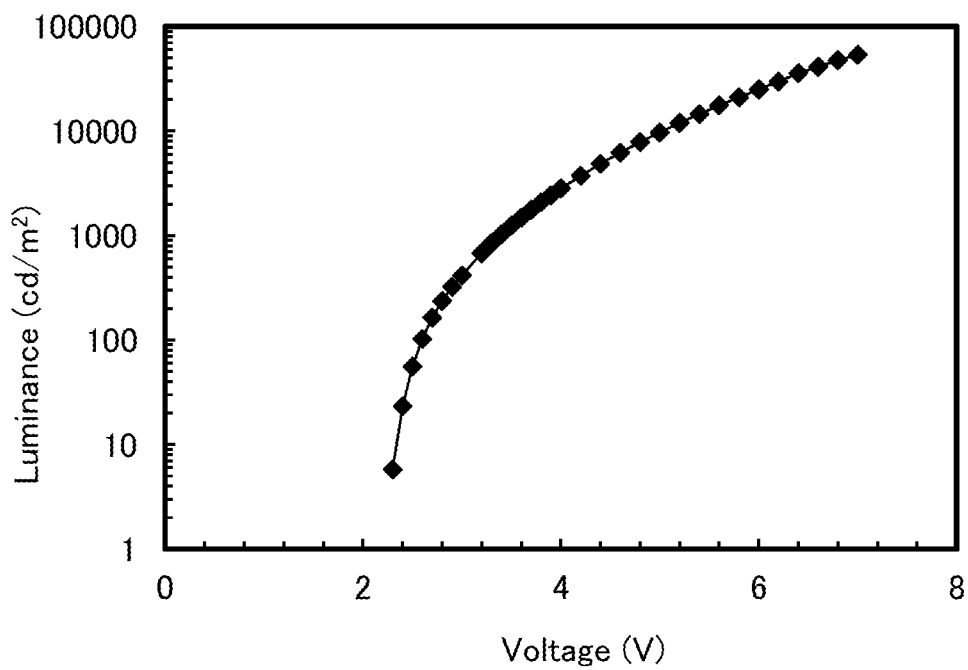
FIG. 34 is Luminance—voltage characteristics of the light-emitting device 3.
Figure 35:
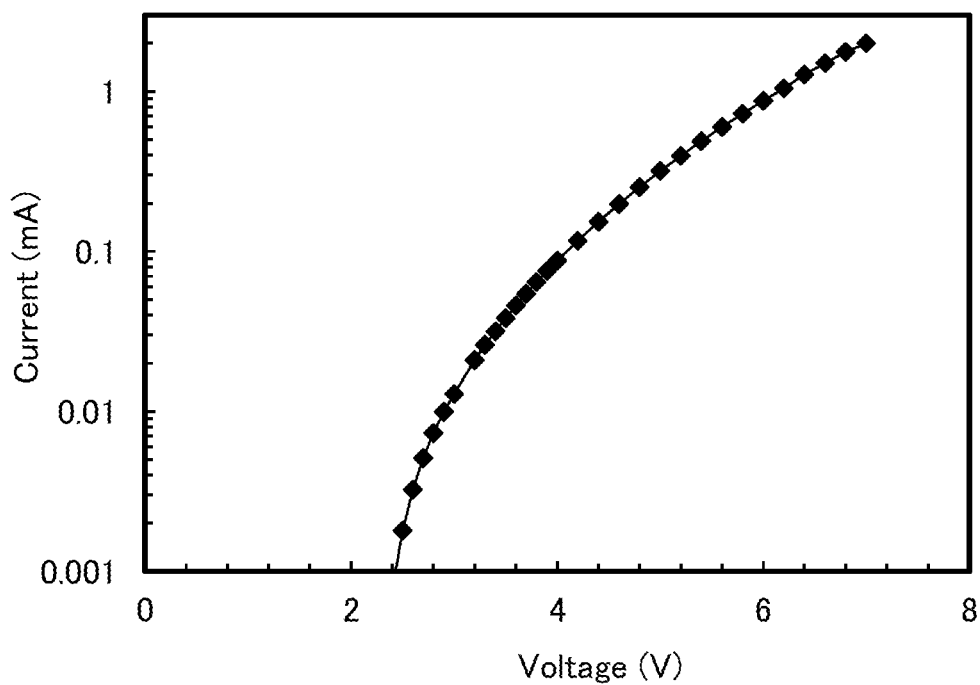
FIG. 35 is Current—voltage characteristics of the light-emitting device 3.
Figure 36:
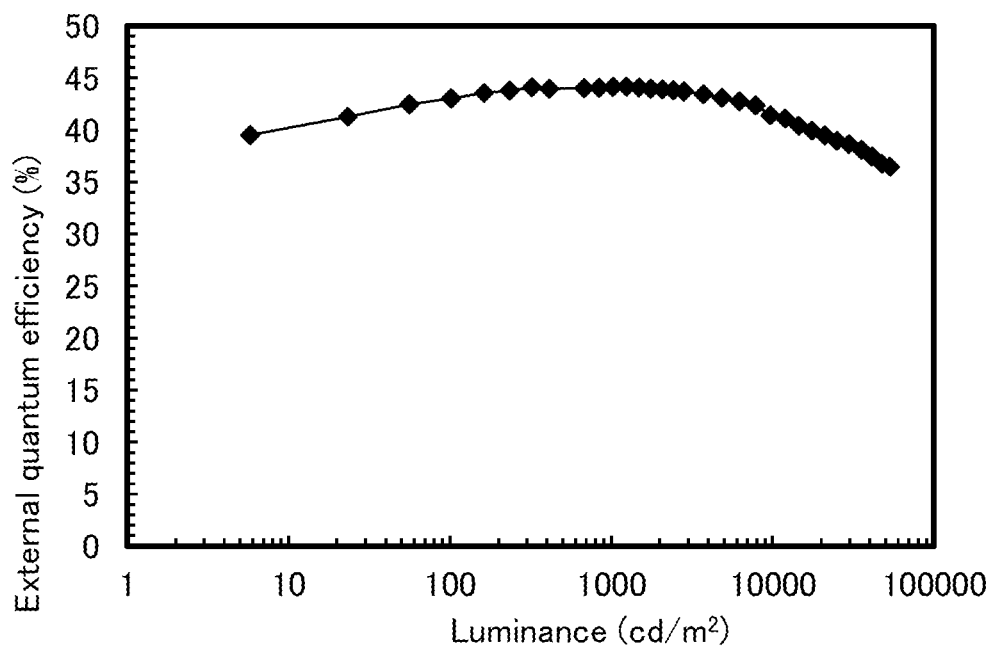
FIG. 36 is External quantum efficiency—luminance characteristics of the light-emitting device 3.
Figure 37:
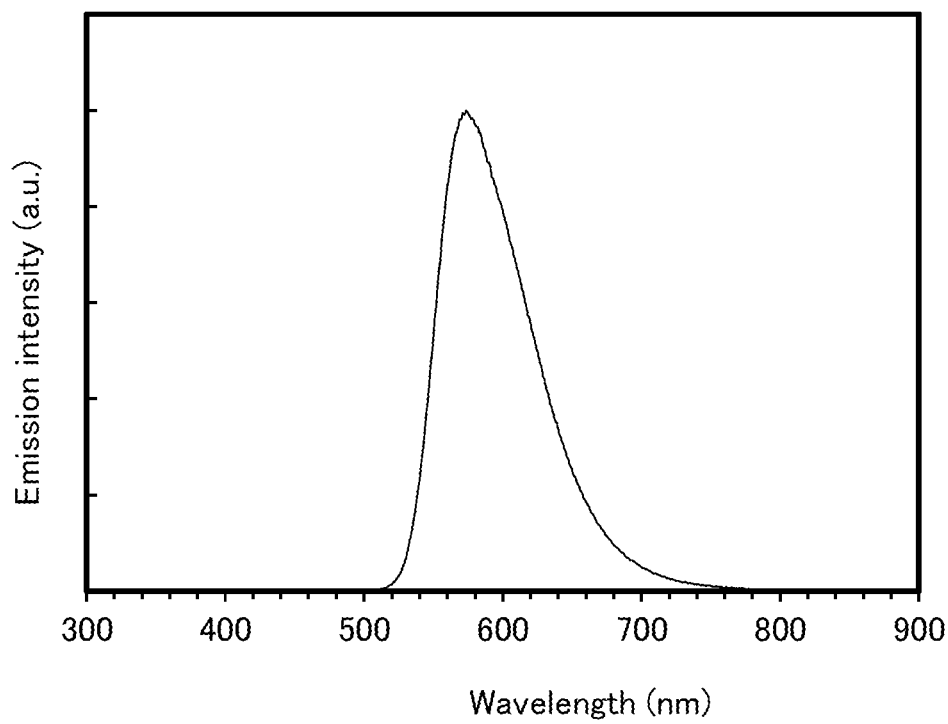
FIG. 37 is the emission spectrum of the light-emitting device 3.

FIG. 32 shows the luminance-current density characteristics of the light-emitting device 3; FIG. 33, the current efficiency-luminance characteristics; FIG. 34, the luminance-voltage characteristics; FIG. 35, the current-voltage characteristics; FIG. 36, the external quantum efficiency-luminance characteristics; and FIG. 37, the emission spectrum. In addition, Table 6 shows the main characteristics of the light-emitting device 3 at around 1000 cd/m$^2$. Note that the measurement method is similar to that in Example 3. Note that the external quantum efficiency in FIG. 36 shows values under the assumption of Lambertian, and for external quantum efficiency in the table below, the true values obtained by correcting deviation with respect to Lambertian distribution after measuring the angular dependency of an emission spectrum are adopted.

TABLE 6

| Voltage (V) | Current (mA) | Current density (mA/cm$^2$) | Chromaticity x | Chromaticity y | Current efficiency (cd/A) | External quantum efficiency (%) |
|---|---|---|---|---|---|---|
| 3.4 | 0.03 | 0.8 | 0.52 | 0.47 | 129.5 | 42.5 |

It was found from FIG. 32 to FIG. 37 and Table 4 that the light-emitting device 3 of one embodiment of the present invention exhibits extremely high efficiency, with its external quantum efficiency being 42.5%. Accordingly, it was found that the use of the compound of one embodiment of the present invention enables a light-emitting device with high emission efficiency to be obtained.

REFERENCE SYNTHESIS EXAMPLE

In this reference synthesis example, a method for synthesizing bis{2-[6-(4-cyano-2,6-dimethylphenyl)-4-pyrimidinyl-κN$^3$]phenyl-κC}(2,4-pentanedionato-κO,O')iridium (III)) (abbreviation: [Ir(ppm-dmCP)$_2$(acac)]) will be described. The structure of [Ir(ppm-dmCP)$_2$(acac)] is shown below.

[Chemical Formula 36]

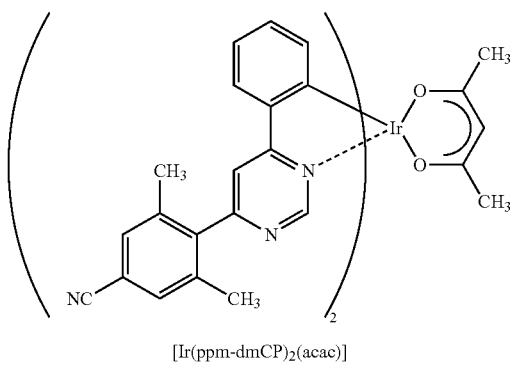

[Ir(ppm-dmCP)₂(acac)]

Step 1: Synthesis of 3,5-dimethyl-4-(4,4,5,5-tetramethyl-1,3,2-dioxaborolan-2-yl)benzonitrile Into a three-neck flask equipped with a reflux pipe were put 10.06 g of 4-bromo-3,5-dimethylbenzonitrile, 18.35 g of bis(pinacolato)diboron, 21.73 g of potassium acetate, and 240 mL of dimethyl sulfoxide, and the air in the flask was replaced with nitrogen. After the mixture in the flask was degassed by being stirred under reduced pressure, 0.59 g of [1,1'-bis(diphenylphosphino)ferrocene]palladium(II) dichloride dichloromethane adduct (abbreviation: Pd(dppf)Cl₂·CH₂Cl₂) and 0.59 g of 2-dicyclohexylphosphino-2',6'-dimethoxybiphenyl (abbreviation: S-Phos) were added, and the mixture was stirred at 100° C. for 32.5 hours. After the elapse of the predetermined period, extraction was performed with toluene. Then, purification by silica gel column chromatography using a developing solvent of hexane: ethyl acetate=10:1 was performed, so that a target substance (5.89 g of a white solid, in a yield of 48%) was obtained. The synthesis scheme of Step 1 is shown in (a-1) below.

[Chemical Formula 37]

(a-1)

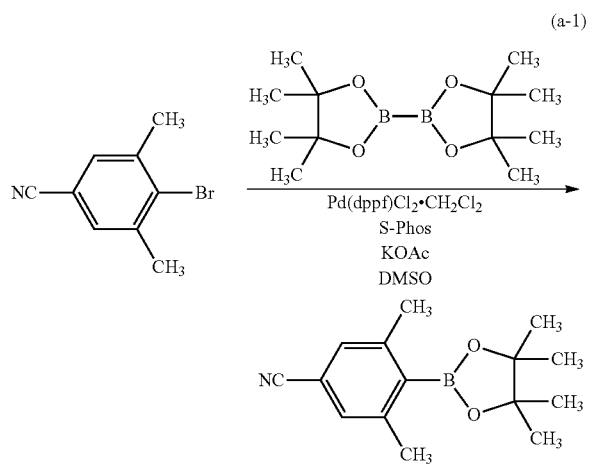

Step 2: Synthesis of 4-(4-cyano-2,6-dimethylphenyl)-6-phenylpyrimidine (abbreviation: Hppm-dmCP)

Next, 0.74 g of 4-chloro-6-phenylpyrimidine, 1.28 g of 3,5-dimethyl-4-(4,4,5,5-tetramethyl-1,3,2-dioxaborolan-2-yl)benzonitrile obtained in Step 1 described above, 3.23 g of tripotassium phosphate, 43 mL of toluene, and 4.3 mL of water were put into a three-neck flask equipped with a reflux pipe, and the air in the flask was replaced with nitrogen. The mixture in the flask was degassed by being stirred under reduced pressure, 0.094 g of tris(dibenzylideneacetone)dipalladium(0) (abbreviation: Pd₂(dba)₃) and 0.19 g of tris(2,6-dimethoxyphenyl)phosphine (abbreviation: P(2,6-MeOPh)₃) were added thereto, and the mixture was stirred at 110° C. for 23 hours. After the elapse of the predetermined period, extraction was performed with toluene. Then, purification by silica gel column chromatography using hexane: ethyl acetate=5:1 as a developing solvent was performed, so that a target pyrimidine derivative Hppm-dmCP (0.97 g of a white solid in a yield of 88%) was obtained. The synthesis scheme of Step 2 is shown in (a-2) below.

[Chemical Formula 38]

(a-2)

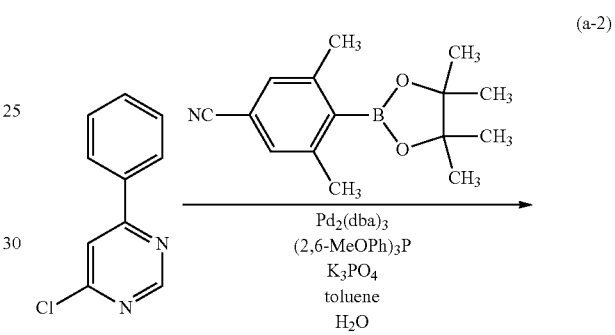

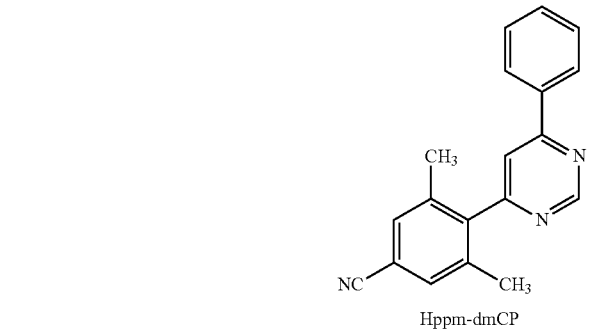

Hppm-dmCP

Step 3: Synthesis of Di-µ-chloro-tetrakis{2-[6-(4-cyano-2,6-dimethylphenyl)-4-pyrimidinyl-κN³]phenyl-κC}diiridium(III) (abbreviation: [Ir(ppm-dmCP)₂Cl]₂)

Next, 15 mL of 2-ethoxyethanol, 5 mL of water, 1.60 g of Hppm-dmCP obtained in Step 2 described above, and 0.81 g of iridium chloride hydrate (IrCl₃·H₂O) (produced by Furuya Metal Co., Ltd.) were put into a recovery flask equipped with a reflux pipe, and the air in the flask was replaced with argon. Then, microwave irradiation (2.45 GHz, 100 W) was performed for 3 hours to cause reaction. After the elapse of the predetermined period, the obtained residue was suction-filtered and washed with methanol to give a dinuclear complex [Ir(ppm-dmCP)₂Cl]₂ (1.45 g of an orange solid, in a yield of 67%). The synthesis scheme of Step 3 is shown in (a-3) below.

[Chemical Formula 39]

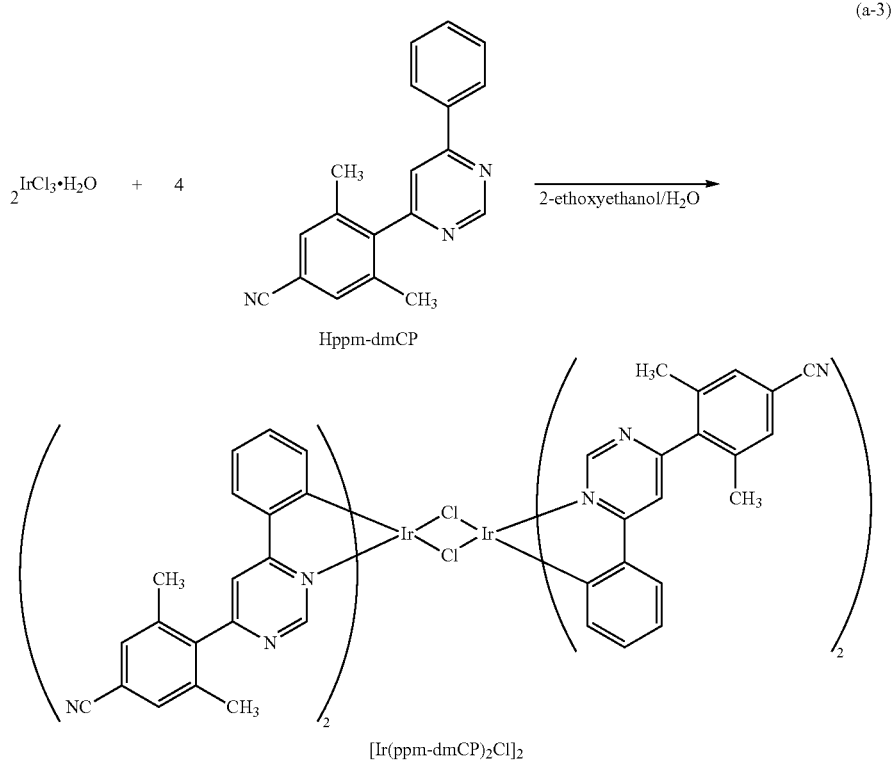

Hppm-dmCP

[Ir(ppm-dmCP)$_2$Cl]$_2$

Step 4: Synthesis of: [Ir(ppm-dmCP)$_2$(acac)]

Into a recovery flask equipped with a reflux pipe were put 20 mL of 2-ethoxyethanol, 1.44 g of the dinuclear complex [Ir(ppm-dmCP)$_2$Cl]$_2$ obtained through Step 3 described above, 0.41 g of acetylacetone (abbreviation: Hacac), and 0.93 g of sodium carbonate, and the air in the flask was replaced with argon. Then, microwave irradiation (2.45 GHz, 100 W) was performed for 4 hours. The obtained residue was suction-filtered with dichloromethane, and then the obtained filtrate was concentrated. The obtained solid was purified by silica gel column chromatography using hexane:ethyl acetate=2:1 as a developing solvent, and then recrystallization was performed from a mixed solvent of dichloromethane and methanol, whereby an organometallic complex [Ir(ppm-dmCP)$_2$(acac)] was obtained as a yellow-orange powder (0.19 g in amount, in a yield of 7%). By a train sublimation method, 0.19 g of the obtained yellow-orange solid was purified by sublimation. In the purification by sublimation, the solid was heated at 355° C. under a pressure of 2.7 Pa with an argon gas flow rate of 11 mL/min. After the sublimation purification, 0.092 g of an objective yellow-orange solid was obtained in a yield of 48%. The synthesis scheme of Step 4 is shown in (a-4) below.

[Chemical Formula 40]

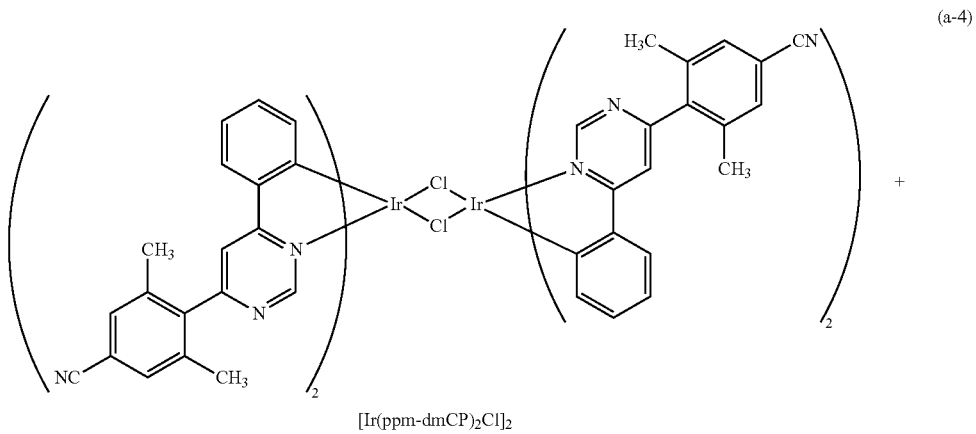

[Ir(ppm-dmCP)$_2$Cl]$_2$

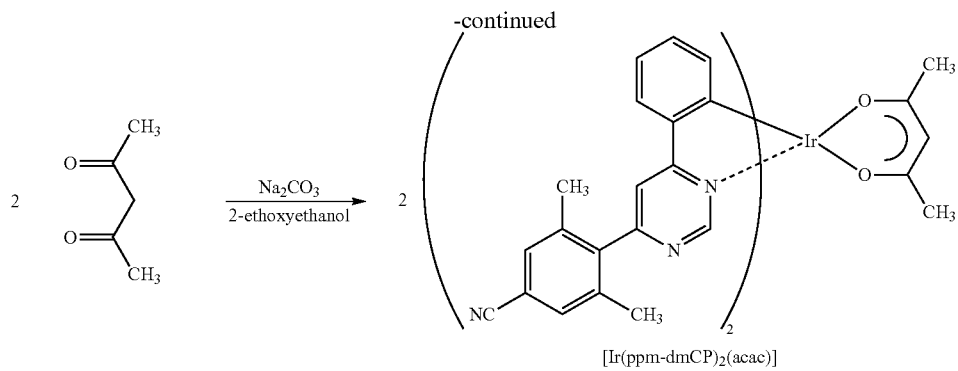

[Ir(ppm-dmCP)₂(acac)]

Analysis results by nuclear magnetic resonance (¹H-NMR) spectroscopy of the yellow-orange solid obtained in Step 4 above are shown below. These results reveal that [Ir(ppm-dmCP)₂(acac)] was obtained in this synthesis example.

¹H-NMR. δ (CDCl₃): 1.86 (s, 6H), 2.29 (s, 12H), 5.36 (s, 1H), 6.44 (d, 2H), 6.86 (t, 2H), 6.91 (t, 2H), 7.52 (s, 4H), 7.66 (d, 2H), 7.68 (s, 2H), 9.25 (s, 2H).

REFERENCE NUMERALS

101: first electrode, 102: second electrode, 103: EL layer, 111: hole-injection layer, 112: hole-transport layer, 113: light-emitting layer, 114: electron-transport layer, 115: electron-injection layer, 116: charge-generation layer, 117: p-type layer, 118: electron-relay layer, 119: electron-injection buffer layer, 400: substrate, 401: first electrode, 403: EL layer, 404: second electrode, 405: sealant, 406: sealant, 407: sealing substrate, 412: pad, 420: IC chip, 501: anode, 502: cathode, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealant, 607: space, 608: wiring, 609: FPC (flexible printed circuit), 610: device substrate, 611: switching FET, 612: current control FET, 613: first electrode, 614: EL layer, 616: insulator, 617: second electrode, 618: light-emitting device, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: first electrode, 1024R: first electrode, 1024G: first electrode, 1024B: first electrode, 1025: partition, 1028: EL layer, 1029: second electrode, 1031: sealing substrate, 1032: sealant, 1033: transparent base material, 1034R: red coloring layer, 1034G: green coloring layer, 1034B: blue coloring layer, 1035: black matrix, 1037: third interlayer insulating film, 1040: pixel portion, 1041: driver circuit portion, 1042: peripheral portion, 2001: housing, 2002: light source, 2100: robot, 2110: arithmetic device, 2101: illuminance sensor, 2102: microphone, 2103: upper camera, 2104: speaker, 2105: display, 2106: lower camera, 2107: obstacle sensor, 2108: moving mechanism, 3001: lighting device, 5000: housing, 5001:display portion, 5002: display portion, 5003: speaker, 5004: LED lamp, 5005: operation key, 5006: connection terminal, 5007: sensor, 5008: microphone, 5012: support, 5013: earphone, 5100: cleaning robot, 5101: display, 5102: camera, 5103: brush, 5104: operation button, 5150: portable information terminal, 5151: housing, 5152:display region, 5153: bend portion, 5120: dust, 5200:display region, 5201:display region, 5202: display region, 5203:display region, 7101: housing, 7103: display portion, 7105: stand, 7107:display portion, 7109: operation key, 7110: remote controller, 7201: main body, 7202: housing, 7203:display portion, 7204: keyboard, 7205: external connection port, 7206: pointing device, 7210: second display portion, 7401: housing, 7402:display portion, 7403: operation button, 7404: external connection port, 7405: speaker, 7406: microphone, 9310: portable information terminal, 9311: display panel, 9312: display region, 9313: hinge, 9315: housing This application is based on Japanese Patent Application Serial No. 2018-095707 filed with Japan Patent Office on May 17, 2018, the entire contents of which are hereby incorporated herein by reference.

The invention claimed is:
1. An organic compound represented by formula (G1),

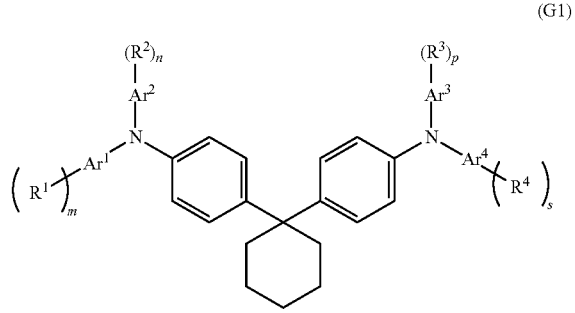

(G1)

wherein each of Ar¹ to Ar⁴ independently represent represents any of a substituted or unsubstituted phenylene group, a substituted or unsubstituted biphenyldiyl group, and a substituted or unsubstituted terphenyldiyl group, wherein each of R¹ and R⁴ independently represents an open-chain saturated hydrocarbon group having 5 to 12 carbon atoms or a substituted or unsubstituted cyclic saturated hydrocarbon group having 5 to 12 carbon atoms, wherein each of R² and R³ independently represents a substituted or unsubstituted cyclic saturated hydrocarbon group having 5 to 12 carbon atoms, wherein each of m and s independently represent an integer of 0 to 3, and wherein each of n and p independently represents an integer of 1 to 3.

2. The organic compound according to claim 1, wherein each of Ar¹ and Ar⁴ is a substituted or unsubstituted phenylene group.

3. The organic compound according to claim 1, wherein each of Ar² and Ar³ is a substituted or unsubstituted biphenyldiyl group.

4. The organic compound according to claim 1, wherein each of Ar¹ to Ar⁴ is a substituted or unsubstituted phenylene group.

5. The organic compound according to claim 1,
wherein the organic compound is represented by formula (G2),

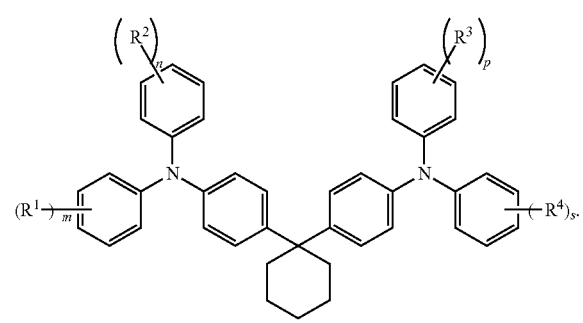

(G2)

6. The organic compound according to claim 1,
wherein the organic compound is represented by formula (G4)

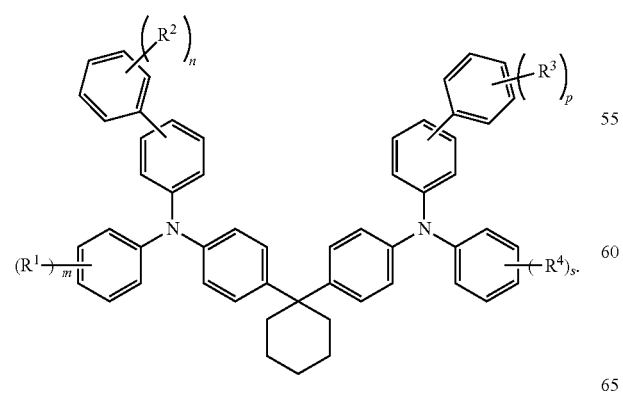

(G4)

7. The organic compound according to claim 1,
wherein the organic compound is represented by formula (G5)

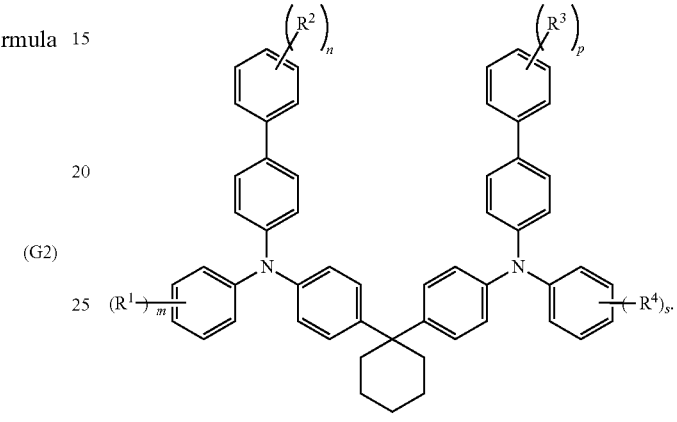

(G5)

8. The organic compound according to claim 1, wherein each of m and s independently represents an integer of 1 to 3.

9. The organic compound according to claim 1, wherein each of m, n, p and s is 1.

10. The organic compound according to claim 1,
wherein the organic compound is represented by formula (G3)

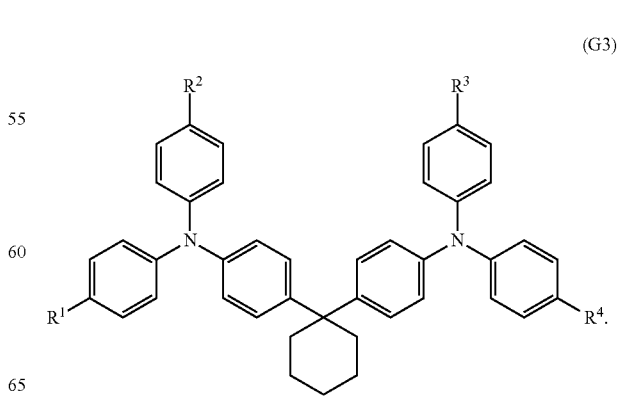

(G3)

11. The organic compound according to claim 1, wherein the organic compound is represented by formula (G6)

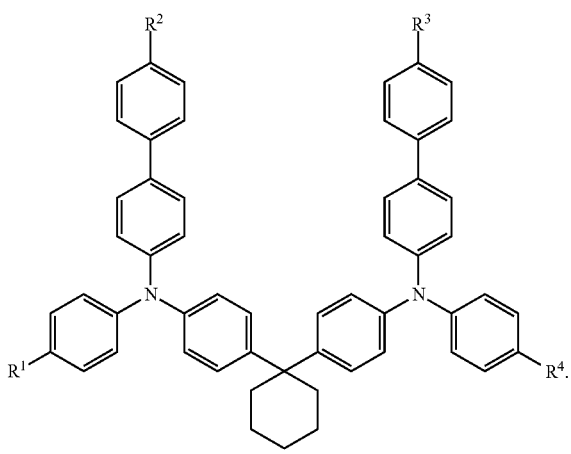

(G6)

12. The organic compound according to claim 1, wherein $R^1$ to $R^4$ are each independently a cyclohexyl group.

13. The organic compound according to claim 1, wherein the organic compound is represented by the following formula

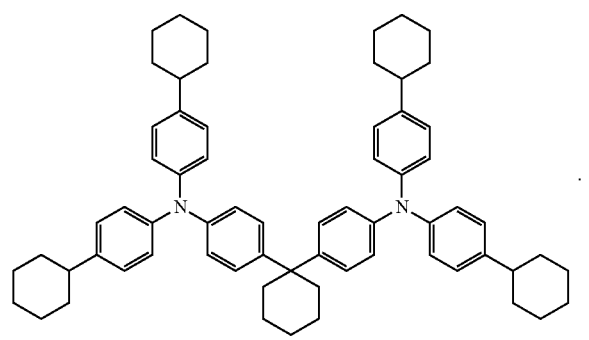 [SMILES: c1cc(N(c2ccc(C3CCCCC3)cc2)c2ccc(C3(c4ccc(N(c5ccc(C6CCCCC6)cc5)c5ccc(C6CCCCC6)cc5)cc4)CCCCC3)cc2)ccc1C1CCCCC1]

14. The organic compound according to claim 1, wherein the organic compound is represented by the following formula

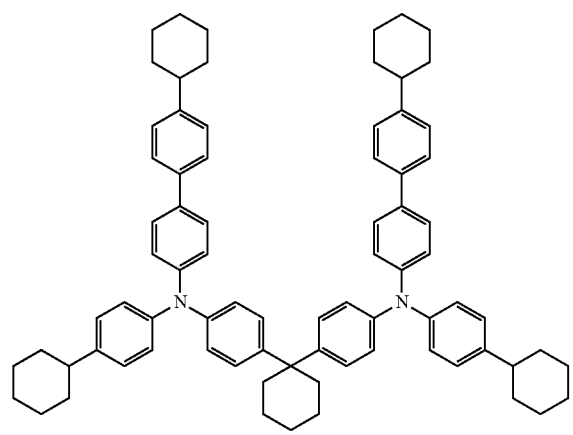

15. A light-emitting device comprising:
a first electrode;
a second electrode over the first electrode; and
an electroluminescent layer between the first electrode and the second electrode,
wherein the electroluminescent layer comprises the organic compound according to claim claim 1.

16. A light-emitting device comprising:
a first electrode;
a second electrode over the first electrode; and
an electroluminescent layer between the first electrode and the second electrode,
wherein the electroluminescent layer comprises at least a light-emitting layer and a hole-transport layer, and
wherein the hole-transport layer comprises the organic compound according to claim 1.

17. A light-emitting device comprising:
a first electrode;
a second electrode over the first electrode; and
an electroluminescent layer between the first electrode and the second electrode,
wherein the electroluminescent layer comprises at least a light-emitting layer and a hole-injection layer, and
wherein the hole-injection layer comprises the organic compound according to claim 1.

18. A light-emitting device comprising:
a first electrode;
a second electrode over the first electrode; and
an electroluminescent layer between the first electrode and the second electrode,
wherein the electroluminescent layer comprises a light-emitting layer, a hole-transport layer and a hole-injection layer, and
wherein each of the hole-transport layer and the hole-injection layer comprises the organic compound according to claim 1.

19. A light-emitting apparatus comprising:
the light-emitting device according to claim 15; and
one of a transistor and a substrate.

20. Electronic equipment comprising:
the light-emitting apparatus according to claim 19; and
one of a sensor, an operation button, a speaker and a microphone.

21. A lighting device comprising:
the light-emitting apparatus according to claim 19; and
a housing.

22. An electronic device comprising the organic compound according to claim 1.

* * * * *